US010323229B1

(12) United States Patent
Li

(10) Patent No.: US 10,323,229 B1
(45) Date of Patent: Jun. 18, 2019

(54) THREE-DIMENSIONAL HUMAN STEM CELL-DERIVED CORTICAL SPHEROID MODEL

(71) Applicant: The Florida State University Research Foundation, Inc., Tallahassee, FL (US)

(72) Inventor: Yan Li, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/350,395

(22) Filed: Nov. 14, 2016

Related U.S. Application Data

(60) Provisional application No. 62/254,735, filed on Nov. 13, 2015.

(51) Int. Cl.
C12N 5/074 (2010.01)
G01N 33/50 (2006.01)

(52) U.S. Cl.
CPC ....... *C12N 5/0696* (2013.01); *G01N 33/5058* (2013.01); *G01N 33/5073* (2013.01); *C12N 2501/15* (2013.01); *C12N 2501/41* (2013.01); *C12N 2501/727* (2013.01); *C12N 2506/1307* (2013.01)

(58) Field of Classification Search
CPC .............................. G06T 11/206; G06F 19/321
USPC ......................................................... 345/440
See application file for complete search history.

(56) References Cited

U.S. PATENT DOCUMENTS

2016/0272940 A1* 9/2016 Chung .................... A61K 35/30

OTHER PUBLICATIONS

Wattanapanitch et al (PLOS One 9: 1-8, 2014).*
Serra et al (J Neurosc Res 85: 3557-3566, 2007).*
Wheaton® Celstir® glass spinner flasks, downloaded on Feb. 3, 2018, from <http://www.capitolscientific.com/lab-supplies/wheaton-celstir-jacketed-glass-spinner-flask-with-double-sidearms-for-cell-culture>.*
Wheaton 356875.*
Gaspard et al (Nat Protocols 4: 1454-1463, 2009).*
Ota et al (Dev Dynamics 227: 544-551, 2003).*
Incardona et al (Development 125: 3553-3562, 1998).*
He et al (Neurochem Res 41: 687-695, Oct. 12, 2015).*
Vazin et al (Neurobiol Dis 62: 1-24, 2014).*
Van den Ameele, et al., Thinking out of the dish: what to learn about cortical development using pluripotent stem cells, Trends Neurosci, 37 (2014) 334-342.
Van Hove, et al., An aberrant cerebellar development in mice lacking matrix metalloproteinase-3, Mol Neurobiol, 45 (2012) 17-29.
Vazin, et al., Efficient derivation of cortical glutamatergic neurons from human pluripotent stem cells: a model system to study neurotoxicity in Alzheimer's disease, Neurobiol Dis, 62 (2014) 62-72.
Vazin, et al., The effect of multivalent Sonic hedgehog on differentiation of human embryonic stem cells into dopaminergic and GABAergic neurons, Biomaterials, 35 (2014) 941-948.
Yahata, et al., Anti-Abeta drug screening platform using human iPS cell-derived neurons for the treatment of Alzheimer's disease, PLoS One, 6 (2011) e25788.
Yan, et al., Differential effects of acellular embryonic matrices on pluripotent stem cell expansion and neural differentiation., Biomaterials, 73 (2015) 231-242.
Zhang, et al., A 3D Alzheimer's disease culture model and the induction of P21-activated kinase mediated sensing in PSC derived neurons, Biomaterials, 35 (2014) 1420-1428.
Kaul, M., HIV-1 associated dementia: update on the pathological mechanisms and therapeutic approaches, Curr Opin Neurol. Jun. 2009; 22(3): 315-320.
Nath, A., Human Immunodeficiency Virus (HIV) Proteins in Neuropathogenesis of HIV Dementia, The Journal of Infectious Diseases. 2002; 186(Suppl 2): S193-8.
Newcomb-Fernandez, et al., Concurrent Assessment of Calpain and Caspase-3 Activation After Oxygen-Glucose Deprivation in Primary Septo-Hippocampal Cultures. Journal of Cerebral Blood Flow and Metabolism. 2001; 21:1281-1294.
Abbasi, et al., Influence of oriented nanofibrous PCL scaffolds on quantitative gene expression during neural differentiation of mouse embryonic stem cells, J Biomed Mater Res A, 104 (2016) 155-164.
Arlotta, et al., Neuronal subtype-specific genes that control corticospinal motor neuron development in vivo. Neuron. Jan. 20, 2005;45(2):207-21.
Barkho, et al., Endogenous matrix metalloproteinase (MMP)-3 and MMP-9 promote the differentiation and migration of adult neural progenitor cells in response to chemokines, Stem Cells, 26 (2008) 3139-3149.
Beraki, et al., A pharmacological screening approach for discovery of neuroprotective compounds in ischemic stroke, PLoS One, 8 (2013) e69233.
Briscoe & Therond, The mechanisms of Hedgehog signalling and its roles in development and disease, Nat Rev Mol Cell Biol, 14 (2013) 416-429.
Chambers, et al., Highly efficient neural conversion of human ES and iPS cells by dual inhibition of SMAD signaling, Nat Biotechnol, 27 (2009) 275-280.

(Continued)

*Primary Examiner* — Daniel E Kolker
*Assistant Examiner* — Aditi Dutt
(74) *Attorney, Agent, or Firm* — Michele L. Lawson; Robert J. Varkonyi; Smith & Hopen, P.A.

(57) ABSTRACT

The present invention provides a new therapeutic method for modeling neuronal responses. Human induced pluripotent stem cells (hiPSCs) emerge recently as alternative sources of primary brain cells to establish Alzheimer's disease (AD) models in vitro. While previous investigations demonstrate the potential of hiPSCs in modeling AD, the 2-D cultures used in these studies cannot fully recapitulate AD-associated neuropathology. 3-D cortical spheroids (forebrain-like structure) were derived from human induced pluripotent stem cells in a bioreactor culture, which can be used to recapitulate AD-associated neuropathology, to screen the therapeutic drugs and to predict neurotoxicity.

6 Claims, 54 Drawing Sheets
Specification includes a Sequence Listing.

(56) References Cited

OTHER PUBLICATIONS

Chambers, et al., Build-a-brain, Cell Stem Cell, 13 (2013) 377-378.
Choi, et al., A three-dimensional human neural cell culture model of Alzheimer's disease, Nature, 515 (2014) 274-278.
Choi, et al., Size-controllable networked neurospheres as a 3D neuronal tissue model for Alzheimer's disease studies, Biomaterials, 34 (2013) 2938-2946.
Daley, et al., Extracellular matrix dynamics in development and regenerative medicine, J Cell Sci, 121 (2008) 255-264.
Di Giorgio, et al., Human embryonic stem cell-derived motor neurons are sensitive to the toxic effect of glial cells carrying an ALS-causing mutation, Cell Stem Cell, 3 (2008) 637-64.
Dimos, et al., Induced pluripotent stem cells generated from patients with ALS can be differentiated into motor neurons, Science, 321 (2008) 1218-1221.
Du, et al., Generation and expansion of highly pure motor neuron progenitors from human pluripotent stem cells, Nat Commun, 6 (2015) 6626.
Eiraku, et al., Self-organized formation of polarized cortical tissues from ESCs and its active manipulation by extrinsic signals, Cell Stem Cell, 3 (2008) 519-532.
Engle & Puppala, Integrating human pluripotent stem cells into drug development, Cell Stem Cell, 12 (2013) 669-677.
Ethell & Ethell, Matrix metalloproteinases in brain development and remodeling: synaptic functions and targets, J Neurosci Res, 85 (2007) 2813-2823.
Hedlund, et al., Global gene expression profiling of somatic motor neuron populations with different vulnerability identify molecules and pathways of degeneration and protection. Brain. Aug. 2010;133(Pr 8):2313-30.
Hosseinkhani, et al., Engineering three-dimensional collagen-IKVAV matrix to mimic neural microenvironment, ACS Chem Neurosci, 4 (2013) 1229-1235.
Hu & Zhang, Differentiation of spinal motor neurons from pluripotent human stem cells, Nat Protoc, 4 (2009) 1295-130.
Imaizumi, et al., Controlling the regional identity of hPSC-derived neurons to uncover neuronal subtype specificity of neurological disease phenotypes, Stem Cell Reports, 5 (2015) 1010-1022.
Ishizaki, et al., Pharmacological properties of Y-27632, a specific inhibitor of rho-associated kinases. Mol Pharmacol. May 2000;57(5);976-83.
Israel, et al., Probing sporadic and familial Alzheimer's disease using induced pluripotent stem cells, Nature, 482 (2012) 216-220.
Jiang, et al., Generation of cardiac spheres from primate pluripotent stem cells in a small molecule-based 3D system, Biomaterials, 65 (2015) 103-114.
Kondo, et al., Modeling Alzheimer's disease with iPSCs reveals stress phenotypes associated with intracellular Abeta and differential drug responsiveness, Cell Stem Cell, 12 (2013) 487-496.
Lancaster, et al., Cerebral organoids model human brain development and microcephaly, Nature, 501 (2013) 373-379.
Lancaster & Knoblich, Organogenesis in a dish: modeling development and disease using organoid technologies, Science, 345 (2014) 1247125.
Li, et al., In vitro organogenesis from pluripotent stem cells, Organogenesis, 10 (2014) 159-163.
Lu, et al., Extracellular matrix degradation and remodeling in development and disease, Cold Spring Harb Perspect Biol, 2011 (2011) a005058.
Luo, The role of matrix metalloproteinases in the morphogenesis of the cerebellar cortex, Cerebellum, 4 (2005) 239-245.
Kinney, et al., Engineering three-dimensional stem cell morphogenesis for the development of tissue models and scalable regenerative therapeutics, Ann Biomed Eng, 42 (2014) 352-367.
Maury, et al., Combinatorial analysis of developmental cues efficiently converts human pluripotent stem cells into multiple neuronal subtypes, Nat Biotechnol, 33 (2015) 89-96.
Mariani et al., FOXG1-dependent dysregulation of GABA/Glutamate neuron differentiation in Autism Spectrum Disorders, Cell, 162 (2015) 375-390.
Mertens, et al., Differential responses to lithium in hyperexcitable neurons from patients with bipolar disorder, Nature, 527 (2015) 95-99.
Moya, et al., Endogenous WNT signaling regulates hPSC-derived neural progenitor cell heterogeneity and specifies their regional identity, Stem Cell Reports, 3 (2014) 1015-1028.
Nicholas, et al., Functional maturation of hPSC-derived forebrain interneurons requires an extended timeline and mimics human neural development, Cell Stem Cell, 12 (2013) 573-586.
Nieweg, et al., Alzheimer's disease-related amyloid-beta induces synaptotoxicity in human iPS cell-derived neurons, Cell Death Dis, 6 (2015) e1709.
Nistor, et al., Derivation of high purity neuronal progenitors from human embryonic stem cells, PLoS One, 6 (2011) e20692.
Park, et al., Conversion of mouse fibroblasts into cardiomyocyte-like cells using small molecule treatments, Biomaterials, 54 (2015) 201-212.
Pasca, et al., Functional cortical neurons and astrocytes from human pluripotent stem cells in 3D culture, Nat Methods, 12 (2015) 671-678.
Przybyla & Voldman, Attenuation of extrinsic signaling reveals the importance of matrix remodeling on maintenance of embryonic stem cell self-renewal, Proc Natl Acad Sci U S A, 109 (2012) 835-840.
Schwartz, et al., Human pluripotent stem cell-derived neural constructs for predicting neural toxicity, Proc Natl Acad Sci U S A, 112 (2015) 12516-12521.
Suzuki & Vanderhaeghen, Is this a brain which I see before me? Modeling human neural development with pluripotent stem cells, Development, 142 (2015) 3138-3150.
Si-Tayeb, et al., Generation of human induced pluripotent stem cells by simple transient transfection of plasmid DNA encoding reprogramming factors, BMC Dev Biol, 10 (2010) 81.
Si-Tayeb, et al., Highly efficient generation of human hepatocyte-like cells from induced pluripotent stem cells, Hepatology, 51 (2010) 297-305.
Siller, et al., Small-molecule-driven hepatocyte differentiation of human pluripotent stem cells, Stem Cell Reports, 4 (2015) 939-952.
Sharma, et al., Genetic and epigenetic mechanisms contribute to motor neuron pathfinding. Nature. Aug. 3, 2000;406 (6795):515-9.
Stanton & Peng, Small-molecule modulators of the Sonic Hedgehog signaling pathway, Mol Biosyst, 6 (2010) 44-54.
Szymczak, et al., Effect of matrix metalloproteinases inhibition on the proliferation and differentiation of HUCB-NSCs cultured in the presence of adhesive substrates, Acta Neurobiol Exp (Wars), 70 (2010) 325-336.
Tasnim, et al., Cost-effective differentiation of hepatocyte-like cells from human pluripotent stem cells using small molecules, Biomaterials, 70 (2015) 115-125).
Tonti, et al., Neural stem cells at the crossroads: MMPs may tell the way, Int J Dev Biol, 53 (2009) 1-17.

* cited by examiner

THREE-DIMENSIONAL HUMAN STEM CELL-DERIVED CORTICAL SPHEROID MODEL

REFERENCE TO RELATED APPLICATIONS

This application claims priority to U.S. Provisional Patent Application Ser. No. 62/254,735, entitled "A Three Dimensional Human Stem Cell-Derived Cortical Spheroid Model", filed Nov. 13, 2015, the contents of which are hereby incorporated by reference into this disclosure.

GOVERNMENT SUPPORT STATEMENT

This invention was made with Government support under Grant Number 1342192 awarded by the National Science Foundation. The Government has certain rights in the invention.

REFERENCE TO AN ELECTRONIC SEQUENCE LISTING

The contents of the electronic sequence listing (Three Dimensional Human Stem Cell-Derived Cortical Spheroid Model; 3000 bytes; Creation: Apr. 17, 2019) is incorporated by reference in its entirety.

FIELD OF INVENTION

This invention relates to cellular models for research. More specifically, the present invention provides three dimensional models for investigating Alzheimer's disease and other neurodegenerative disorders and screening for therapeutics for Alzheimer's disease and other neurodegenerative disorders.

BACKGROUND OF THE INVENTION

Restricted access to human brain tissues limits the discovery of novel interventions and pharmacological treatments for one billion people with neurological disorders globally (World Health Organization, Neurological disorders affect 1 billion people: WHO Report, (World Health Org., 2007)).

Amyloid precursor protein (APP) proteolysis is fundamental for production of amyloid-b (Aβ) peptides implicated in Alzheimer's disease (AD) pathology (Golde, et al., (2000) Biochemical detection of Aβ isoforms: implications for pathogenesis, diagnosis, and treatment of Alzheimer's disease. Biochim Biophys Acta 1502, 172-187; Huse & Doms, (2000) Closing in on the amyloid cascade: recent insights into the cell biology of Alzheimer's disease. Mol Neurobiol 22, 81-98; Sambamurti, et al., (2002) Advances in the cellular and molecular biology of the 1-amyloid protein in Alzheimer's disease. Neuromolecular Med 1, 1-31; Funamoto, et al., (2004) Truncated carboxyl-terminal fragments of b-amyloid precursor protein are processed to amyloid β-proteins 40 and 42. Biochemistry 43, 13532-13540). APP proteolytic products arise from the actions of α-, β-, and γ-secretases. In the amyloidogenic pathway, Aβ peptides are produced via initial action of β-secretase (BACE) cleavage, which creates an Aβ-containing carboxylterminal fragment, β-CTF or C99 (Sinha & Lieberburg, (1999) Cellular mechanisms of β-amyloid production and secretion. Proc Natl Acad Sci USA 96, 11049-11053; Yan, et al., (1999) Membrane-anchored aspartyl protease with Alzheimer's disease beta-secretase activity. Nature 402, 533-537). This also generates an amino-terminal, soluble APPb (sAPPb) fragment, which is released extracellularly. Intracellularly, β-CTF is then cleaved by a multiprotein γ-secretase complex that results in generation of the Aβ peptide and a smaller γ-CTF, also known as C57 (Steiner, et al., (1999) Proteolytic processing and degradation of Alzheimer's disease relevant proteins. Biochem Soc Trans 27, 234-242). Conversely, in the anti-amyloidogenic pathway, APP is first cleaved at the asecretase site, by the putative α-secretase (a disintegrin and metallopeptidase domain-10, ADAM10), which results in the release of amino-terminal soluble APPa (sAPPα) and the generation of α-CTF or C83 (Hooper & Turner, (2002). The search for α-secretase and its potential as a therapeutic approach to Alzheimer s disease. Curr Med Chem 9, 1107-1119).

Over the past decade, there has been intense focus on investigating the processes of APP proteolysis and Aβ production as possible targets for AD therapy (Hardy & Selkoe, (2002) The amyloid hypothesis of Alzheimer's disease: progress and problems on the road to therapeutics. Science 297, 353-356). Various models have been developed and proposed for their ability to accurately replicate neuronal structures and responses to these pathological events. However, the majority of the models are two dimensional and lack accurate modeling of neuronal structures and connections.

Recapitulating neural development and pathology in a three-dimensional (3-D) brain tissue model is critical for studying Alzheimer's disease (AD) progression and screening therapeutic drugs. Currently, there is no good treatment to Alzheimer's disease and the on-set of Alzheimer's disease is unclear. Recently, in vitro 3-D neural cell cultures were used to mimic brain tissue and showed high sensitivity to amyloid-β (Aβ)-induced toxicity. Compared to 2-D culture models, 3-D neural culture models promote neuronal maturation and better recapitulate Alzheimer's disease. However, the previous 3-D models were established using adult human neural stem cells and restricted access to human brain tissues limits the distribution of such models. Moreover, AD progression takes years. So, novel in vitro brain models are urgently needed for better understanding of changes in central nervous systems due to AD in a short time frame.

Human induced pluripotent stem cells (hiPSCs) emerge recently as alternative sources of primary brain cells to establish AD models in vitro. From this technology, the neural induction of hiPSCs is affected by embryonic-like extracellular matrices (eECMs). A suspension bioreactor was used to enhance the diffusion inside the spheroids, which enables complex cortical neural tissue development in vitro. The derived cortical spheroids have cortical layer-specific structure and synaptic activities. The 3-D cortical spheroids derived from hiPSCs of specific patients can retain their genetic background and thus represent patient-specific in vitro models for studying AD progression and identifying therapeutic target(s). The cellular response of the model was tested on amyloid beta ($A\beta_{1-42}$) oligomer-induced neurotoxicity and evaluated the response in the presence of Wnt activator. In some variations of the cellular model, the cells are transformed using motor neuron genes, thereby allowing for modeling of motor neurons (Arlotta, et al., Neuronal subtype-specific genes that control corticospinal motor neuron development in vivo. Neuron. 2005 Jan. 20; 45(2):207-21; Hedlund, et al., Global gene expression profiling of somatic motor neuron populations with different vulnerability identify molecules and pathways of degeneration and protection. Brain. 2010 August; 133(Pr 8):2313-30; Sharma, et al., Genetic and epigenetic mechanisms contribute to motor neuron pathfinding. Nature. 2000 Aug. 3; 406(6795): 515-9).

Human induced pluripotent stem cells (hiPSCs) can generate allogeneic or patient-specific neural cells, cortical tissues, and even mini-brains (i.e., brain organoids), which are physiologically relevant to model neural diseases and to identify pharmacological therapeutics (Chambers, et al., Build-a-brain, Cell Stem Cell, 13 (2013) 377-378; Kinney, et al., Engineering three-dimensional stem cell morphogenesis for the development of tissue models and scalable regenerative therapeutics, Ann Biomed Eng, 42 (2014) 352-367; Pasca, et al., Functional cortical neurons and astrocytes from human pluripotent stem cells in 3D culture, Nat Methods, 12 (2015) 671-678; Dimos, et al., Induced pluripotent stem cells generated from patients with ALS can be differentiated into motor neurons, Science, 321 (2008) 1218-1221; Suzuki & Vanderhaeghen, Is this a brain which I see before me? Modeling human neural development with pluripotent stem cells, Development, 142 (2015) 3138-3150; Schwartz, et al., Human pluripotent stem cell-derived neural constructs for predicting neural toxicity, Proc Natl Acad Sci USA, 112 (2015) 12516-12521). While some disease progressions (e.g., amyloid-β plaques) may take years, in vitro neural models derived from hiPSCs can be used to probe disease on-set and development in a shortened time frame (Kondo, et al., Modeling Alzheimer's disease with iPSCs reveals stress phenotypes associated with intracellular Abeta and differential drug responsiveness, Cell Stem Cell, 12 (2013) 487-496). Another advantage of in vitro models derived from hiPSCs is the ability to generate specific neuronal subtypes, which are known to exhibit differential susceptibility to disease-specific molecules (Vazin, et al., Efficient derivation of cortical glutamatergic neurons from human pluripotent stem cells: a model system to study neurotoxicity in Alzheimer's disease, Neurobiol Dis, 62 (2014) 62-72; Mertens, et al., Differential responses to lithium in hyperexcitable neurons from patients with bipolar disorder, Nature, 527 (2015) 95-99). For example, cortical neurons derived from hiPSCs have been used to screen anti-amyloid β (Aβ) drugs and to evaluate Aβ-induced toxicity (Vazin, et al., Efficient derivation of cortical glutamatergic neurons from human pluripotent stem cells: a model system to study neurotoxicity in Alzheimer's disease, Neurobiol Dis, 62 (2014) 62-72; Yahata, et al., Anti-Abeta drug screening platform using human iPS cell-derived neurons for the treatment of Alzheimer's disease, PLoS One, 6 (2011) e25788; Nieweg, et al., Alzheimer's disease-related amyloid-beta induces synaptotoxicity in human iPS cell-derived neurons, Cell Death Dis, 6 (2015) e1709). Moreover, hiPSC-derived motor neurons have been derived to model a variety of motor neuron diseases, such as amyotrophic lateral sclerosis (ALS) (Dimos, et al., Induced pluripotent stem cells generated from patients with ALS can be differentiated into motor neurons, Science, 321 (2008) 1218-1221; Di Giorgio, et al., Human embryonic stem cell-derived motor neurons are sensitive to the toxic effect of glial cells carrying an ALS-causing mutation, Cell Stem Cell, 3 (2008) 637-648).

Generating multiple neuronal subtypes from hiPSCs with a tunable differentiation protocol to delineate differential cellular responses is in a critical medical need (Schwartz, et al., Human pluripotent stem cell-derived neural constructs for predicting neural toxicity, Proc Natl Acad Sci USA, 112 (2015) 12516-12521; Mertens, et al., Differential responses to lithium in hyperexcitable neurons from patients with bipolar disorder, Nature, 527 (2015) 95-99; Maury, et al., Combinatorial analysis of developmental cues efficiently converts human pluripotent stem cells into multiple neuronal subtypes, Nat Biotechnol, 33 (2015) 89-96; Imaizumi, et al., Controlling the regional identity of hPSC-derived neurons to uncover neuronal subtype specificity of neurological disease phenotypes, Stem Cell Reports, 5 (2015) 1010-1022). In particular, 3-D neural cultures provide a good platform to generate region-specific neuronal subtypes or human brain-like tissues (e.g., microtissues or organoids) (Pasca, et al., Functional cortical neurons and astrocytes from human pluripotent stem cells in 3D culture, Nat Methods, 12 (2015) 671-678; Schwartz, et al., Human pluripotent stem cell-derived neural constructs for predicting neural toxicity, Proc Natl Acad Sci USA, 112 (2015) 12516-12521). Compared to 2-D cultures, 3-D cultures promote neuronal cell specification and maturation, therefore better recapitulating disease pathology or predicting neural toxicity (Schwartz, et al., Human pluripotent stem cell-derived neural constructs for predicting neural toxicity, Proc Natl Acad Sci USA, 112 (2015) 12516-12521; Choi, et al., A three-dimensional human neural cell culture model of Alzheimer's disease, Nature, 515 (2014) 274-278; Zhang, et al., A 3D Alzheimer's disease culture model and the induction of P21-activated kinase mediated sensing in iPSC derived neurons, Biomaterials, 35 (2014) 1420-1428; Choi, et al., Size-controllable networked neurospheres as a 3D neuronal tissue model for Alzheimer's disease studies, Biomaterials, 34 (2013) 2938-2946). There are two types of 3-D cultures: scaffold-based and scaffold-free. Scaffold-based 3-D cultures use natural or synthetic scaffolds to create 3-D template that allow the cells adhere, proliferate, and differentiate. Scaffold-free 3-D cultures are based on the self-organization ability of the stem cells. The cells spontaneously organize into multicellular aggregates, spheroids, or organoids (Pasca, et al., Functional cortical neurons and astrocytes from human pluripotent stem cells in 3D culture, Nat Methods, 12 (2015) 671-678). The embryoid body (EB)-based neural differentiation is a major approach to promote the self-organization of human pluripotent stem cells (hPSCs) into complex brain-like tissue structures (Pasca, et al., Functional cortical neurons and astrocytes from human pluripotent stem cells in 3D culture, Nat Methods, 12 (2015) 671-678; Eiraku, et al., Self-organized formation of polarized cortical tissues from ESCs and its active manipulation by extrinsic signals, Cell Stem Cell, 3 (2008) 519-532; Lancaster, et al., Cerebral organoids model human brain development and microcephaly, Nature, 501 (2013) 373-379), besides the scaffold-based approaches (Hosseinkhani, et al., Engineering three-dimensional collagen-IKVAV matrix to mimic neural microenvironment, ACS Chem Neurosci, 4 (2013) 1229-1235; Abbasi, et al., Influence of oriented nanofibrous PCL scaffolds on quantitative gene expression during neural differentiation of mouse embryonic stem cells, J Biomed Mater Res A, 104 (2016) 155-164). However, functional differentiation into specific neural subtypes from hPSCs has been challenging (Nicholas, et al., Functional maturation of hPSC-derived forebrain interneurons requires an extended timeline and mimics human neural development, Cell Stem Cell, 12 (2013) 573-586), largely because the capacity of different signaling factors that regulate 3-D neural tissue patterning in vitro has not yet been fully understood (Maury, et al., Combinatorial analysis of developmental cues efficiently converts human pluripotent stem cells into multiple neuronal subtypes, Nat Biotechnol, 33 (2015) 89-96).

In neural patterning of brain tissues, i.e., the process through which neural progenitors acquire brain regional identity, activation of sonic hedgehog (SHH) signaling induces ventral (V) identity of the developing neural ectoderm while SHH inhibition generates dorsal (D) telencephalic progenitors (i.e., affects D-V patterning) (van den Ameele, et al., Thinking out of the dish: what to learn about cortical development using pluripotent stem cells, Trends Neurosci, 37 (2014) 334-342; Vazin, et al., The effect of multivalent Sonic hedgehog on differentiation of human embryonic stem cells into dopaminergic and GABAergic neurons, Biomaterials, 35 (2014) 941-948). Thus, differential levels of SHH signaling, in combination with other signaling such as Wnt and retinoic acid, influence neural regional specification of hPSCs into forebrain cortical tissues, midbrain tissues, and hindbrain/spinal cord tissues (Suzuki & Vanderhaeghen, Is this a brain which I see before me? Modeling human neural development with pluripotent stem cells, Development, 142 (2015) 3138-3150). In biomaterials research, one attractive approach is to modulate hPSC fate decisions and differentiations using small molecules that regulate signaling pathways through defined mechanisms (Siller, et al., Small-molecule-driven hepatocyte differentiation of human pluripotent stem cells, Stem Cell Reports, 4 (2015) 939-952; Park, et al., Conversion of mouse fibroblasts into cardiomyocyte-like cells using small molecule treatments, Biomaterials, 54 (2015) 201-212; Jiang, et al., Generation of cardiac spheres from primate pluripotent stem cells in a small molecule-based 3D system, Biomaterials, 65 (2015) 103-114; Tasnim, et al., Cost-effective differentiation of hepatocyte-like cells from human pluripotent stem cells using small molecules, Biomaterials, 70 (2015) 115-125). Specifically, small molecules in SHH signaling (Vazin, et al., The effect of multivalent Sonic hedgehog on differentiation of human embryonic stem cells into dopaminergic and GABAergic neurons, Biomaterials, 35 (2014) 941-948; Stanton & Peng, Small-molecule modulators of the Sonic Hedgehog signaling pathway, Mol Biosyst, 6 (2010) 44-54) have been demonstrated previously to facilitate the generation of some specific neural types from hPSCs (Hu & Zhang, Differentiation of spinal motor neurons from pluripotent human stem cells, Nat Protoc, 4 (2009) 1295-1304). However, the capability of SHH-related small molecules to tune different neuronal subtypes in 3-D differentiation from hiPSCs has not been fully investigated.

Therefore, there is an unmet need for three dimensional neuronal cell systems that can model neuronal interactions and responses to various environmental conditions, including particles and conditions that can result in neuronal damage and neuronal degeneration.

SUMMARY OF THE INVENTION

Human iPSC cells (hiPSCs) were patterned in three dimensions using small molecules that affect sonic hedgehog signaling along with other factors (e.g., fibroblast growth factor-2, retinoic acid, and Wnt signaling) to generate different neuronal subtypes (cortical glutamatergic neurons and motor neurons). The model comprises human iPSK3 cells or SY-UBH cells that were induced to a neuronal phenotype through exposure to a rho-associated kinase pathway inhibitor. Without being bound to a specific inhibitor, exemplary rho-associated kinase pathway inhibitors are (+)-(R)-trans-4-(1-aminoethyl)-N-(4-pyridyl)cyclohexanecarboxamide dihydrochloride (Y27632). The rho-associated kinase pathway inhibitor is used at a concentration of about 10 µM. Non-limiting examples include 8 µM, 8.25 µM, 8.5 µM, 8.75 µM, 9.0 µM, 9.25 µM, 9.5 µM, 9.75 µM, and 10.0 µM. The concentration is optionally measured in a medium begin applied to the cells, or locally around the cell. The cells were exposed to the rho-associated kinase pathway inhibitor for about 24 hours. Non-limiting examples include 20.4 hours, 20.5 hours, 20.75 hours, 21.0 hours, 21.25 hours, 21.5 hours, 21.75 hours, 22.0 hours, 22.25 hours, 22.5 hours, 22.75 hours, 23.0 hours, 23.2 hours, 23.25 hours, 23.3 hours, 23.4 hours, 23.5 hours, 23.6 hours, 23.7 hours, 23.75 hours, 23.8 hours, 23.9 hours, 24.0 hours, 24.1 hours, 24.2 hours, 24.25 hours, 24.3 hours, 24.4 hours, 24.5 hours, 24.6 hours, 24.7 hours, 24.8 hours, 24.9 hours, 25.0 hours, 25.1 hours, 25.2 hours, 25.25 hours, 25.5 hours, 25.75 hours, 26.0 hours, 26.25 hours, 26.5 hours, 26.75 hours, 27.0 hours, 27.25 hours, 27.5 hours, and 27.6 hours.

After exposure to the RAP kinase inhibitor, the cells were exposed to one or more SMAD pathway inhibitors. Non-limiting examples of the inhibitors are 4-(4-(benzo[d][1,3]dioxol-5-yl)-5-(pyridin-2-yl)-1H-imidazol-2-yl)benzamide (SB431542), 6-[2-tert-butyl-5-(6-methylpyridin-2-yl)-1H-imidazol-4-yl]quinoxaline (SB525334), 4-[6-[4-(1-piperazyl)phenyl]pyrazol[1,5-a]pyrimidin-3-yl]-quinoline (LDN193189), noggin, or a combination thereof. The SMAD pathway inhibitors are optionally used at between 5 µM and 15 µM for SB431542 and/or SB525334, and between 0.1 µM and 0.5 µM 100 nM for LDN193189 and/or noggin. For example, SB431542 and/or SB525334 is used at about 6 µM, about 6.5 µM, about 6.75 µM, about 7.0 µM, about 7.25 µM, about 7.5 µM, about 7.75 µM, about 8.0 µM, about 8.25 µM, about 8.5 µM, about 8.75 µM, about 9.0 µM, about 9.25 µM, about 9.5 µM, about 9.75 µM, about 10.0 µM, about 10.25 µM, about 10.5 µM, about 10.75 µM, about 11.0 µM, about 11.25 µM, about 11.5 µM, about 11.75 µM, about 12.0 µM, about 12.25 µM, about 12.5 µM, about 12.75 µM, about 13.0 µM, about 13.25 µM, about 13.5 µM, about 13.75 µM, about 14.0 µM, about 14.25 µM, about 14.5 µM, or about 14.75 µM. Specific concentration that are useful include 5 µM, 5.25 µM, 5.5 µM, 5.75 µM, 6.0 µM, 6.25 µM, 6.5 µM, 6.75 µM, 7.0 µM, 7.25 µM, 7.5 µM, 7.75 µM, 8.0 µM, 8.25 µM, 8.5 µM, 8.75 µM, 9.0 µM, 9.25 µM, 9.5 µM, 9.75 µM, 10 µM, 10.25 µM, 10.5 µM, 10.75 µM, 11.0 µM, 11.25 µM, 11.5 µM, 11.75 µM, 12.0 µM, 12.25 µM, 12.5 µM, 12.75 µM, 13.0 µM, 13.25 µM, 13.5 µM, 13.75 µM, 14.0 µM, 14.25 µM, 14.5 µM, 14.75 µM, and 15.0 µM. LDN193189 and/or noggin have been found useful at about 0.1 µM and 0.5 µM. For example, LDN193189 and/or noggin can be used at about 0.1 µM, about 0.15 µM, about 0.2 µM, about 0.25 µM, about 0.3 µM, about 0.35 µM, about 0.4 µM, about 0.45 µM, and about 0.5 µM, or at a specific concentration, such as 0.1 µM, 0.125 µM, 0.15 µM, 0.175 µM, 0.2 µM, 0.25 µM, 0.3 µM, 0.35 µM, 0.4 µM, 0.45 µM, or 0.5 µM. For example, SB431542 has been found particularly useful at 10 µM, while LDN193189 found particularly useful at 100 nM. The concentration is optionally measured in a medium begin applied to the cells, or locally around the cell. The cells were exposed to the SMAD inhibitor for about 7 days. Non-limiting exemplary times are 143.0 hours, 143.5 hours, 144.0 hours, 144.5 hours, 145.0 hours, 145.5 hours, 146.0 hours, 146.5 hours, 147.0 hours, 147.5 hours, 148.0 hours, 148.5 hours, 149.0 hours, 149.5 hours, 150.0 hours, 150.5 hours, 151.0 hours, 151.5 hours, 152.0 hours, 152.5 hours, 153.0 hours, 153.5 hours, 154.0 hours, 154.5 hours, 155.0 hours, 155.5 hours, 156.0 hours, 156.5 hours, 157.0 hours, 157.5 hours, 158.0 hours, 158.5 hours, 159.0 hours, 159.5 hours, 160.0 hours, 160.5 hours, 161.0 hours, 161.5 hours, 162.0 hours, 162.5 hours, 163.0 hours, 163.5 hours, 164.0 hours, 164.5 hours, 165.0 hours, 165.5 hours, 166.0 hours, 166.5 hours, 167.0 hours, 167.5 hours, 168.0 hours, 168.5 hours, 169.0 hours, 169.5 hours, 170.0 hours, 170.5 hours, 171.0 hours, 171.5 hours, 172.0 hours, 172.5 hours, 173.0 hours, 173.5 hours, 174.0 hours, 174.5 hours, 175.0 hours, 175.5 hours, 176.0 hours, 176.5 hours, 177.0 hours, 177.5 hours, 178.0 hours, 178.5 hours, 179.0 hours, 179.5 hours, 180.0 hours, 180.5 hours, 181.0 hours, 181.5 hours, 182.0 hours, 182.5 hours, 183.0 hours, 183.5 hours, 184.0 hours, 184.5 hours, 185.0 hours, 186.0 hours, 186.5 hours, 187.0 hours, 187.5 hours, 188.0 hours, 188.5 hours, 189.0 hours, 190.0 hours, 190.5 hours, 191.0 hours, 191.5 hours, 191.75 hours, 192.0 hours, 192.25 hours, 192.5 hours, 193.0 hours, and 193.5 hours.

The cells were then exposed to at least one sonic hedgehog signaling inhibitor; Non-limiting examples of the at least one sonic hedgehog signaling (SHH) inhibitor are cyclopamine, purmorphamine, jervine, and zerumbone. In some instances, it may be useful to use more than one SHH inhibitor. The at least one sonic hedgehog signaling inhibitor is optionally used at a concentration of from 0.3 µM to 1.5 µM. For example, the SHH inhibitor can be used at about 0.4 µM, about 0.5 µM, about 0.6 µM, about 0.7 µM, about 0.8 µM, about 0.9 µM, about 1.0 µM, about 1.1 µM, about 1.2 µM, about 1.3 µM, about 1.4 µM, or at a specific concentration, such as 0.3 µM, 0.4 µM, 0.5 µM, 0.6 µM, 0.7 µM, 0.8 µM, 0.9 µM, 1.0 µM, 1.1 µM, 1.2 µM, 1.3 µM, 1.4 µM, or 1.5 µM. The concentration is optionally measured in a medium begin applied to the cells, or locally around the cell.

The cells were then transferred to a basement membrane extract, forming cortical layer-specific structures.

The models disclosed herein can advance the understanding of hiPSC self-organization and neural tissue development, and provide a transformative approach to establish 3-D neural models for neurological disease modeling (e.g., Alzheimer's disease, ALS, etc.), drug discovery, and possibly cell therapy.

The model allows for modeling of differential cellular responses of different hiPSC-derived neuronal subtypes to the biomolecules that affect neurotoxicity and/or neurogenesis and model various neurodegenerative diseases by altering the culturing conditions or adding a neurodegenerative-inducing agent. For example, ischemia can be modeled by reducing or removing oxygen from the culturing conditions or subjecting the cellular model to oxygen-glucose deprivation (Newcomb-Fernandez, et al., Concurrent assessment of calpain and caspase-3 activation after oxygen-glucose deprivation in primary septo-hippocampal cultures. J Cereb Blood Flow Metab. 2001 November; 21(11):1281-94). Alzheimer's disease can be modeled by introducing pathogenic Aβ protein, such as tau, $A\beta_{1-40}$ or $A\beta_{1-42}$, Parkinson's disease can be modeled by introducing pathogenic alpha-synuclein, such as alpha-synuclein-ubiquitin complexes, Huntington's disease can be modeled by introducing pathogenic mutant Huntingtin protein, HIV associated dementia or HIV nephropathy can be modeled by introducing pathogenic HIV particles, such as Tat and GP41, GP120, GP160 (Nath, Human immunodeficiency virus (HIV) proteins in neuropathogenesis of HIV dementia. J Infect Dis. 2002 zDec 1; 186 Suppl 2:S193-8; Kaul, HIV-1 associated dementia update on pathological mechanisms and therapeutic approaches. Curr Opin Neurol. 2009 June; 22(3):315-20). Other neurodegenerative diseases include viral encephalitis from direct infection, such as herpes simplex virus, rabies virus, poliovirus, and JC virus (Nath, Human immunodeficiency virus (HIV) proteins in neuropathogenesis of HIV dementia. J Infect Dis. 2002 Dec. 1; 186 Suppl 2:S193-8) which can be modeled by introducing the virus to the inventive cellular model, neurotoxin-based neurodegenerative diseases through introduction of the neurotoxin, prion spongiform encephalopathy can be induced by introducing mutant prion proteins. Other diseases that may be modeled include multiple sclerosis (Buchmeier, et al., Vial-induced neurodegenerative disease. Curr Opin Microbiol. 1999 August; 2(4):398-402) and retrovirus-induced spongiform neurodegeneration (Li, et al., Retrovirus-induced spongiform neurodegeneration is mediated by unique central nervous system viral targeting and expression of ENV alone. J Virol. 2011 March; 85(5):2060-78).

The model is also used for methods of screening for compounds that treat or prophylactically treat a neurodegenerative disease or testing compounds that treat or prophylactically treat a neurodegenerative disease. Using the model described above, a xenobiotic candidate is screened or tested by performing either pre-treatment screening or testing, or post-insult screening or testing. Pre-treatment screening or testing is performed by introducing the xenobiotic candidate to the cellular model (test model) at a proposed therapeutically effective amount or at varying assigned amounts to determine a therapeutically effective amount, and introducing a null treatment to a negative control. The test model and negative control model are then both exposed to a neurodegenerative agent. The post-insult screening or testing is performed by exposing a test cellular model and a negative control model to a neurodegenerative agent. The xenobiotic candidate is then introduced to the test cellular model at a proposed therapeutically effective amount or at varying assigned amounts to determine a therapeutically effective amount. A null treatment is introduced to the negative control. Null treatments can be water, medium, or the pharmaceutical carrier without the xenobiotic candidate. The effectiveness of the candidate drug to remediate, treat, or prevent a neurological disease or the therapeutically effective amount based on the response of the cellular model to the neurodegenerative agent is then determined by comparing the effects of the test cellular model or models or the negative control model. For example the negative control can be compared to the test model using statistical analysis as known in the art.

The neurodegenerative agent is optionally one discussed above or a neuronal insult, reduction or removal of oxygen from the culturing conditions, introduction of oxygen-glucose deprivation, introduction of amyloid-forming protein, introduction of pathogenic Aβ protein, introduction of tau, introduction of $A\beta_{1-40}$, introduction of $A\beta_{1-42}$, introduction of pathogenic alpha-synuclein, introduction of alpha-synuclein-ubiquitin complex, introduction of pathogenic mutant Huntingtin protein, introduction of pathogenic HIV particles, introduction of Tat, introduction of GP41, introduction of GP120, introduction of GP160, introduction of a combination of the HIV particles, introduction of neuron-infecting virus, introduction of herpes simplex virus, introduction of rabies virus, introduction of poliovirus, introduction of JC virus introduction of a neurotoxin, introduction of mutant prion protein, or introduction of neuron-infecting retrovirus.

The method of preparing a cellular model to replicate neuronal response is also provided herein. Human iPSK3 cells are placed in a medium containing rho-associated kinase pathway inhibitor, as outlaid above. After exposure to the RAP kinase inhibitor, the cells are exposed to SMAD pathway inhibitors, as disclosed above, followed by exposure to at least one sonic hedgehog signaling inhibitor. Useful inhibitors, concentrations and times are disclosed above. The cells are then transferred to a basement membrane extract and allowed to form integrated cortical layer-specific structures. In some variation of the invention, the human iPSK3 cells are introduced into a spinner bioreactor, in fluid communication with a cell medium flow device. A first medium is flowed into the reactor, containing the SMAD pathway inhibitor, followed by a second medium containing the sonic hedgehog signaling inhibitor. The flow of the cell medium is optionally at 3-15 dyne/cm$^2$. The human iPSK3 cells are allowed to form at least one spheroid structure, wherein the human iPSK3 cells form cortical layer-specific structure and synaptic activities. Where the bioreactor is used, the human iPSK3 cells are optionally introduced at a density of 4.0-4.5×10$^5$ cells/mL.

BRIEF DESCRIPTION OF THE DRAWINGS

For a fuller understanding of the invention, reference should be made to the following detailed description, taken in connection with the accompanying drawings, in which.

represents cells treated with LDN methods, and the light gray line (center) represents cells treated with RA methods.

Figure 17:
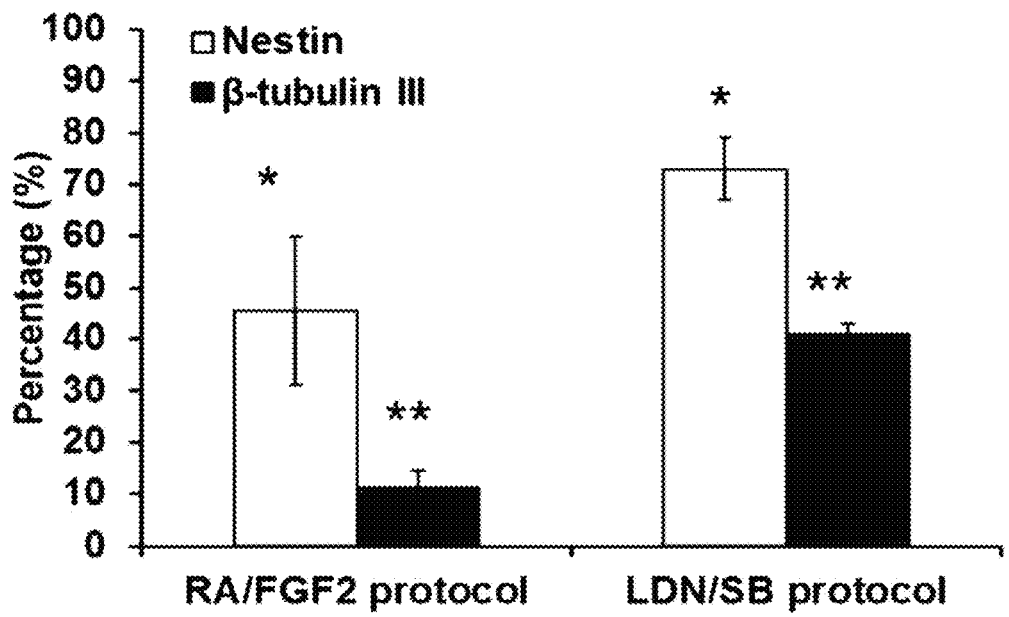

FIG. 17 is a graph showing neural marker (Nestin and β-tubulin III) expression at day 15 of differentiation in suspension quantified by flow cytometry. * and ** indicate $p<0.05$.

Figure 18A:
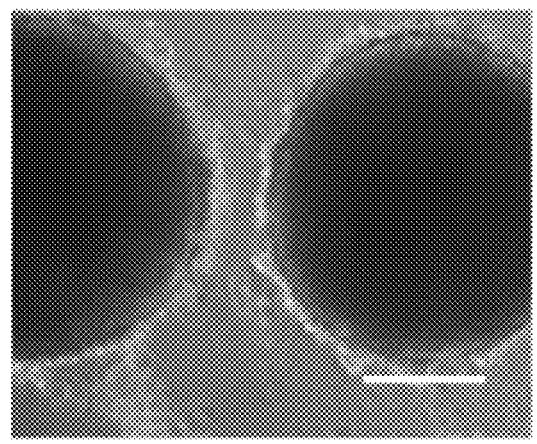

FIG. 18A is a phase contrast image showing cells from day 15 NPC spheres. Scale bar: 200 μm.

Figure 18B:
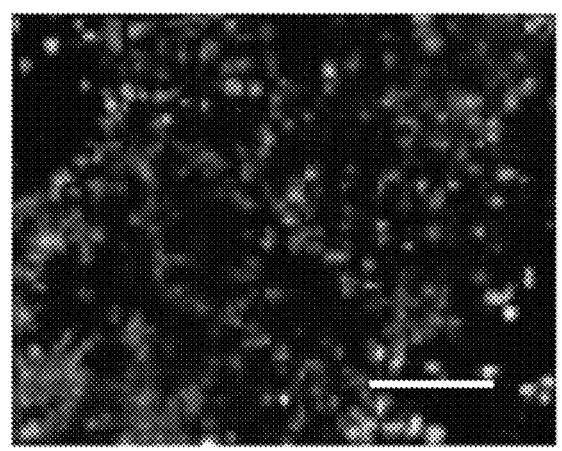

FIG. 18B is a fluorescent image showing cells from day 15 NPC spheres. Cells were stained for Nestin. Scale bar: 100 μm.

Figure 18C:
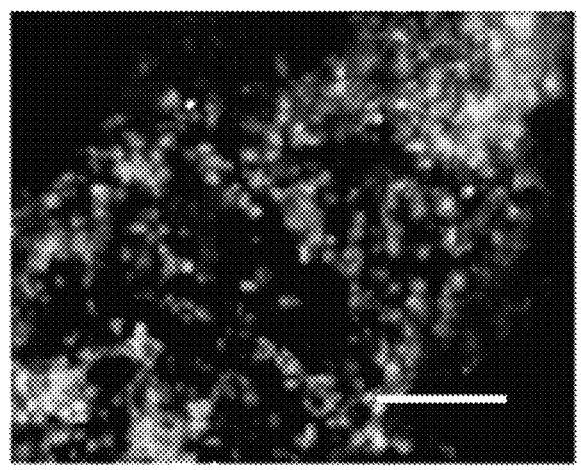

FIG. 18C is a fluorescent image showing cells from day 15 NPC spheres. Cells were stained for Pax-6. Scale bar: 100 μm.

Figure 18D:
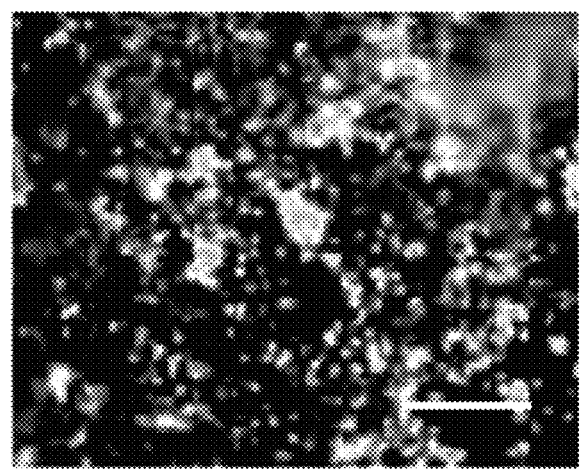

FIG. 18D is a fluorescent image showing cells from day 15 NPC spheres. Cells were stained for Hoechst. Scale bar: 100 μm.

Figure 19A:
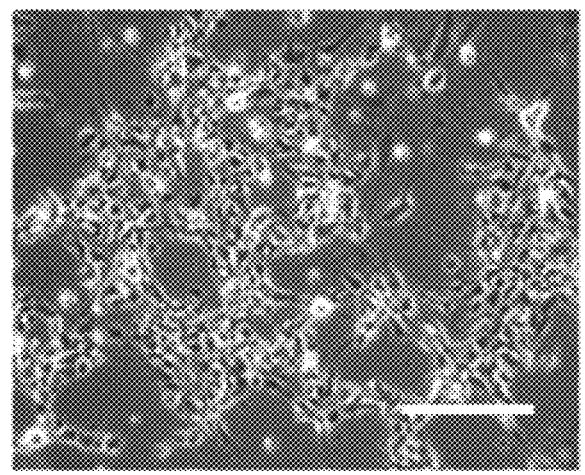

FIG. 19A is a phase contrast image showing cells from day 15 NPC spheres, replated for 3 days. Neural outgrowth was generated from replated spheres. Scale bar: 200 μm.

Figure 19B:
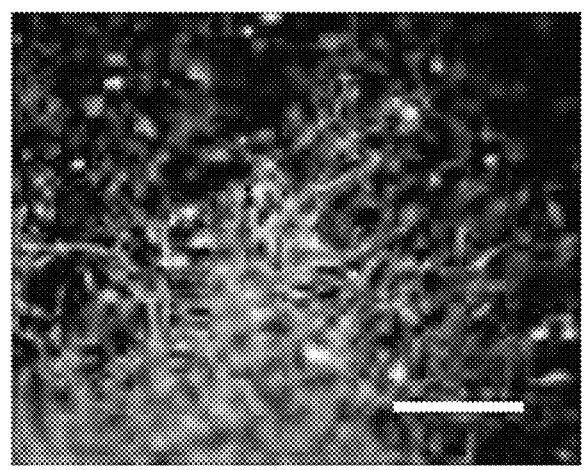

FIG. 19B is a fluorescent image showing cells from day 15 NPC spheres. Neural outgrowth was generated from replated spheres. Cells were stained for Nestin. Scale bar: 100 μm.

Figure 19C:
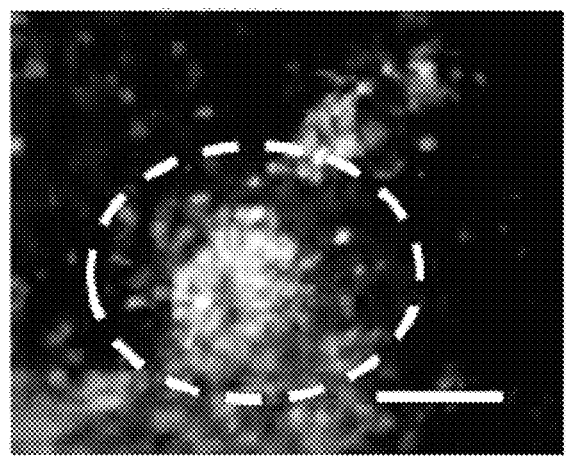

FIG. 19C is a fluorescent image showing cells from day 15 NPC spheres. Cells were stained for Pax-6. Neural outgrowth was generated from replated spheres. The circle shows the rosette morphology of the cells. Scale bar: 100 μm.

Figure 19D:
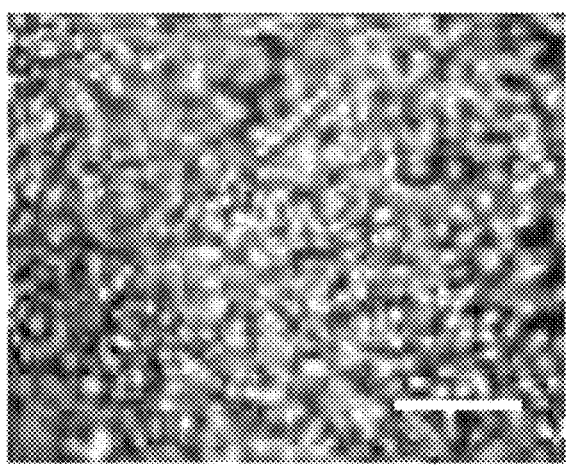

FIG. 19D is a fluorescent image showing cells from day 15 NPC spheres. Cells were stained for Hoechst. Neural outgrowth was generated from replated spheres. Scale bar: 100 μm.

Figure 20A:
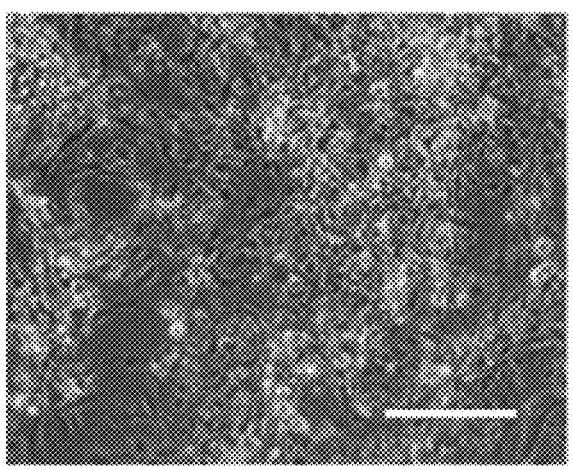

FIG. 20A is a phase contrast image showing cells from day 15 NPC spheres. The cells were replated and grown for an additional 15 days, and imaged. Neural outgrowth was generated from replated spheres. Scale bar: 200 μm.

Figure 20B:
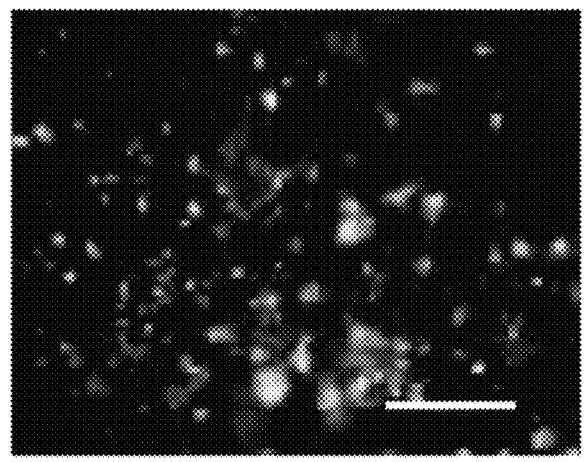

FIG. 20B is a fluorescent image showing cells from day 15 NPC spheres. The cells were replated and grown for an additional 15 days, and stained for Lim3. Neural outgrowth was generated from replated spheres. Scale bar: 100 μm.

Figure 20C:
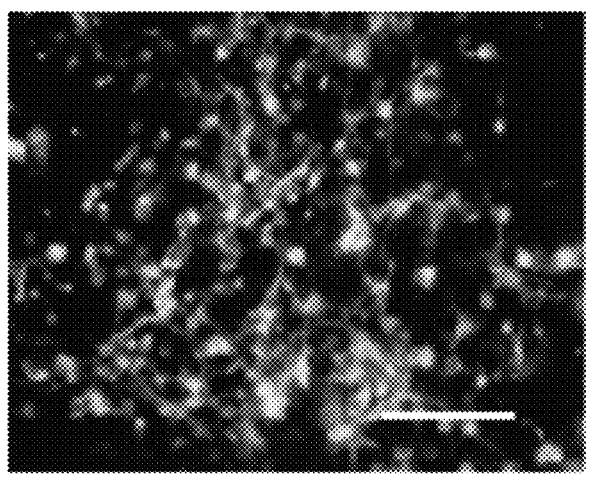

FIG. 20C is a fluorescent image showing cells from day 15 NPC spheres. The cells were replated and grown for an additional 15 days, and stained for β-tubulin III. Neural outgrowth was generated from replated spheres. Scale bar: 100 μm.

Figure 20D:
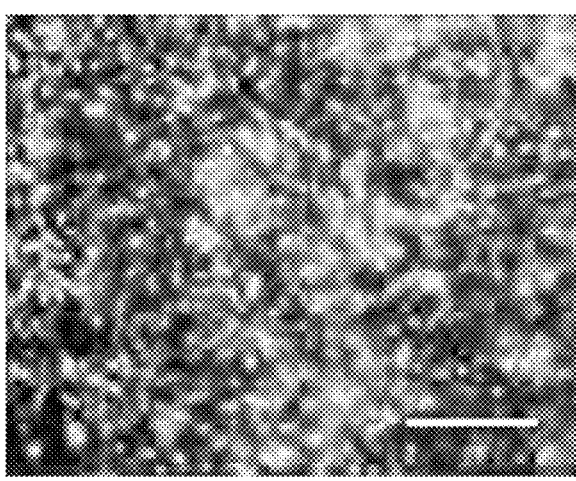

FIG. 20D is a fluorescent image showing cells from day 15 NPC spheres. The cells were replated and grown for an additional 15 days, and stained for Hoechst. Neural outgrowth was generated from replated spheres. Scale bar: 100 μm.

Figure 21A:
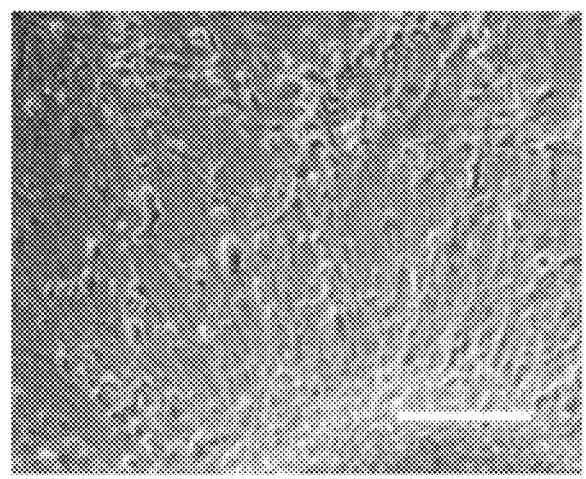

FIG. 21A is a phase contrast image showing cells from day 15 NPC spheres. The cells were replated and grown for an additional 15 days, and imaged. Neural outgrowth was generated from replated spheres. Scale bar: 200 μm.

Figure 21B:
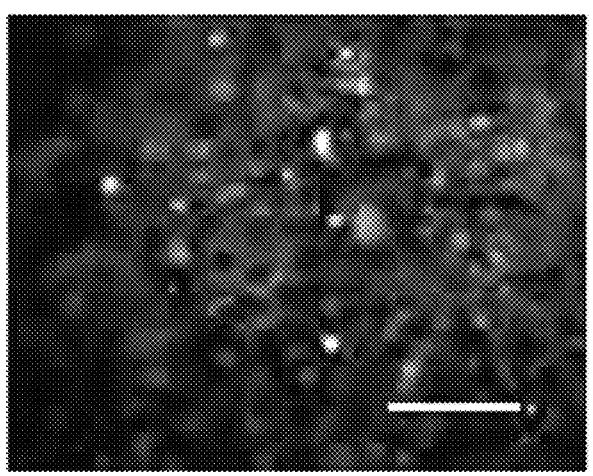

FIG. 21B is a fluorescent image showing cells from day 15 NPC spheres. The cells were replated and grown for an additional 15 days, and stained for glutamate. Neural outgrowth was generated from replated spheres. Scale bar: 100 μm.

Figure 21C:
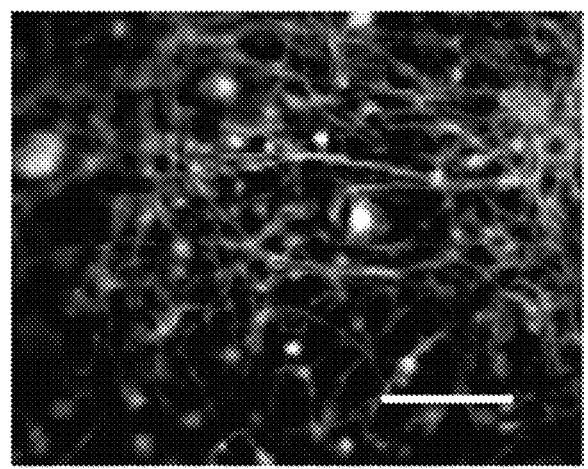

FIG. 21C is a fluorescent image showing cells from day 15 NPC spheres. The cells were replated and grown for an additional 15 days, and stained for β-tubulin III. Neural outgrowth was generated from replated spheres. Scale bar: 100 μm.

Figure 21D:
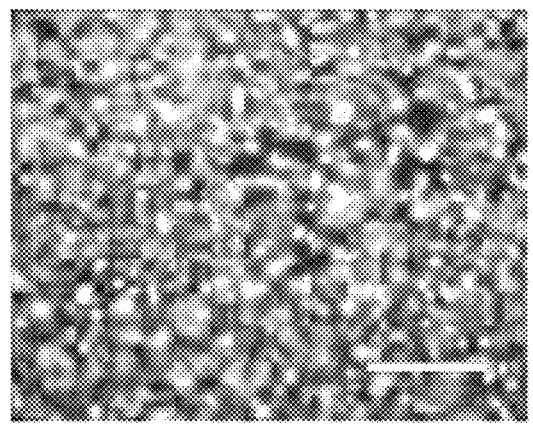

FIG. 21D is a fluorescent image showing cells from day 15 NPC spheres. The cells were replated and grown for an additional 15 days, and stained for Hoechst. Neural outgrowth was generated from replated spheres. Scale bar: 100 μm.

Figure 22:
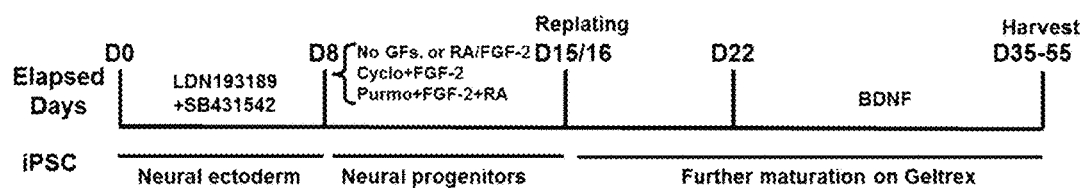

FIG. 22 is an illustration of different neural patterning conditions during day 8-15 (or 16).

Figure 23A:
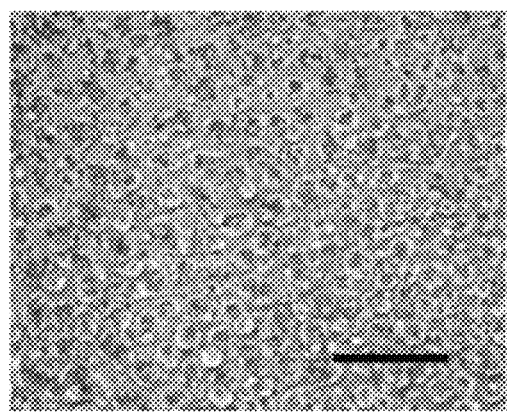

FIG. 23A is a phase contrast image showing cells from NPC spheres during neural patterning of the human iPSCs. The morphology of the cells at day 1 was captured. Scale bar: 200 μm.

Figure 23B:
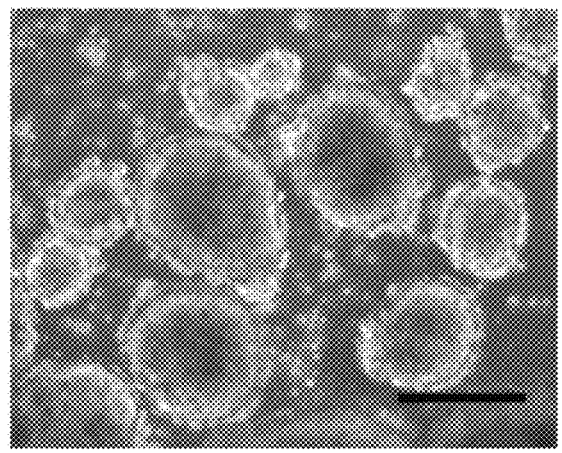

FIG. 23B is a phase contrast image showing cells from NPC spheres during neural patterning of the human iPSCs. The morphology of the cells at day 5 was captured. Scale bar: 200 μm.

Figure 23C:
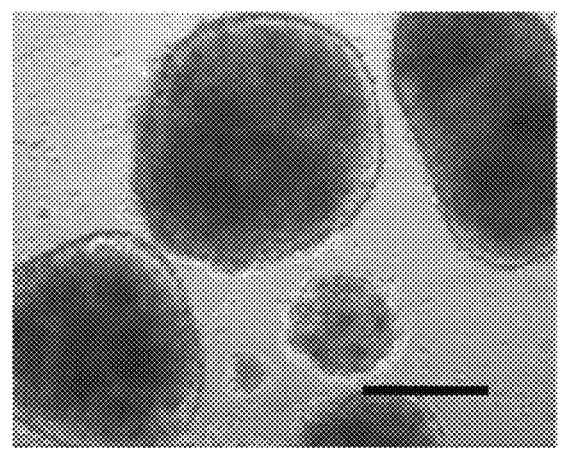

FIG. 23C is a phase contrast image showing cells from NPC spheres during neural patterning of the human iPSCs. The morphology of the cells at day 8 was captured. Scale bar: 200 μm.

Figure 24:
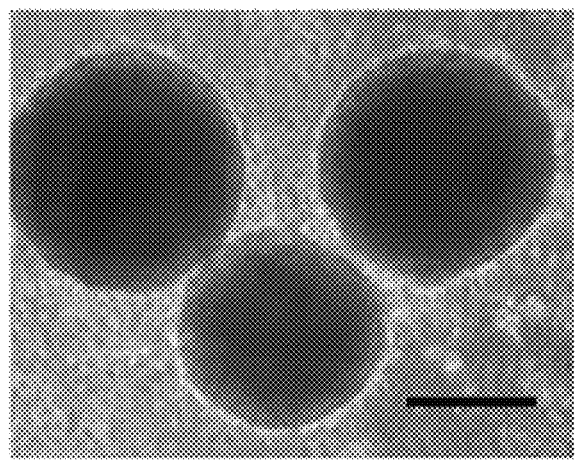

FIG. 24 is a phase contrast image showing cells from NPC spheres during neural patterning of the human iPSCs. Cells were grown without growth factors. The morphology of the cells at day 15 was captured. Scale bar: 200 μm.

Figure 25:
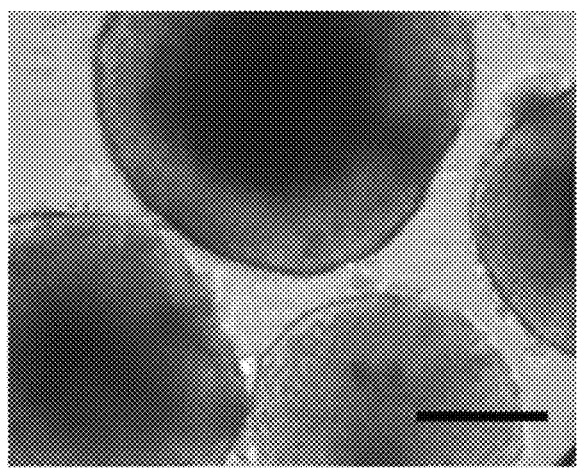

FIG. 25 is a phase contrast image showing cells from NPC spheres during neural patterning of the human iPSCs. Cells were grown with cyclopamine. The morphology of the cells at day 15 was captured. Scale bar: 200 μm.

Figure 26:
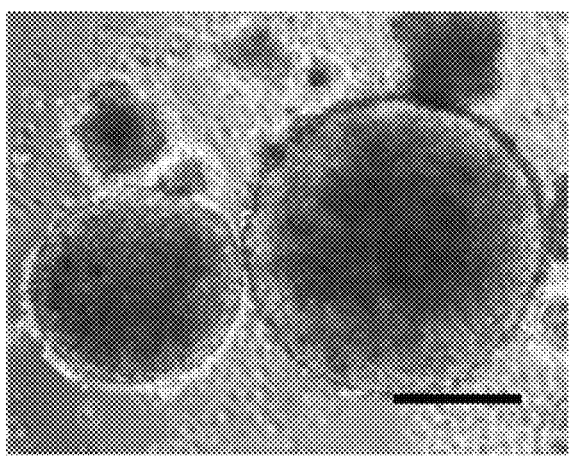

FIG. 26 is a phase contrast image showing cells from NPC spheres during neural patterning of the human iPSCs. Cells were grown with purmorphamine. The morphology of the cells at day 15 was captured. Scale bar: 200 μm.

Figure 27:
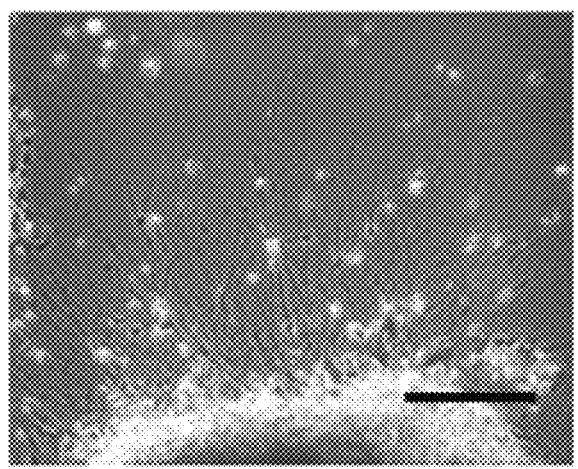

FIG. 27 is a phase contrast image showing cells from NPC spheres during neural patterning of the human iPSCs. Cells were grown for 15 days without growth factors and replated. The morphology of the cells at day 16 was captured, showing neural outgrowth. Scale bar: 200 μm.

Figure 28:
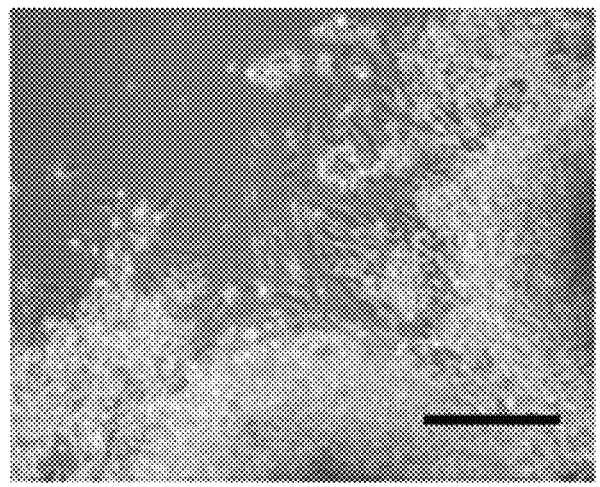

FIG. 28 is a phase contrast image showing cells from NPC spheres during neural patterning of the human iPSCs. Cells were grown for 15 days with cyclopamine and replated. The morphology of the cells at day 16 was captured, showing neural outgrowth. Scale bar: 200 μm.

Figure 29:
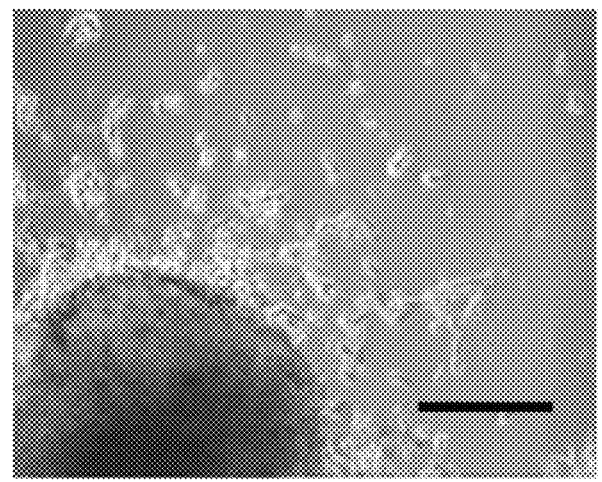

FIG. 29 is a phase contrast image showing cells from NPC spheres during neural patterning of the human iPSCs. Cells were grown for 15 days with purmorphamine and replated. The morphology of the cells at day 16 was captured, showing neural outgrowth. Scale bar: 200 μm.

Figure 30:
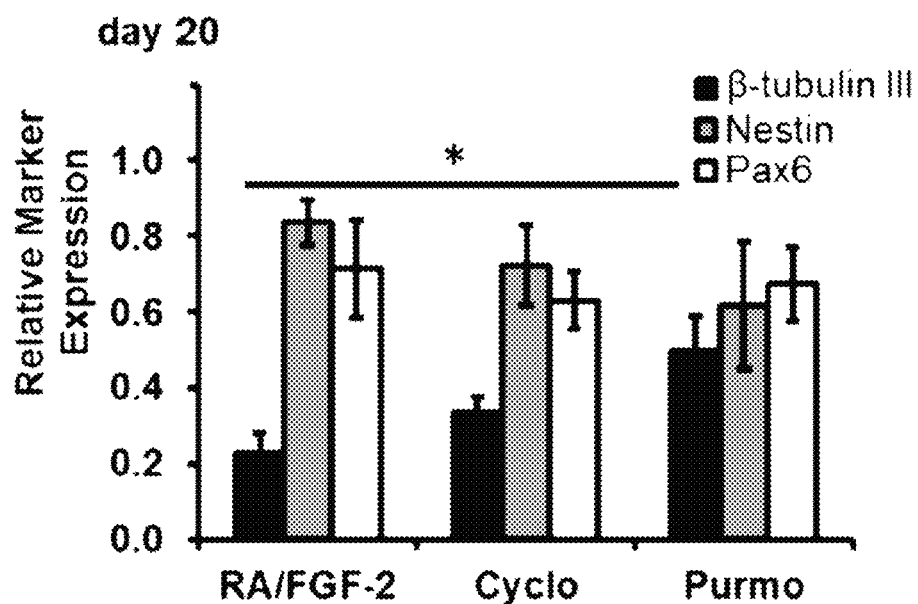

FIG. 30 is a graph showing neural tissue patterning from hiPSK3-derived EBs using cyclopamine or purmorphamine. Quantification of Nestin, Pax6, and β-tubulin III expression was performed on fluorescent images of Nestin/Pax6/Hoechst and β-tubulin III (n-tub III)/Hoechst.

Figure 31:
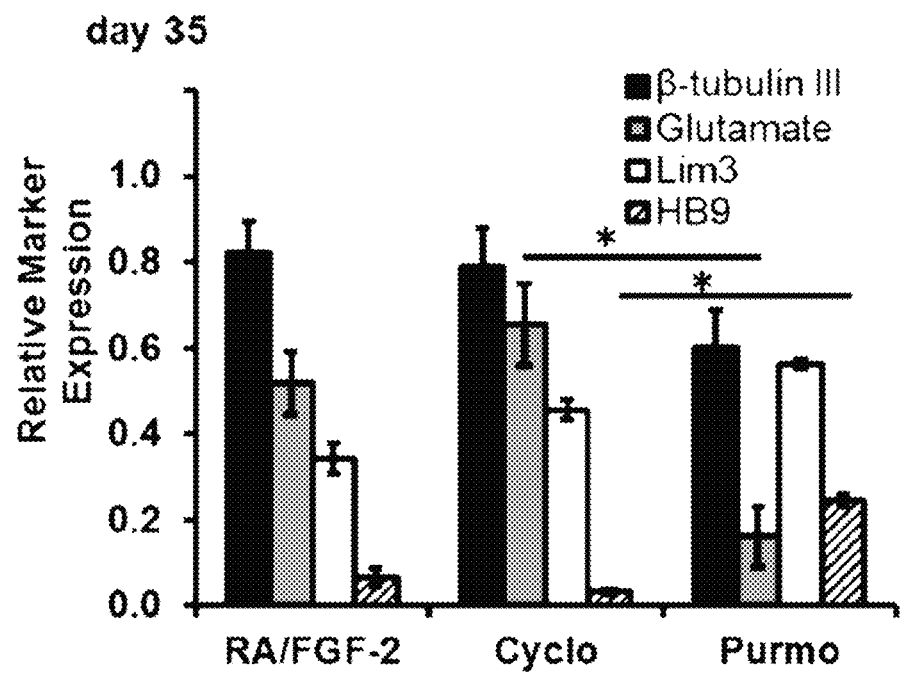

FIG. 31 is a graph showing neural tissue patterning from hiPSK3-derived EBs using cyclopamine or purmorphamine. Quantification of β-tubulin III, glutamate, Lim3 and HB9 expression was performed on fluorescent images.

Figure 32A:
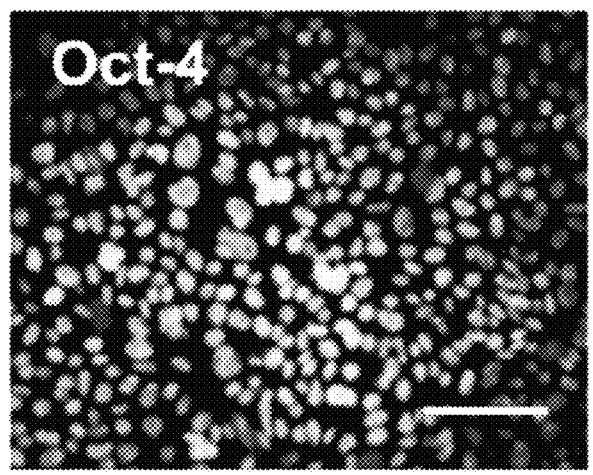

FIG. 32A is a fluorescent image from an immunolabeled cell for Oct-4 staining, 7 days of undifferentiated iPSK-3 cells. Scale bar: 100 μm.

Figure 32B:
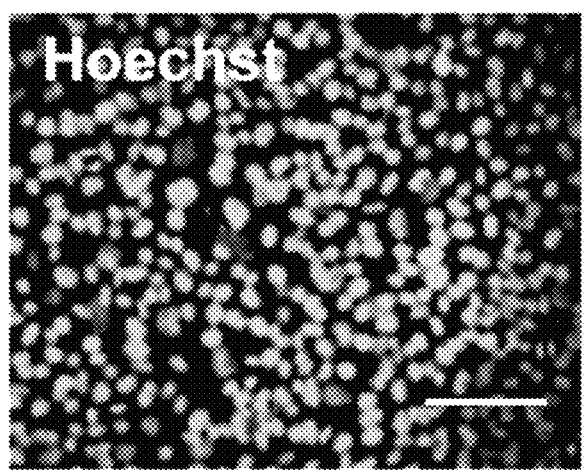

FIG. 32B is a fluorescent image from an immunolabeled cell for Hoechst staining, 7 days of undifferentiated iPSK-3 cells. Scale bar: 100 μm.

Figure 33A:
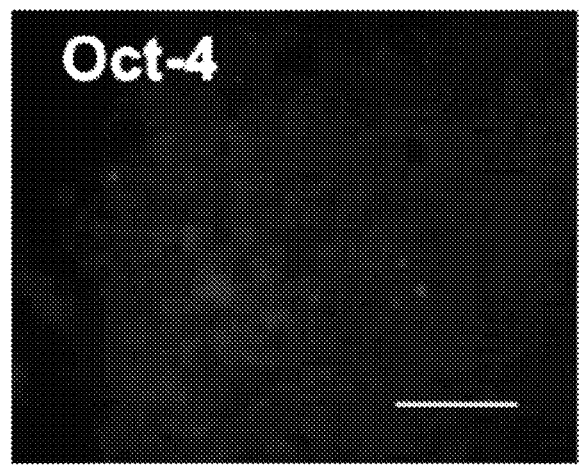

FIG. 33A is a fluorescent image from an immunolabeled cell for Oct-4 staining, 7 days after ectodermal induction of iPSK-3 cells using LDN/SB methodology. Scale bar: 100 μm.

Figure 33B:
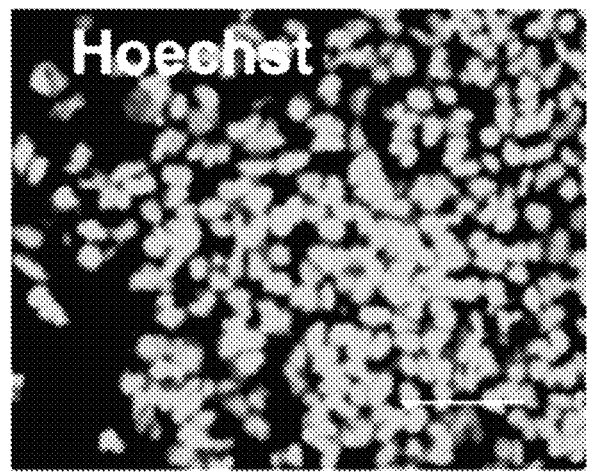

FIG. 33B is a fluorescent image from an immunolabeled cell for Hoechst staining, 7 days after ectodermal induction of iPSK-3 cells using LDN/SB methodology. Scale bar: 100 μm.

Figure 34A:
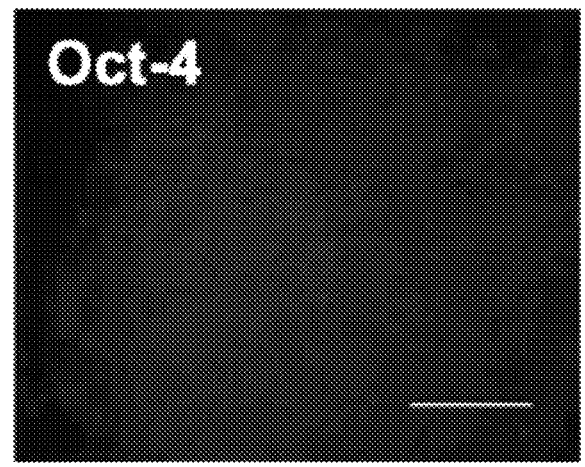

FIG. 34A is a fluorescent image from an immunolabeled cell for Oct-4 staining, 7 days after ectodermal induction of iPSK-3 cells using RA/FGF-2 methodology. Scale bar: 100 µm.

Figure 34B:
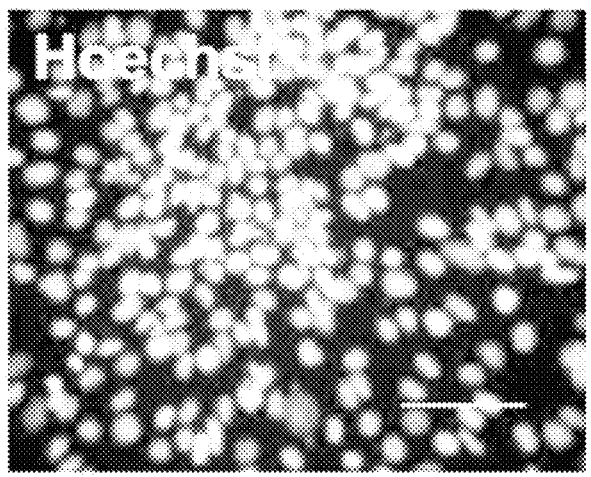

FIG. 34B is a fluorescent image from an immunolabeled cell for Hoechst staining, 7 days after ectodermal induction of iPSK-3 cells using RA/FGF-2 methodology. Scale bar: 100 µm.

Figure 35A:
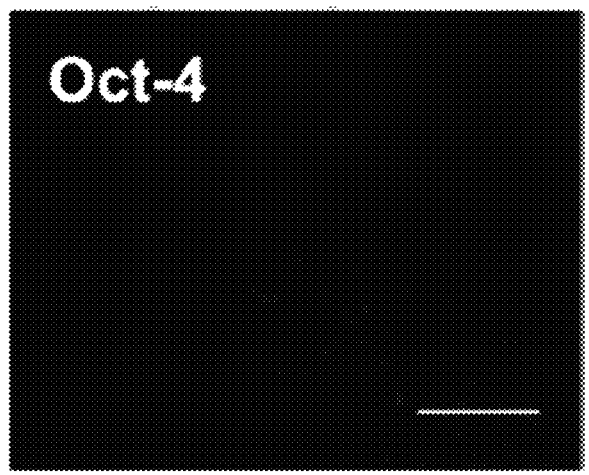

FIG. 35A is a fluorescent image from an immunolabeled cell for Oct-4 staining, 15 days after ectodermal induction of iPSK-3 cells using cyclopamine methodology. Scale bar: 100 µm.

Figure 35B:
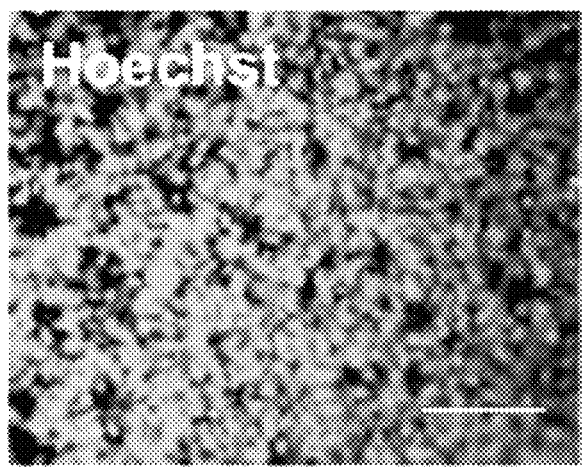

FIG. 35B is a fluorescent image from an immunolabeled cell for Hoechst staining, 15 days after ectodermal induction of iPSK-3 cells using cyclopamine methodology. Scale bar: 100 µm.

Figure 36A:
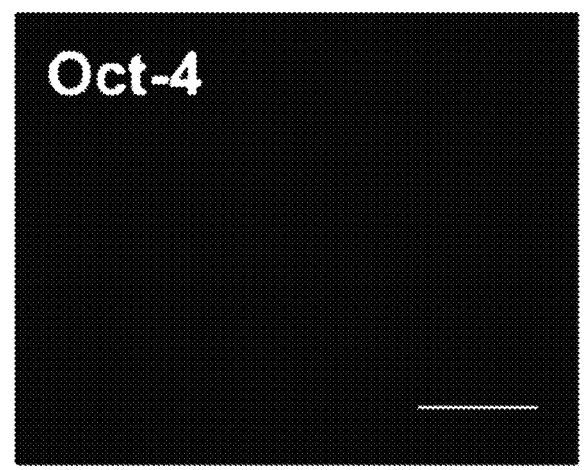

FIG. 36A is a fluorescent image from an immunolabeled cell for Oct-4 staining, 15 days after ectodermal induction of iPSK-3 cells using purmorphamine methodology. Scale bar: 100 µm.

Figure 36B:
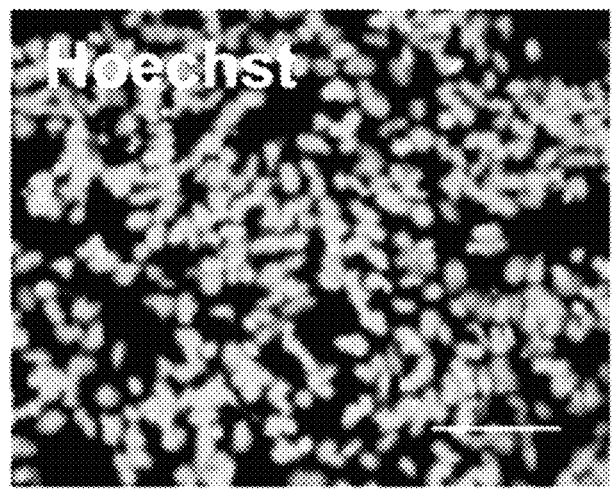

FIG. 36B is a fluorescent image from an immunolabeled cell for Hoechst staining, 15 days after ectodermal induction of iPSK-3 cells using purmorphamine methodology. Scale bar: 100 µm.

Figure 37:
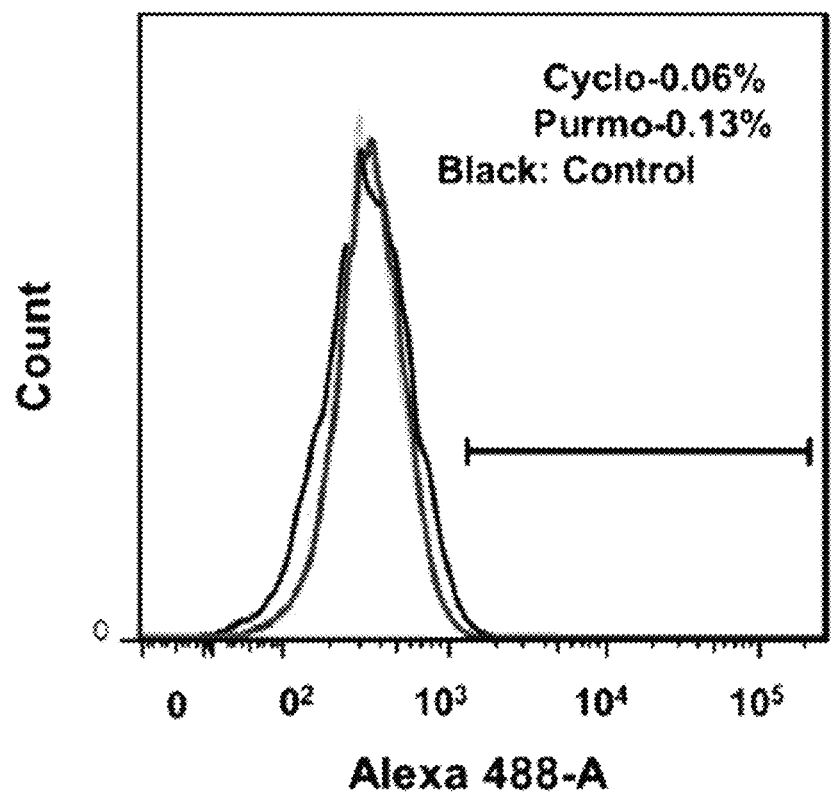

FIG. 37 is a graph showing representative flow cytometry histograms of Oct-4 expression for day-20 differentiated cells. The black line represents the control, the drak gray line represents cells treated with cyclopamine methodology, and the light gray line represents cells treated with purmorphamine.

Figure 38:
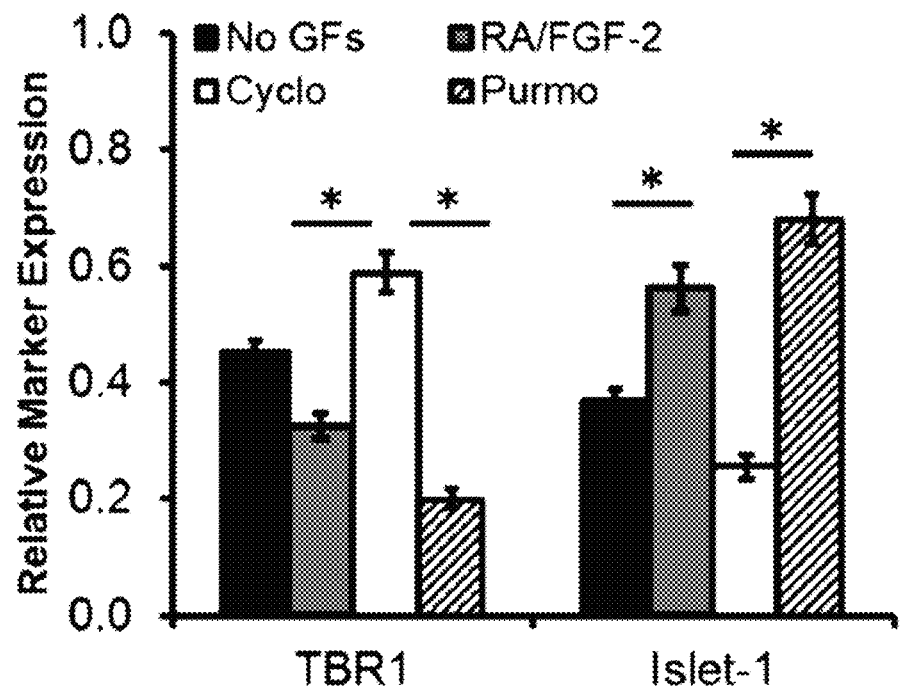

FIG. 38 is a graph showing characterizations of neuronal cells derived from hiPSK3 cells for patterning markers. Cells stained for TBR1 and Islet-1 (ISL1) expression were quantified for each differentiation method. * p<0.05.

Figure 39:
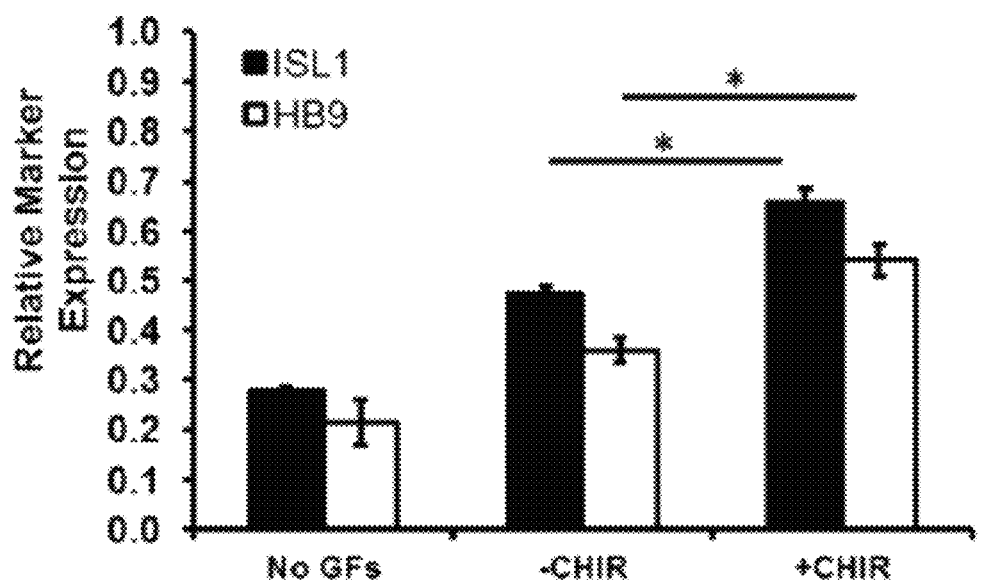

FIG. 39 is a graph showing Wnt activators further improves motor neuron differentiation. Cells were treated with CHIR99021 and stained with ISL, β-tubulin III, and HB9. Expression was quantified for ISL1 and HB9. No GFs: no growth factors used during day 8-16; −CHIR: purmorphamine/FG-2/RA (Purmo group); +CHIR: purmorphamine/FG-2/RA/CHIR. * p-value <0.05.

Figure 40:
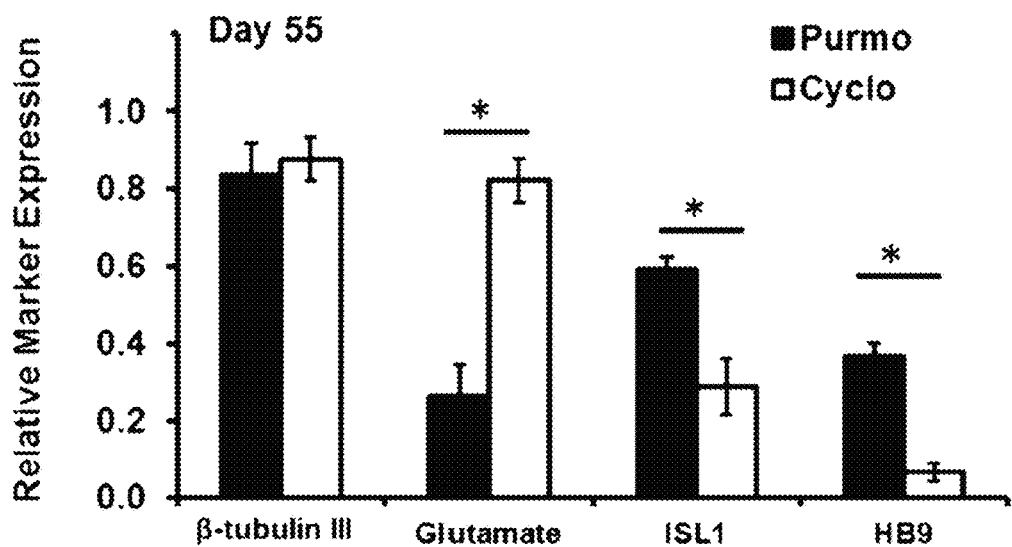

FIG. 40 is a graph showing long-term characterizations of neuronal cells derived from hiPSK3 cells. Long-term characterizations of the derived neuronal cells were performed at day 55. Cells were stained for glutamate, β-tubulin III, ISL1, HB9, and Hoechst. Expression was quantified for β-tubulin III, Glutamate, ISL1, and HB9 expression. * p<0.05

Figure 41A:
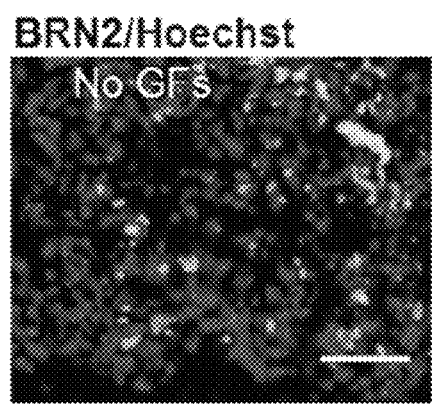

FIG. 41A is a microscopic image showing Representative fluorescent images are shown for the expression of a superficial cortical layer II-IV marker BRN2 (light gray)/Hoechst (medium gray) (day 42). Cells were grown without any growth factors.

Figure 41B:
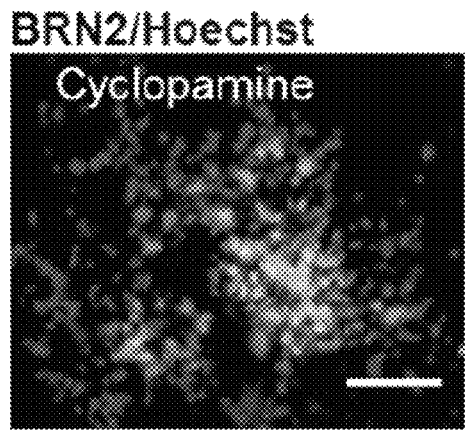

FIG. 41B is a microscopic image showing Representative fluorescent images are shown for the expression of a superficial cortical layer II-IV marker BRN2 (light gray)/Hoechst (medium gray) (day 42). Cells were induced using cyclopamine. Scale bar: 100 µm.

Figure 41C:
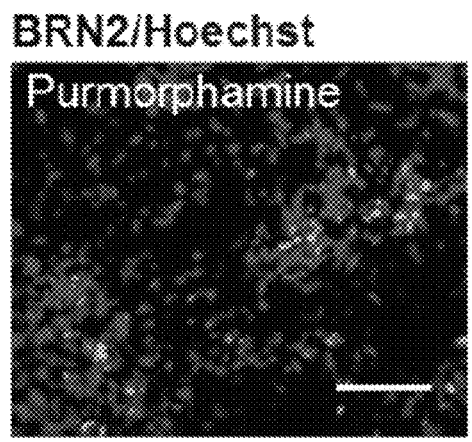

FIG. 41C is a microscopic image showing representative fluorescent images are shown for the expression of a superficial cortical layer II-IV marker BRN2 (light gray)/Hoechst (medium gray) (day 42). Cells were induced using purmorphamine. Scale bar: 100 µm.

Figure 42A:
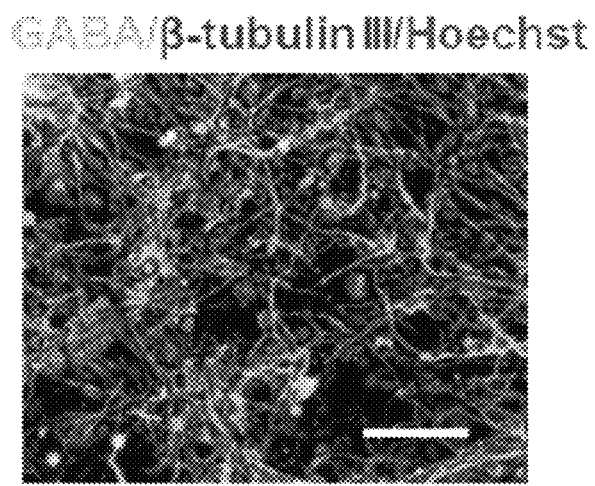

FIG. 42A is a microscopic image showing representative fluorescent image for GABA (light gray)/P3-tubulin III (medium gray)/Hoechst (dark gray) expression (day 45 cells from the Cyclo group). Scale bar: 100 µm.

Figure 42B:
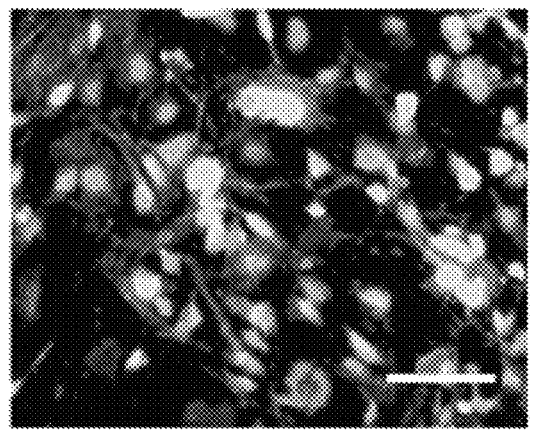

FIG. 42B is a microscopic image showing representative fluorescent image for GFAP (medium gray)/Hoechst (light gray) expression (day 45 cells from the Cyclo group). Scale bar: 100 µm.

Figure 43:
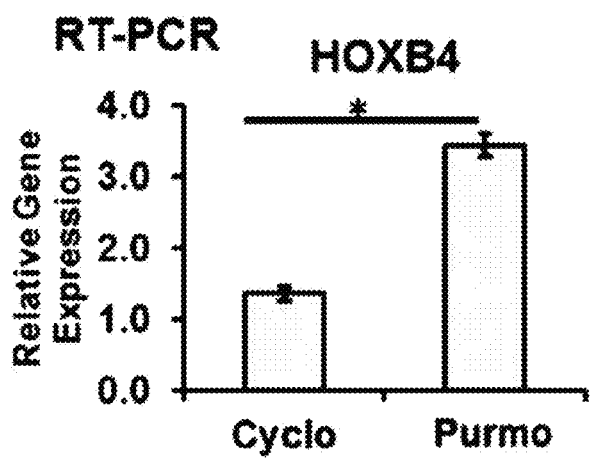

FIG. 43 is a graph showing characterizations of neuronal cells derived from hiPSK3 cells for patterning markers RT-PCR analysis for HOXB4 (hindbrain/spinal cord) expression in day 35 cells (reference: day 21 control cells). * p<0.05.

Figure 44:
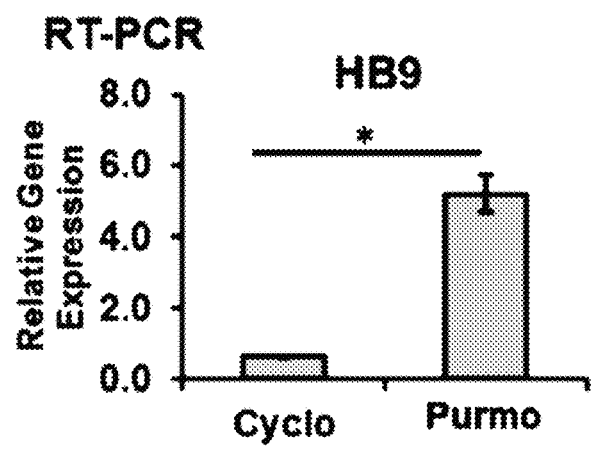

FIG. 44 is a graph showing characterizations of neuronal cells derived from hiPSK3 cells for patterning markers. RT-PCR analysis for HB9 (motor neuron) expression in day 35 cells (reference: day 21 control cells). * p<0.05.

Figure 45:
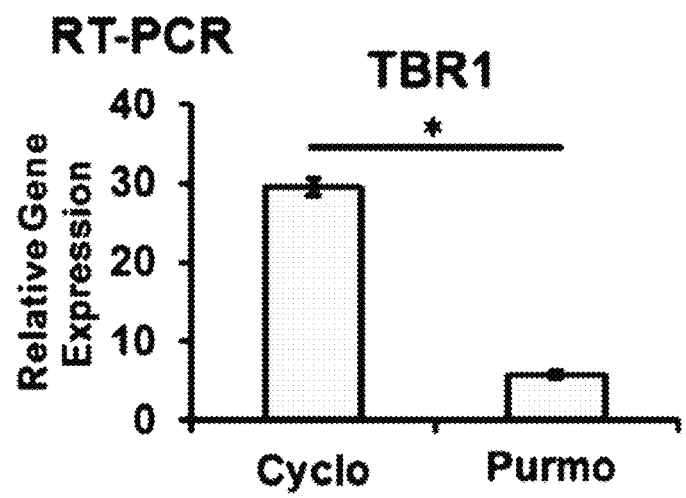

FIG. 45 is a graph showing characterizations of neuronal cells derived from hiPSK3 cells for patterning markers. RT-PCR analysis for TBR1 (cortical glutamatergic neuron) expression in day 35 cells (reference: day 21 control cells). * p<0.05.

Figure 46:
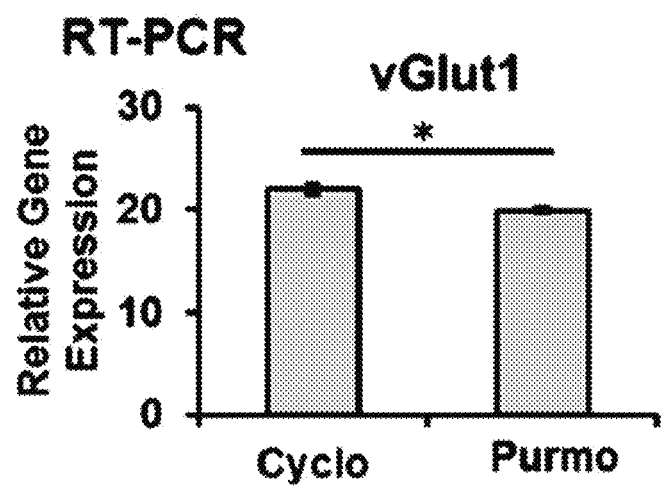

FIG. 46 is a graph showing characterizations of neuronal cells derived from hiPSK3 cells for patterning markers. RT-PCR analysis for vGlut1 (cortical glutamatergic neuron) expression in day 35 cells (reference: day 21 control cells). * p<0.05.

Figure 47:
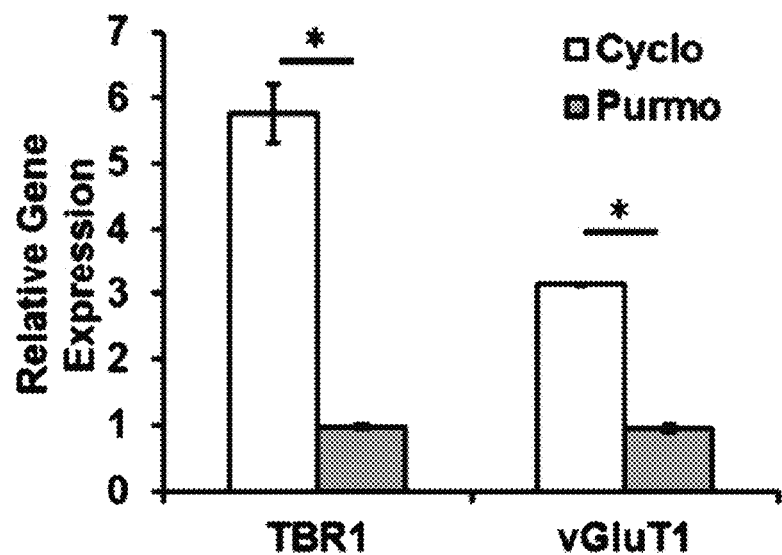

FIG. 47 is a graph showing characterizations of neuronal cells derived from hiPSK3 cells for patterning markersRT-PCR analysis for TBR1 and vGlut1 expression in day 45 cells (reference: day 45 Purmo cells). * p<0.05.

Figure 48:
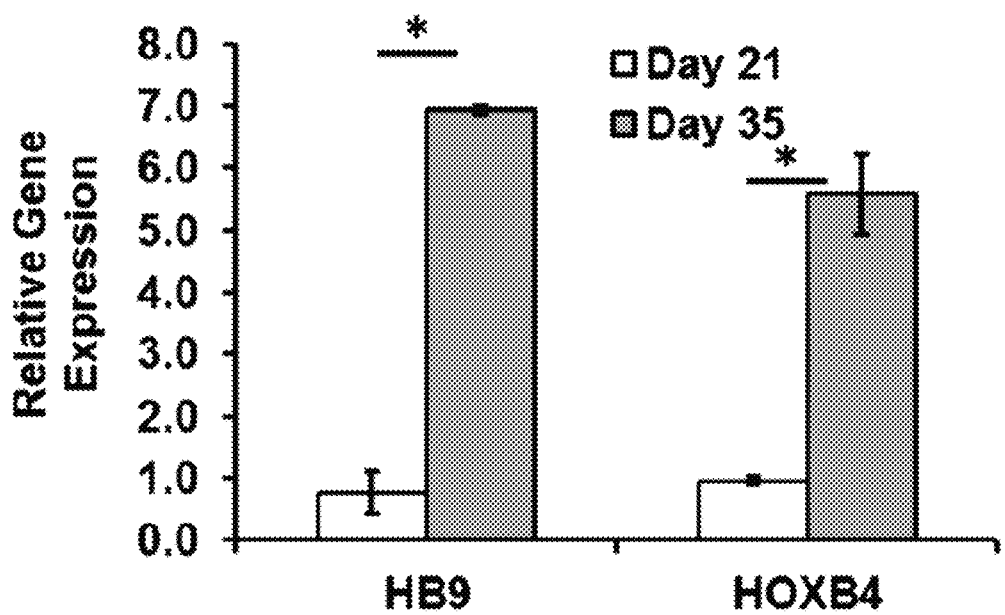

FIG. 48 is a graph showing RT-PCR analysis of HOXB4 and HB9 expression on day 35 vs. day 21 differentiation of neural cells for the control group. *p-value<0.05.

Figure 49:
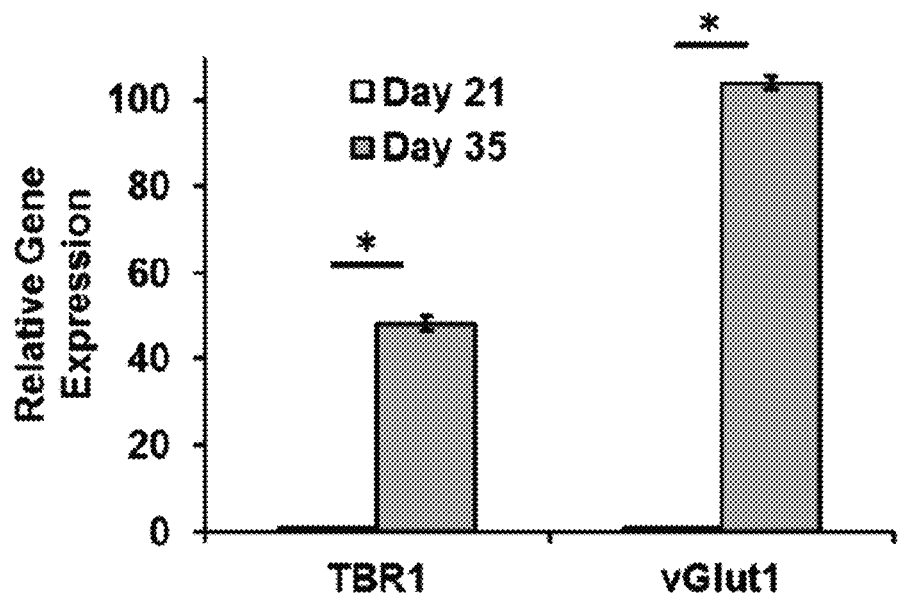

FIG. 49 is a graph showing RT-PCR analysis of TBR1 and vGlut1 expression on day 35 vs. day 21 differentiation of neural cells for the control group. *p-value<0.05.

Figure 50A:
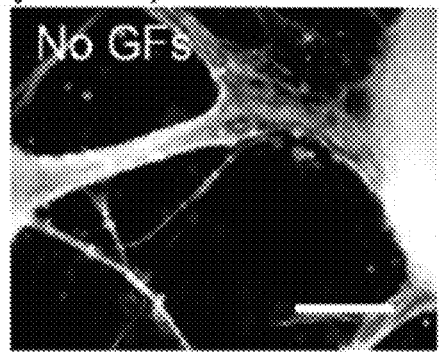

FIG. 50A is a microscopic image showing synaptic marker expression of the neural cells derived from hiPSK3 cells. Representative fluorescent images of synaptic markers Synapsin I (medium gray)/β-tubulin III (light gray)/Hoechst (dark gray) for day 35 cells without growth factors. Scale bar: 100 µm.

Figure 50B:
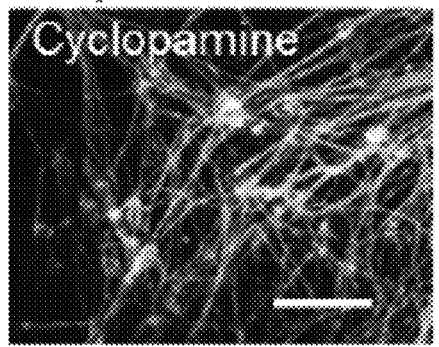

FIG. 50B is a microscopic image showing synaptic marker expression of the neural cells derived from hiPSK3 cells. Representative fluorescent images of synaptic markers Synapsin I (medium gray)/β-tubulin III (light gray)/Hoechst (dark gray) for day 35 cells induced with cyclopamine. Scale bar: 100 µm.

Figure 50C:
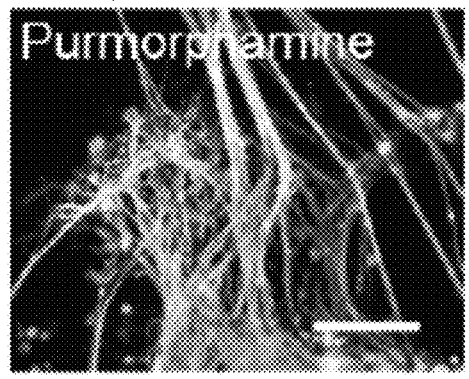

FIG. 50C is a microscopic image showing synaptic marker expression of the neural cells derived from hiPSK3 cells. Representative fluorescent images of synaptic markers Synapsin I (medium gray)/β-tubulin III (light gray)/Hoechst (dark gray) for day 35 cells induced with purmorphamine. Scale bar: 100 µm.

Figure 51A:
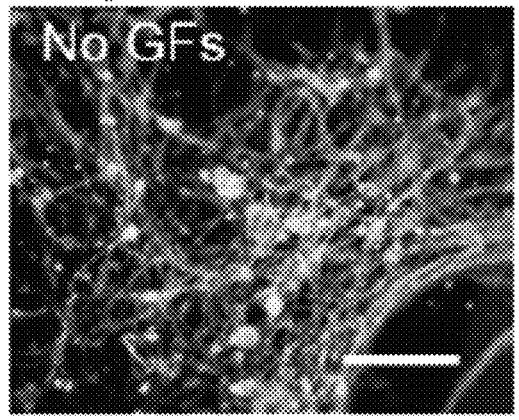

FIG. 51A is a microscopic image showing synaptic marker expression of the neural cells derived from hiPSK3 cells. Representative fluorescent images of Synaptic markers PSD95 (red)/β-tubulin III (green)/Hoechst (blue) for day 35 cells without growth factors. Scale bar: 100 µm.

Figure 51B:
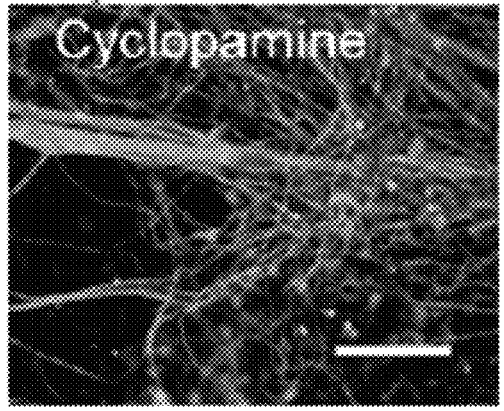

FIG. 51B is a microscopic image showing synaptic marker expression of the neural cells derived from hiPSK3 cells. Representative fluorescent images of Synaptic markers PSD95 (red)/β-tubulin III (green)/Hoechst (blue) for day 35 cells induced with cyclopamine. Scale bar: 100 µm.

Figure 51C:
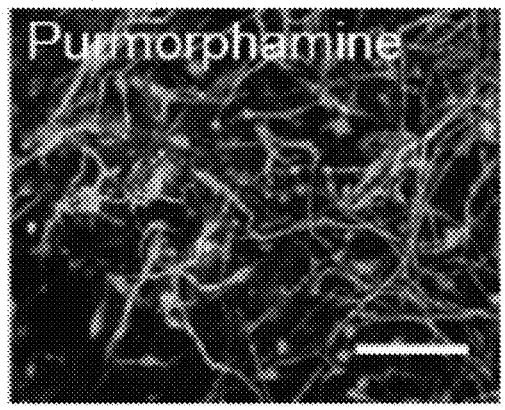

FIG. 51C is a microscopic image showing synaptic marker expression of the neural cells derived from hiPSK3 cells. Representative fluorescent images of Synaptic markers PSD95 (red)/β-tubulin III (green)/Hoechst (blue) for day 35 cells induced with purmorphamine. Scale bar: 100 µm.

Figure 52A:
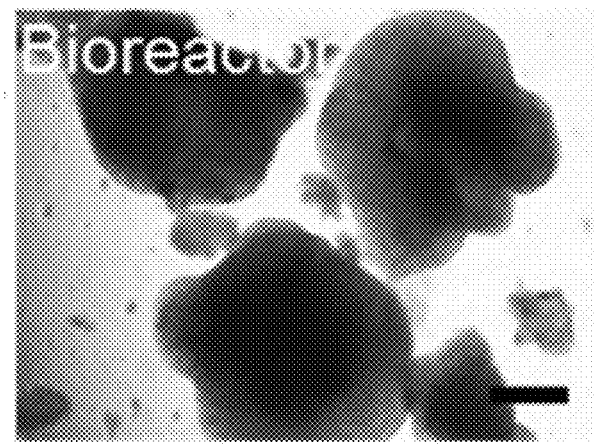

FIG. 52A is a phase contrast image showing cortical organoids derived from human iPSK3 cells. Cortical organoids were derived from the culture in a spinner bioreactor and images taken at day 43. Scale bar: 400 μm.

Figure 52B:
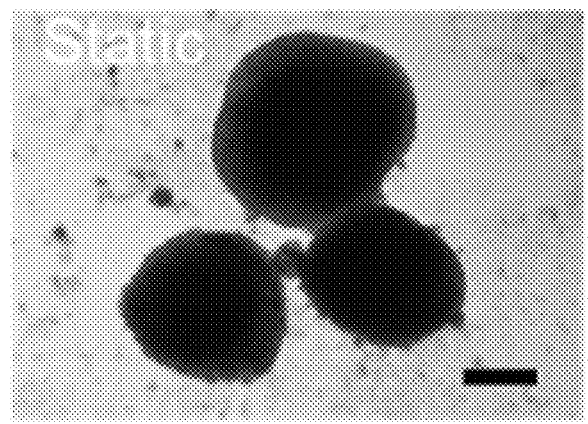

FIG. 52B is a phase contrast image showing cortical organoids derived from human iPSK3 cells. Cortical organoids were derived from the culture in a 24-well plate (static control) and images taken at day 43. Scale bar: 400 μm.

Figure 53A:
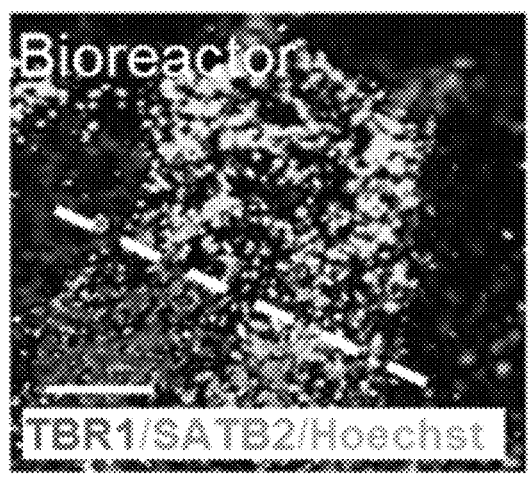

FIG. 53A is a confocal image showing cortical organoids derived from human iPSK3 cells. Cortical organoids were derived from the culture in a spinner bioreactor and cells stained for TBR1 and SATB2 at day 71. Scale bar: 400 μm.

Figure 53B:
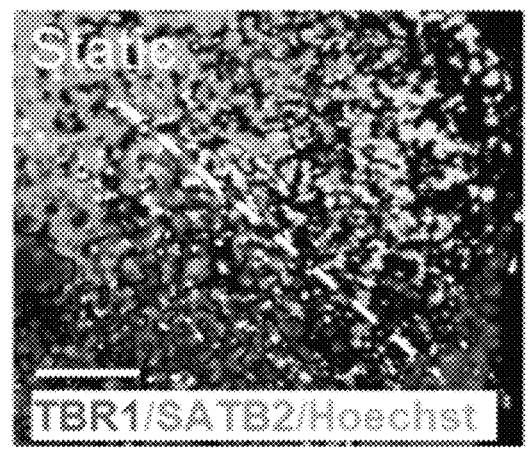

FIG. 53B is a confocal image showing cortical organoids derived from human iPSK3 cells. Cortical organoids were derived from the culture in a 24-well plate (static control) and cells stained for TBR1 and SATB2 at day 71. Scale bar: 400 μm.

Figure 54:
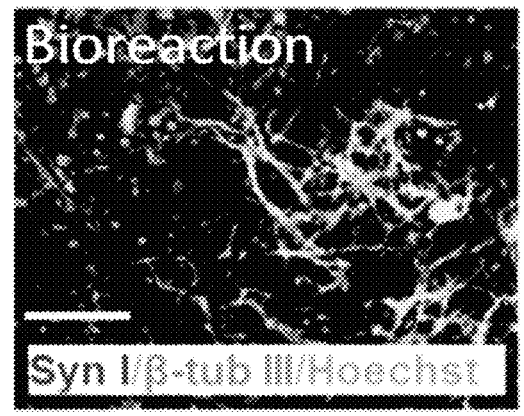

FIG. 54 is a confocal image showing cortical organoids derived from human iPSK3 cells. Cortical organoids were derived from the culture in a spinner bioreactor and cells stained for the pre-synaptic marker, synapsin I, along with β-tubulin III at day 32-bioreactor. Scale bar: 100 μm.

Figure 55:
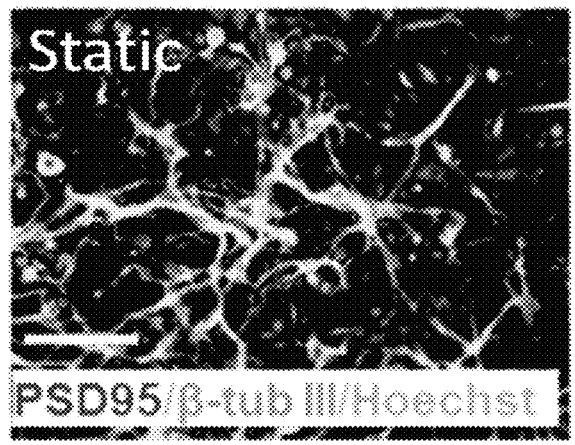

FIG. 55 is a confocal image showing cortical organoids derived from human iPSK3 cells. Cortical organoids were derived from the culture in a spinner bioreactor and cells stained for the post-synaptic marker, PSD95, along with β-tubulin III at day 32-bioreactor. Scale bar: 100 μm.

Figure 56:
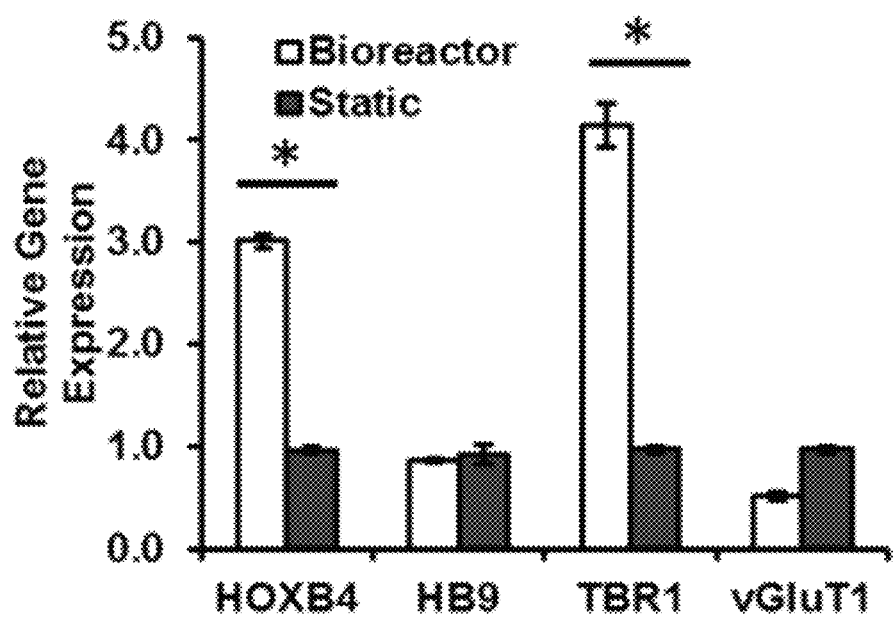

FIG. 56 is a graph showing cortical organoids derived from human iPSK3 cells. Cells were collected at day 32 and RT-PCR analysis performed for HOXB4, HB9, TBR1, vGluT1.

Figure 57:
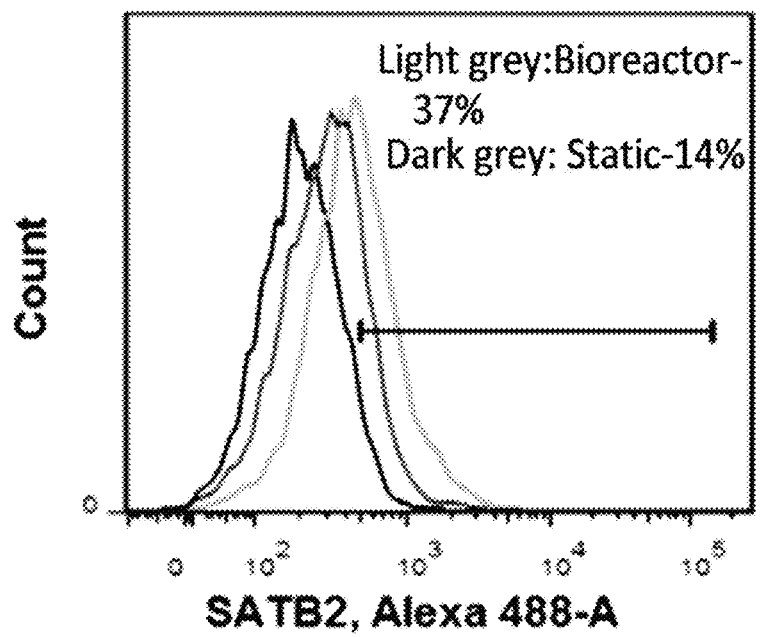

FIG. 57 is a graph showing cortical organoids derived from human iPSK3 cells. Cells were collected at day 32 and flow cytometry analysis performed for SATB2 expression. *p-value<0.05.

Figure 58:
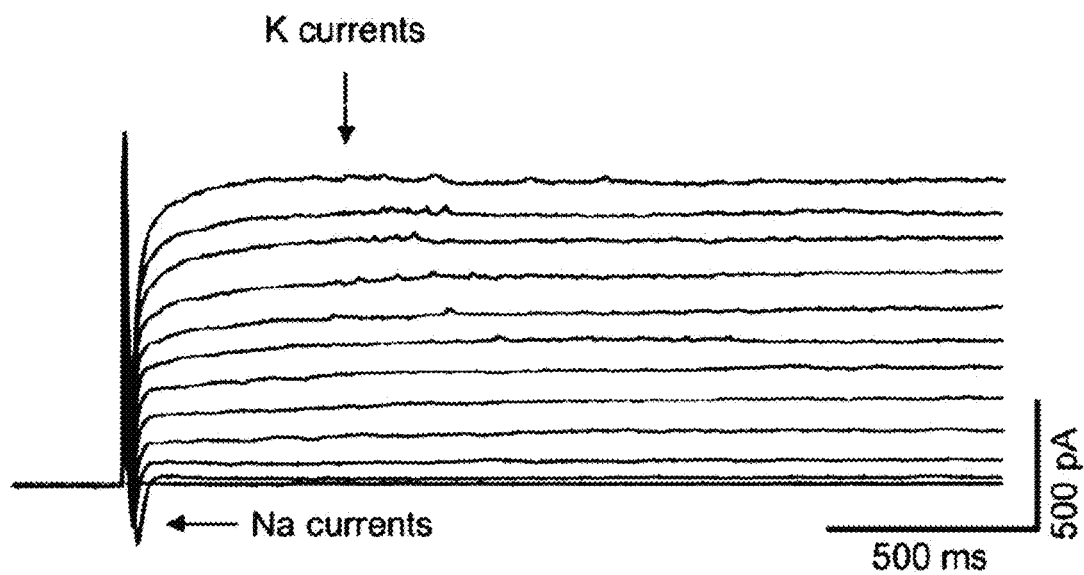

FIG. 58 is a graph showing electrophysiology of neuronal cells derived from hiPSK3 cells. Patch clamp recordings of fast-inactivating $Na^+$ currents followed by long-lasting outward $K^+$ currents on the neuronal outgrowth of the replated aggregates (day 50 of differentiation, Purmorphamine group) showing the generation of $Na^+$ and $K^+$ currents.

Figure 59:
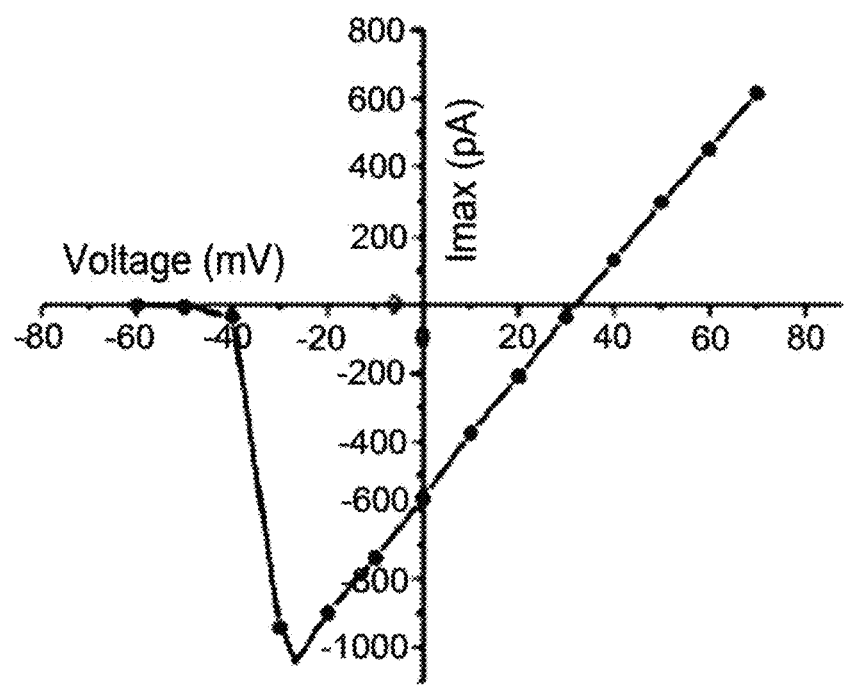

FIG. 59 is a graph showing electrophysiology of neuronal cells derived from hiPSK3 cells. Patch clamp recordings I-V curve for Na currents on the neuronal outgrowth of the replated aggregates (day 50 of differentiation, Purmorphamine group) showing the generation of $Na^+$.

Figure 60:
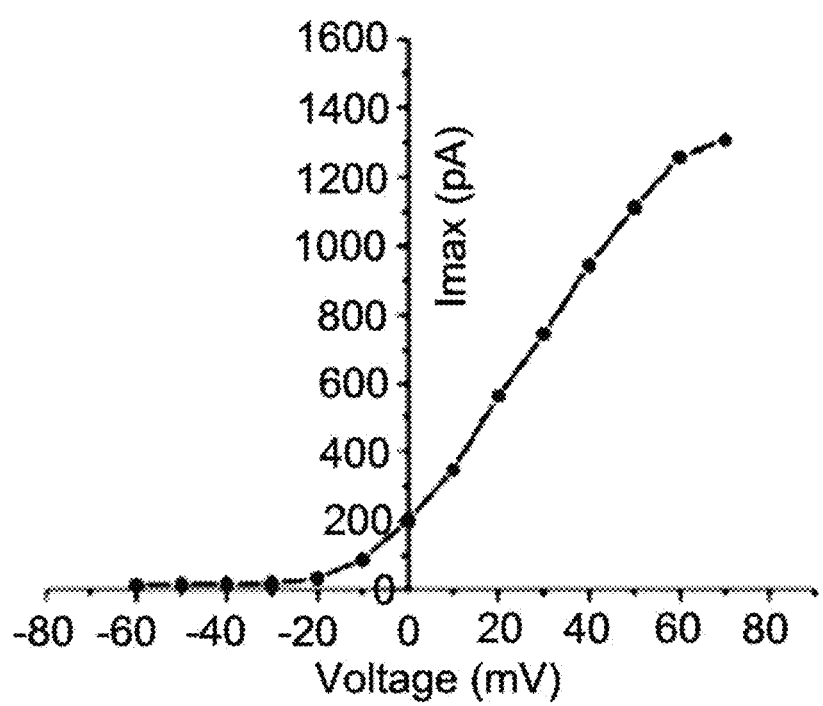

FIG. 60 is a graph showing electrophysiology of neuronal cells derived from hiPSK3 cells. Patch clamp recordings of I-V curve for K currents on the neuronal outgrowth of the replated aggregates (day 50 of differentiation, Purmorphamine group) showing the generation of $K^+$ currents.

Figure 61:
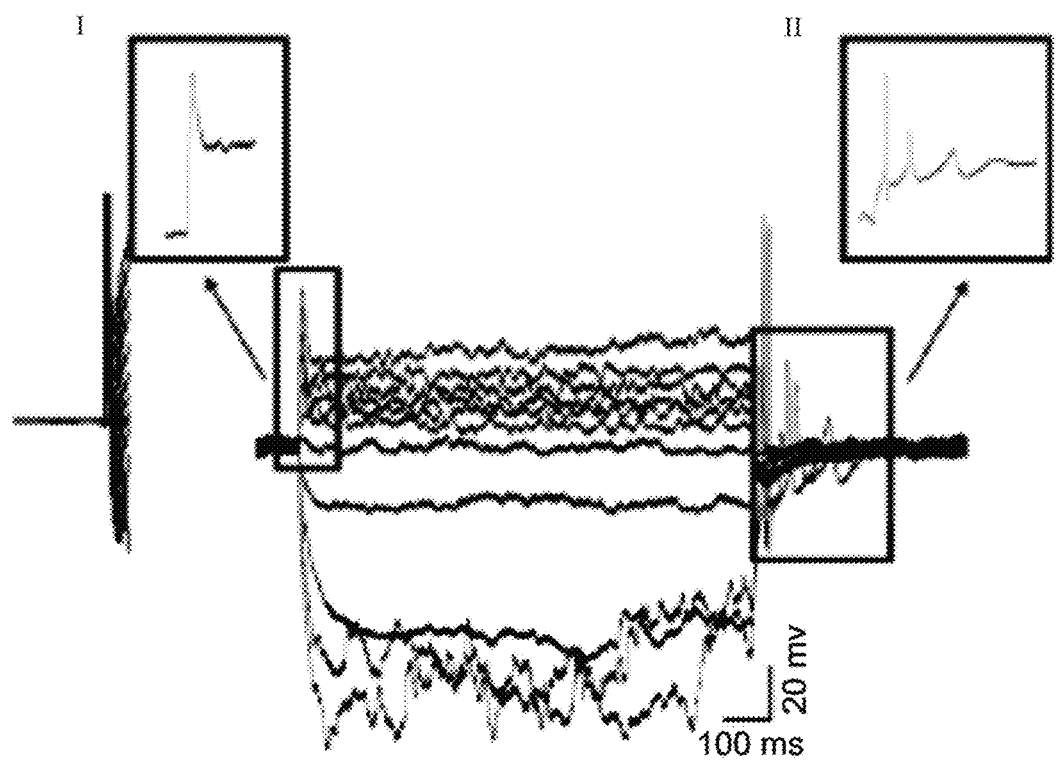

FIG. 61 is a graph showing electrophysiology of neuronal cells derived from hiPSK3 cells. Patch clamp recordings on the neuronal cells (day 30 of differentiation, Purmorphamine group) showing the firing of action potentials in response to depolarizing current injections, as well as at the end of hyperpolarizing current injections ("rebound" action potentials).

Figure 62:
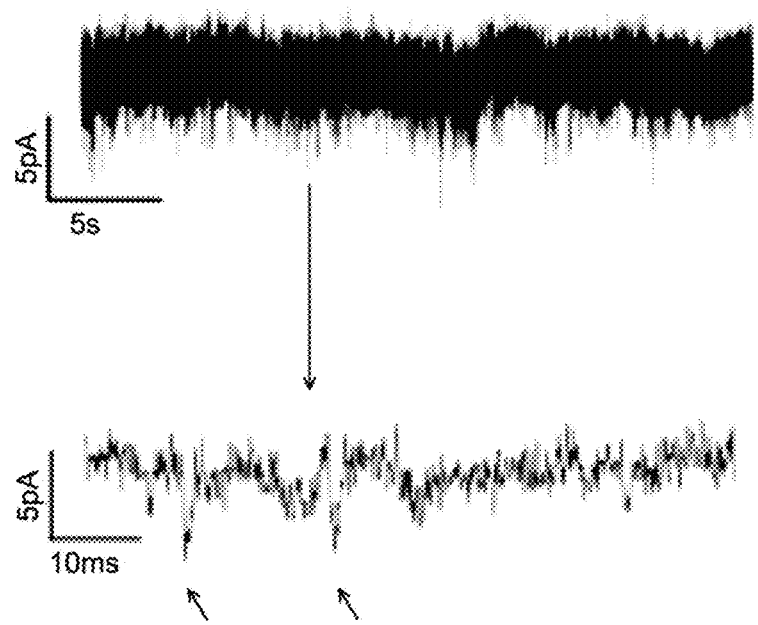

FIG. 62 is a graph showing electrophysiology of neuronal cells derived from hiPSK3 cells. Patch clamp recordings on the neuronal cells (day 30 of differentiation, Purmorphamine group) showing the firing of action potential and spontaneous excitatory post-synaptic currents (sEPSC).

Figure 63:
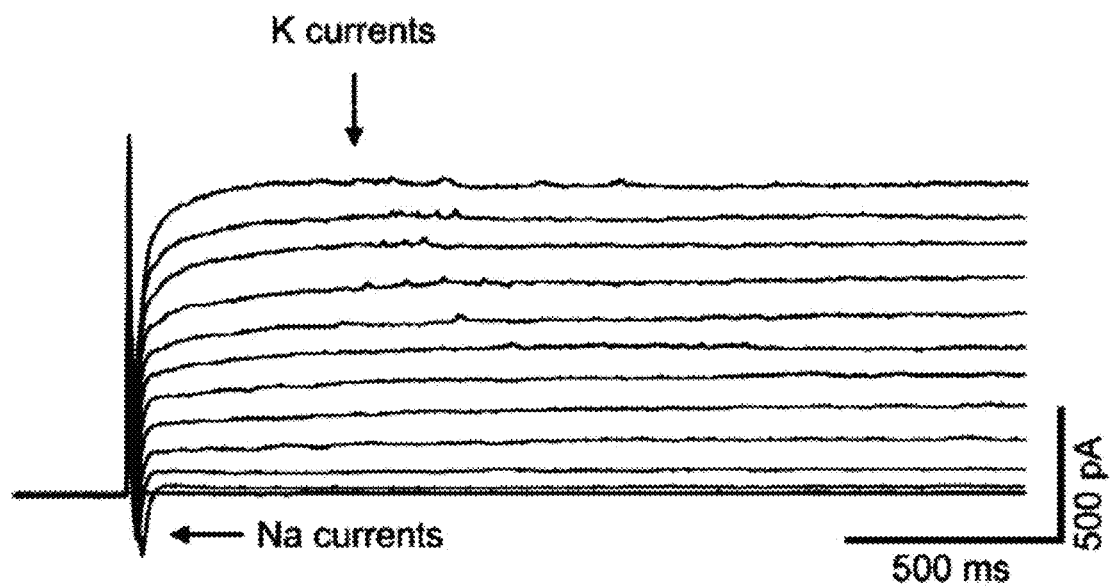

FIG. 63 is a graph showing electrophysiology of neuronal cells derived from hiPSK3 cells. Patch clamp recordings on the derived neuronal cells (day 35 of differentiation, Cyclopamine group) showing the generation of Na+ and K+ currents.

Figure 64:
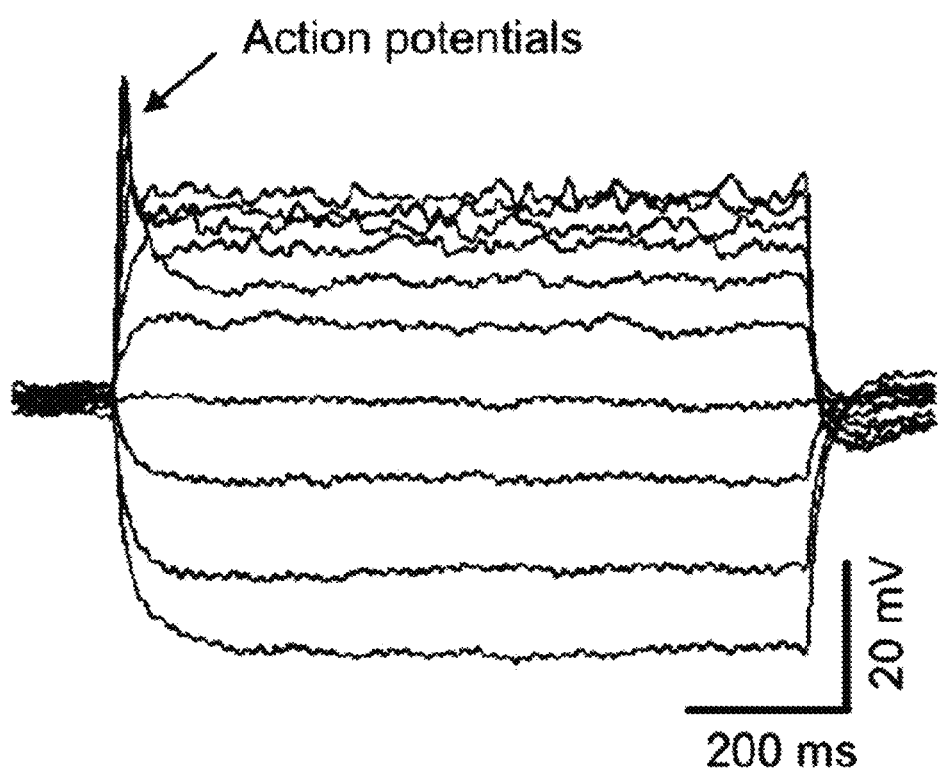

FIG. 64 is a graph showing electrophysiology of neuronal cells derived from hiPSK3 cells. Patch clamp recordings on the derived neuronal cells (day 35 of differentiation, Cyclopamine group) showing the firing of action potential.

Figure 65A:
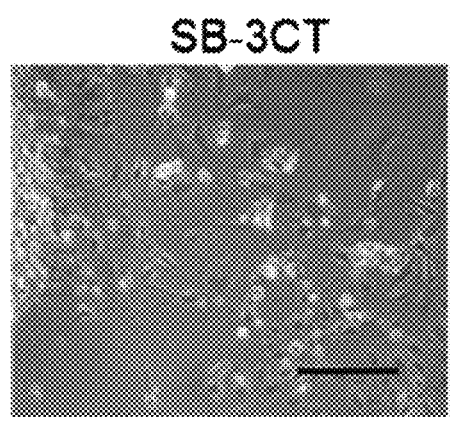

FIG. 65A is a phase contrast image showing the influences of matrix metalloproteinase (MMP)-2 and -9 inhibitors on neuronal cells derived from hiPSK3 cells. Phase contrast images showing the neuronal outgrowth when Purmo-induced cells were treated with SB-3CT inhibitor at day 45. Arrows point to the neurites. Scale bar: 200 μm.

Figure 65B:
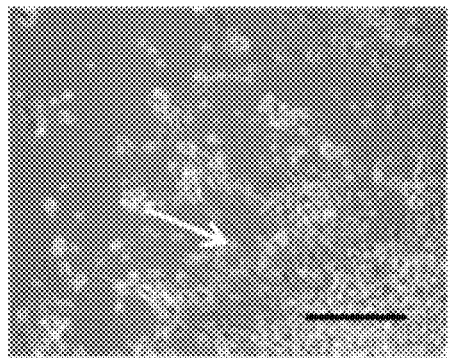

FIG. 65B is a phase contrast image showing the influences of matrix metalloproteinase (MMP)-2 and -9 inhibitors on neuronal cells derived from hiPSK3 cells. Phase contrast images showing the neuronal outgrowth when Cyclo-induced cells were treated with SB-3CT inhibitor at day 45. Arrows point to the neurites. Scale bar: 200 μm.

Figure 66A:
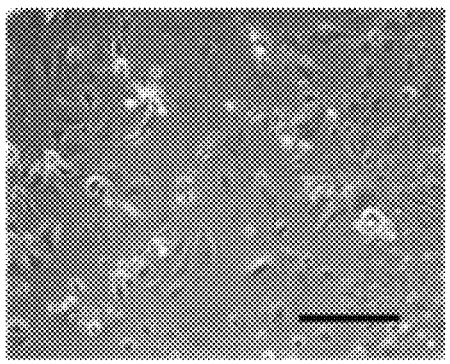

FIG. 66A is a phase contrast image showing the influences of matrix metalloproteinase (MMP)-2 and -9 inhibitors on neuronal cells derived from hiPSK3 cells. Phase contrast images showing the neuronal outgrowth when Purmo-induced cells were treated with MMP-9 inhibitor I at day 45. Arrows point to the neurites. Scale bar: 200 μm.

Figure 66B:
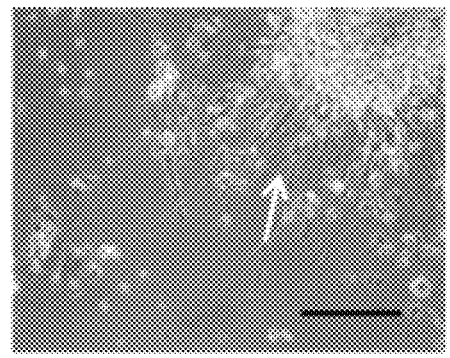

FIG. 66B is a phase contrast image showing the influences of matrix metalloproteinase (MMP)-2 and -9 inhibitors on neuronal cells derived from hiPSK3 cells. Phase contrast images showing the neuronal outgrowth when Cyclo-induced cells were treated with MMP-9 inhibitor I at day 45. Arrows point to the neurites. Scale bar: 200 μm.

Figure 67A:
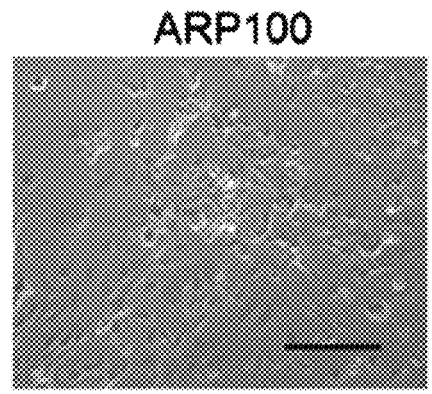

FIG. 67A is a phase contrast image showing the influences of matrix metalloproteinase (MMP)-2 and -9 inhibitors on neuronal cells derived from hiPSK3 cells. Phase contrast images showing the neuronal outgrowth when Purmo-induced cells were treated with ARP100 inhibitor at day 45. Arrows point to the neurites. Scale bar: 200 μm.

Figure 67B:
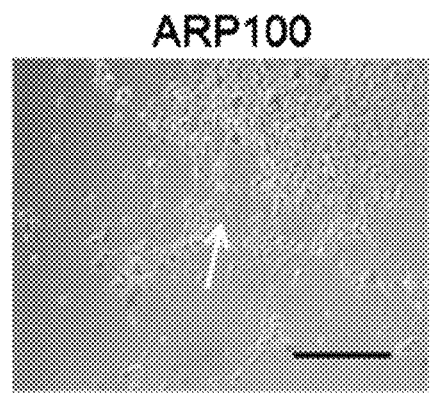

FIG. 67B is a phase contrast image showing the influences of matrix metalloproteinase (MMP)-2 and -9 inhibitors on neuronal cells derived from hiPSK3 cells. Phase contrast images showing the neuronal outgrowth when Cyclo-induced cells were treated with ARP100 inhibitor at day 45. Arrows point to the neurites. Scale bar: 200 μm.

Figure 68A:
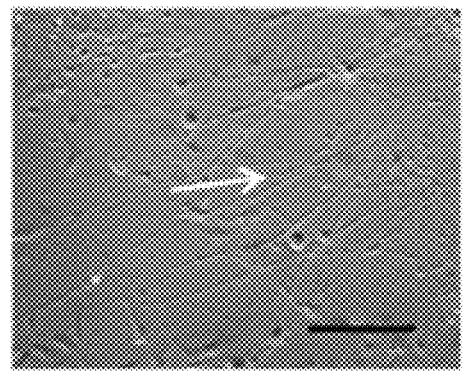

FIG. 68A is a phase contrast image showing the influences of matrix metalloproteinase (MMP)-2 and -9 inhibitors on neuronal cells derived from hiPSK3 cells. Phase contrast images showing the neuronal outgrowth when Purmo-induced cells were untreated at day 45. Arrows point to the neurites. Scale bar: 200 μm.

Figure 68B:
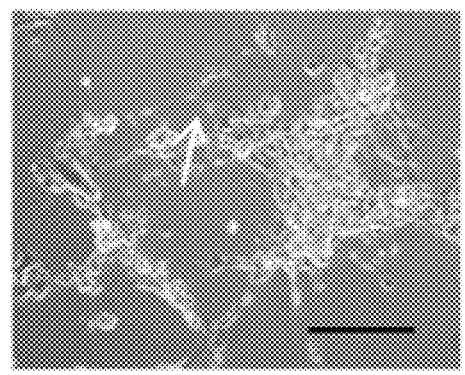

FIG. 68B is a phase contrast image showing the influences of matrix metalloproteinase (MMP)-2 and -9 inhibitors on neuronal cells derived from hiPSK3 cells. Phase contrast images showing the neuronal outgrowth when Cyclo-induced cells were untreated at day 45. Arrows point to the neurites. Scale bar: 200 μm.

Figure 69:
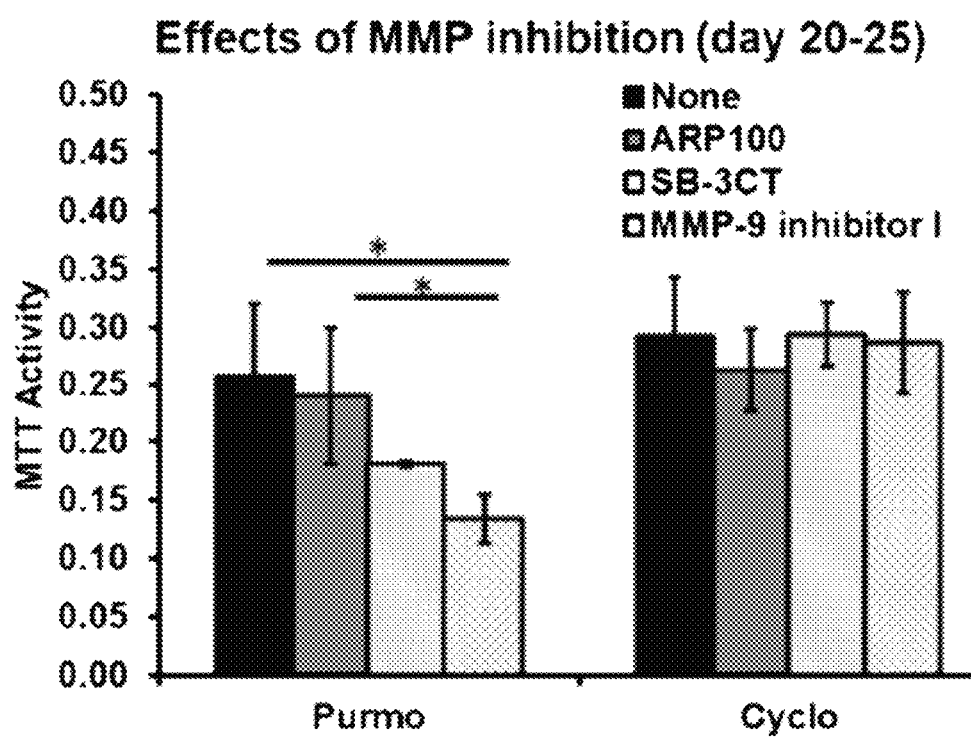

FIG. 69 is a graph showing the influences of matrix metalloproteinase (MMP)-2 and -9 inhibitors on neuronal cells derived from hiPSK3 cells. Effect of MMP inhibition on metabolic activity on day 20-25 cells. Purmo: purmophamine group; Cyclo: cyclopamine group. *p-value<0.05. non: no MMP inhibitor. ARP100: MMP-2 inhibitor; SB-3CT: MMP-2/MMP-9 inhibitor.

Figure 70:
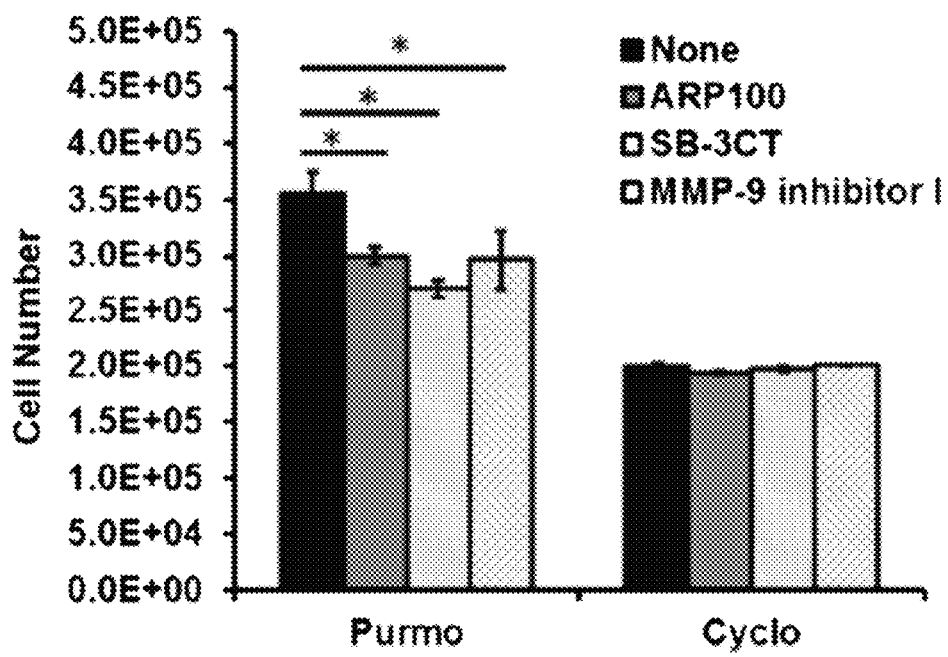

FIG. 70 is a graph showing the influences of matrix metalloproteinase (MMP)-2 and -9 inhibitors on neuronal cells derived from hiPSK3 cells. Effect of MMP inhibition on metabolic activity on day 45-50 cells. Purmo: purmophamine group; Cyclo: cyclopamine group.

*p-value<0.05. non: no MMP inhibitor. ARP100: MMP-2 inhibitor; SB-3CT: MMP-2/MMP-9 inhibitor.

Figure 71:
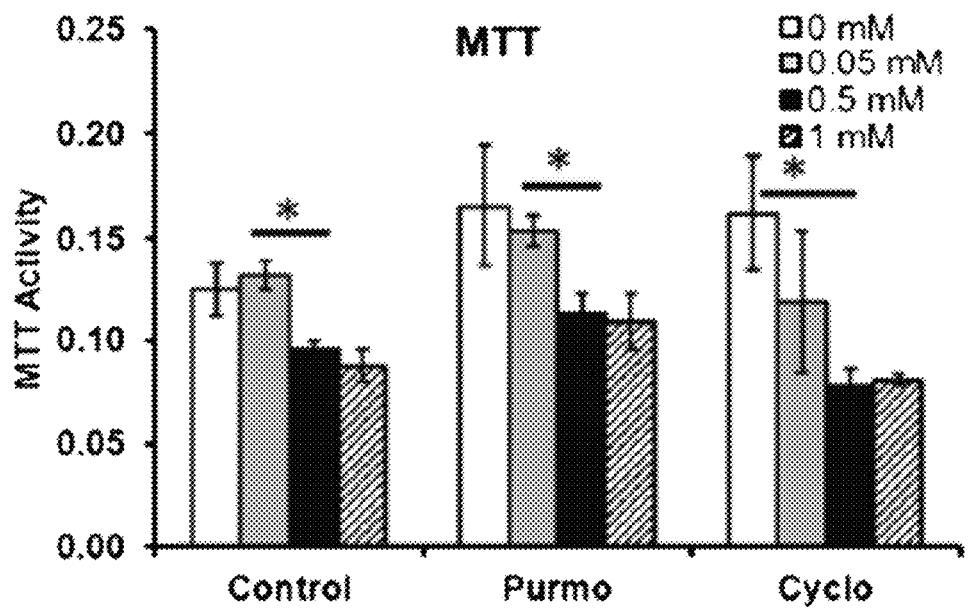

FIG. 71 is a graph showing N-methyl-D-aspartate (NMDA)-induced neurotoxicity and the influence of carbenoxolone treatment. Cells were contacted with NMDA and metabolic activity (MTT assay) was determined for control (untreated), Purmo-induced, and Cyclo-induced cells. * and ** indicate p-value<0.05.

Figure 72:
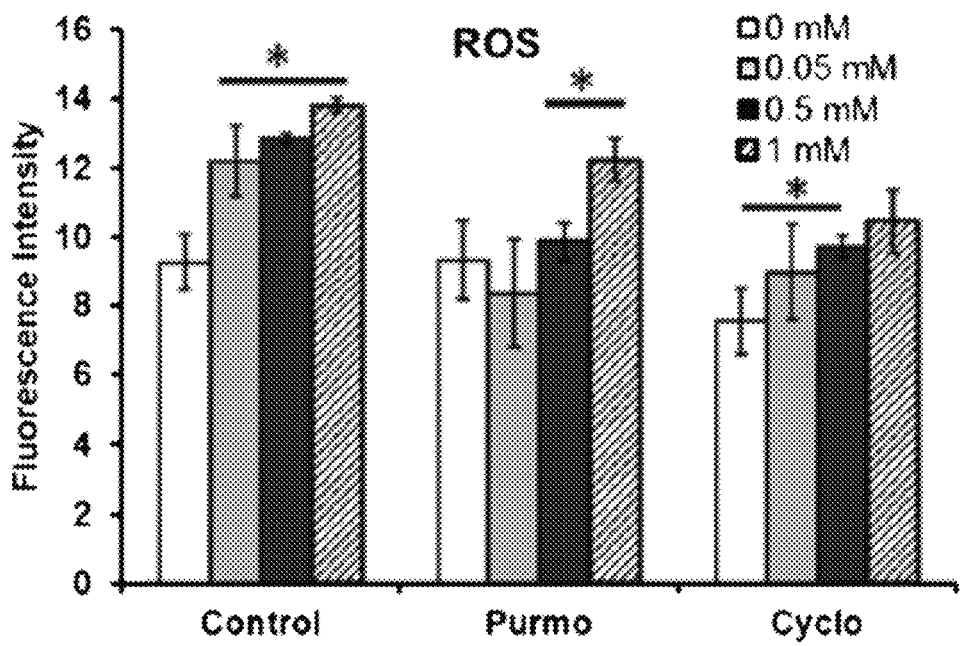

FIG. 72 is a graph showing N-methyl-D-aspartate (NMDA)-induced neurotoxicity and the influence of carbenoxolone treatment. Cells were contacted with NMDA and generation of reactive oxygen species was determined for control (untreated), Purmo-induced, and Cyclo-induced cells. * and ** indicate p-value<0.05.

Figure 73:
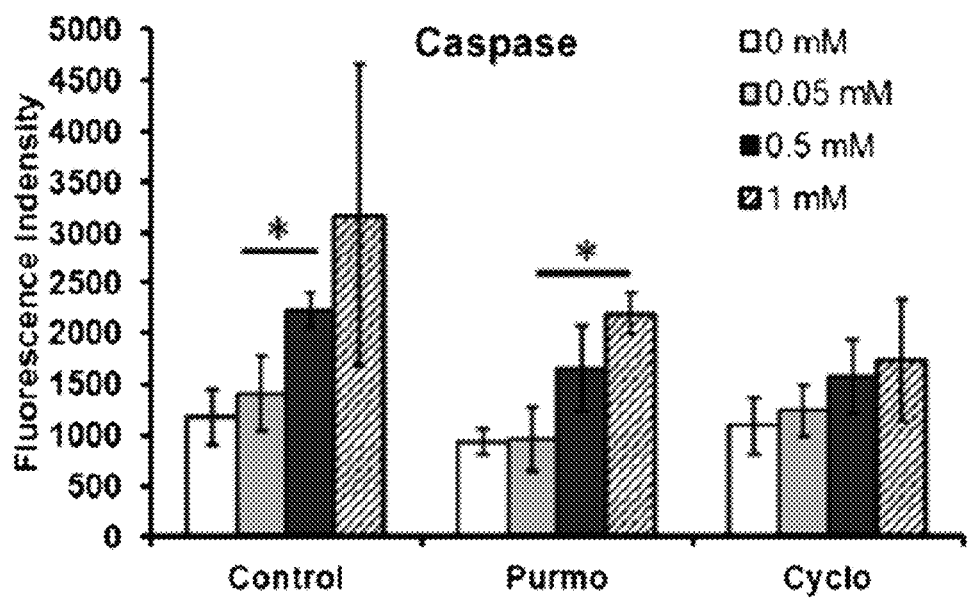

FIG. 73 is a graph showing N-methyl-D-aspartate (NMDA)-induced neurotoxicity and the influence of carbenoxolone treatment. Cells were contacted with NMDA and caspase levels were determined for control (untreated), Purmo-induced, and Cyclo-induced cells. * and ** indicate p-value<0.05.

Figure 74:
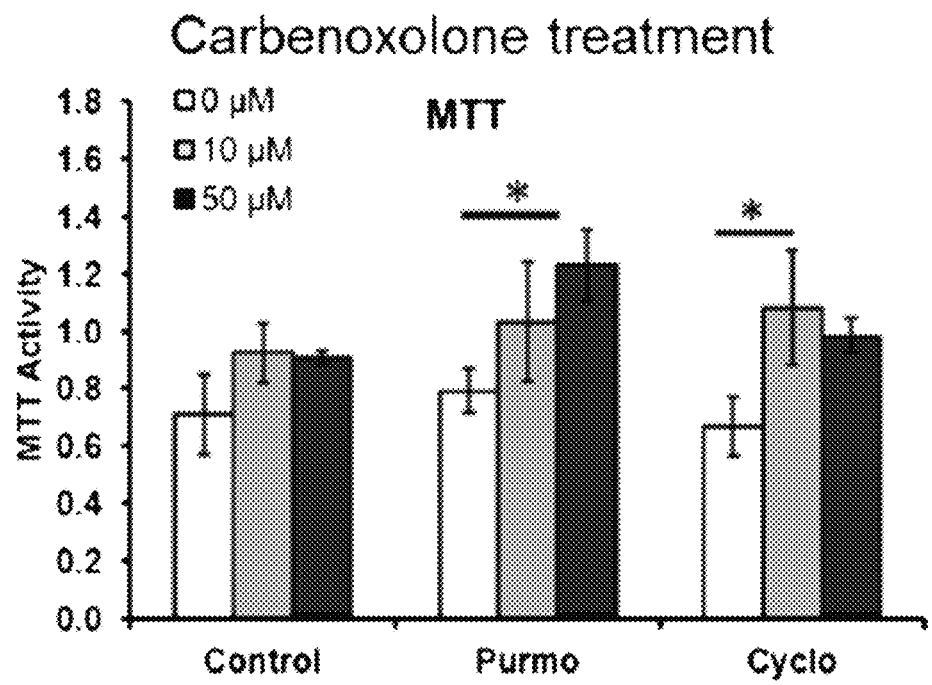

FIG. 74 is a graph showing N-methyl-D-aspartate (NMDA)-induced neurotoxicity and the influence of carbenoxolone treatment. Cells were contacted with NMDA, followed by carbenoxolone treatment, and metabolic activity (MTT assay) was determined for control (untreated), Purmo-induced, and Cyclo-induced cells. * and ** indicate p-value<0.05.

Figure 75:
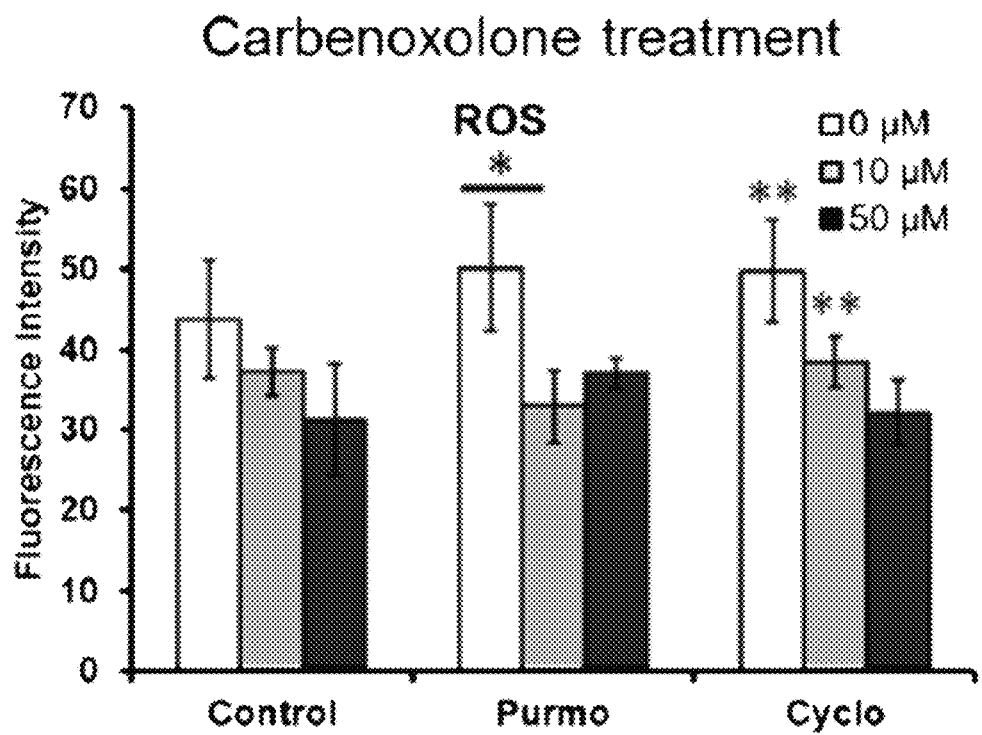

FIG. 75 is a graph showing N-methyl-D-aspartate (NMDA)-induced neurotoxicity and the influence of carbenoxolone treatment. Cells were contacted with NMDA, followed by carbenoxolone treatment, and generation of reactive oxygen species was determined for control (untreated), Purmo-induced, and Cyclo-induced cells. * and ** indicate p-value<0.05.

Figure 76:
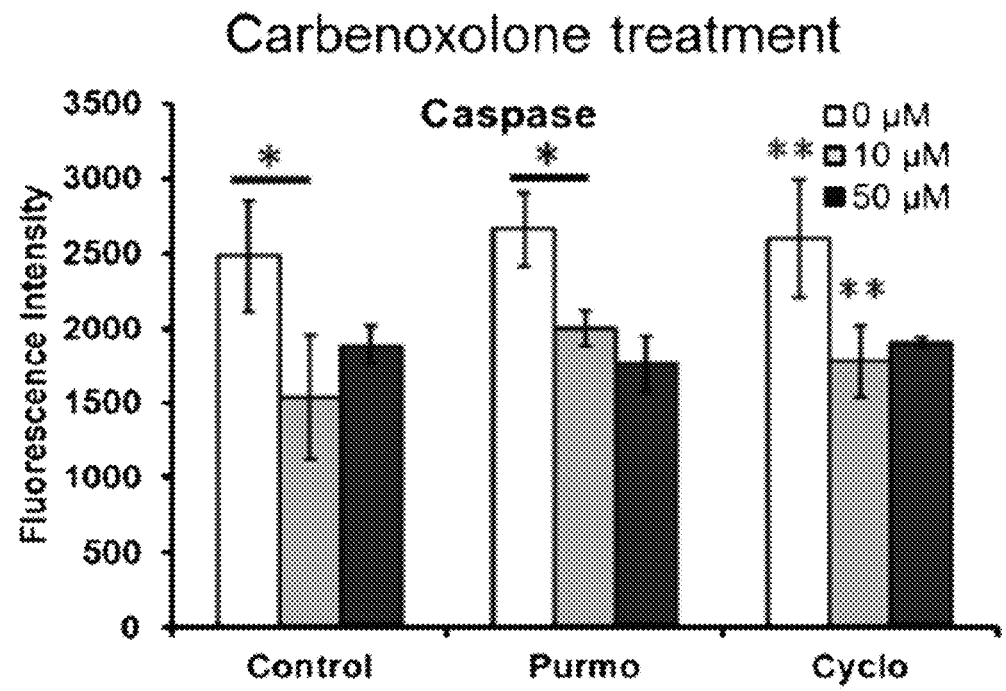

FIG. 76 is a graph showing N-methyl-D-aspartate (NMDA)-induced neurotoxicity and the influence of carbenoxolone treatment. Cells were contacted with NMDA, followed by carbenoxolone treatment, and caspase levels were determined for control (untreated), Purmo-induced, and Cyclo-induced cells. * and ** indicate p-value<0.05.

Figure 77:
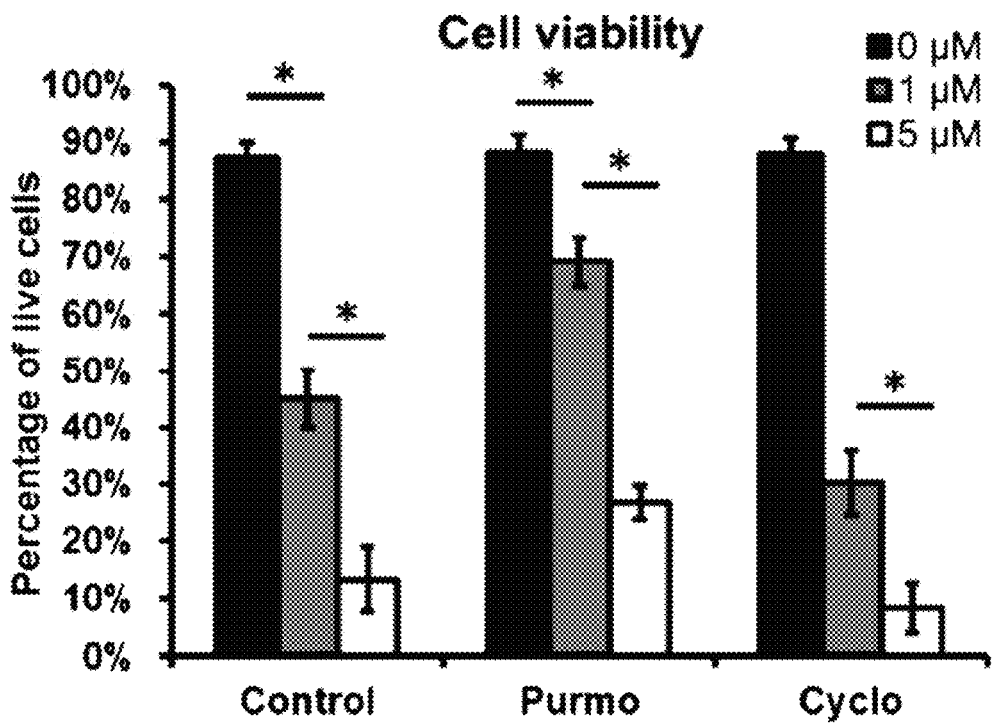

FIG. 77 is a graph showing $A\beta_{1-42}$ oligomer-induced cellular responses in neuronal cells derived from human iPSK3 cells. The day 35 cells were treated with $A\beta_{1-42}$ oligomer (1 or 5 μM) for three days and cell viability determined. Purmo: purmophamine group; Cyclo: cyclopamine group. Control: No growth factors. *p-value<0.05.

Figure 78:
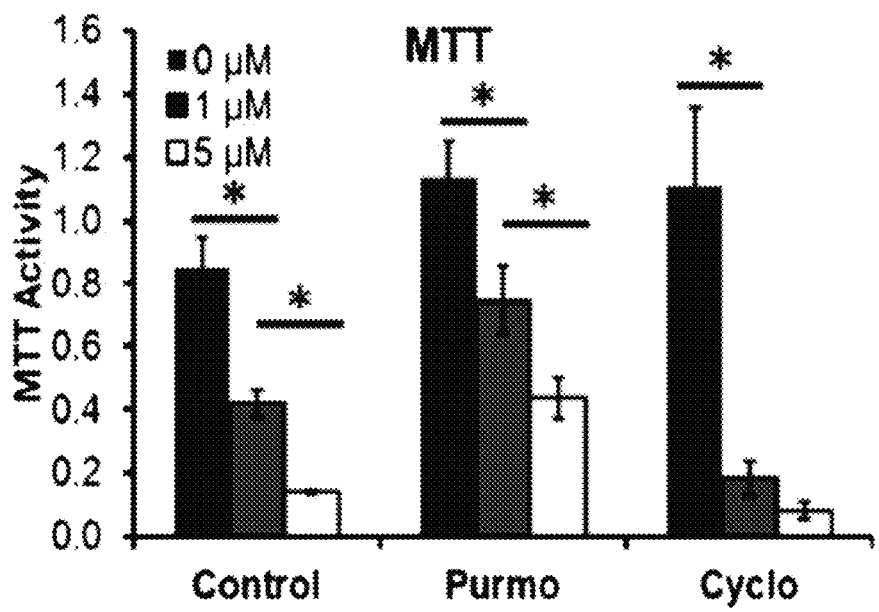

FIG. 78 is a graph showing $A\beta_{1-42}$ oligomer-induced cellular responses in neuronal cells derived from human iPSK3 cells. The day 35 cells were treated with $A\beta_{1-42}$ oligomer (1 or 5 μM) for three days and metabolic activity determined (MTT assay). Purmo: purmophamine group; Cyclo: cyclopamine group. Control: No growth factors. *p-value<0.05.

Figure 79:
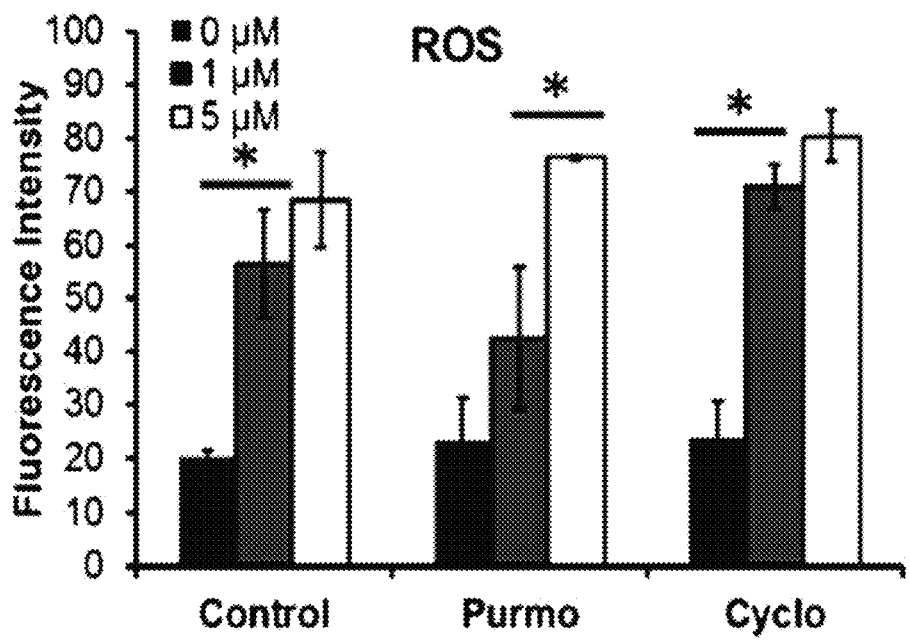

FIG. 79 is a graph showing $A\beta_{1-42}$ oligomer-induced cellular responses in neuronal cells derived from human iPSK3 cells. The day 35 cells were treated with $A\beta_{1-42}$ oligomer (1 or 5 μM) for three days and reactive oxygen species (ROS) levels determined. Purmo: purmophamine group; Cyclo: cyclopamine group. Control: No growth factors. *p-value<0.05.

Figure 80:
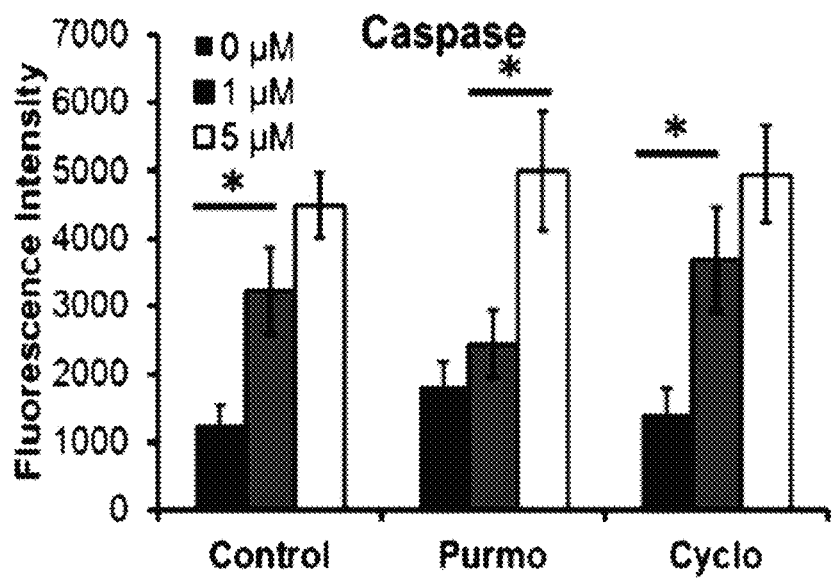

FIG. 80 is a graph showing $A\beta_{1-42}$ oligomer-induced cellular responses in neuronal cells derived from human iPSK3 cells. The day 35 cells were treated with $A\beta_{1-42}$ oligomer (1 or 5 μM) for three days and caspase expression determined. Purmo: purmophamine group; Cyclo: cyclopamine group. Control: No growth factors. *p-value<0.05.

Figure 81A:
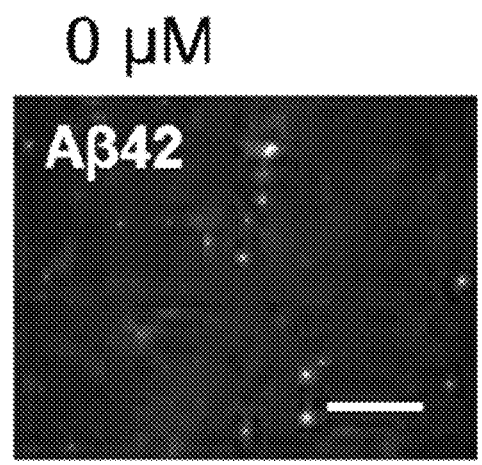

FIG. 81A is an image showing expression of amyloid β (Aβ) 42 on the day 42 cells (the Cyclo group). The cells were not treated with $A\beta_{1-42}$ oligomers (control) for three days. Representative fluorescent images are shown for Aβ42. Scale bar: 100 μm.

Figure 81B:
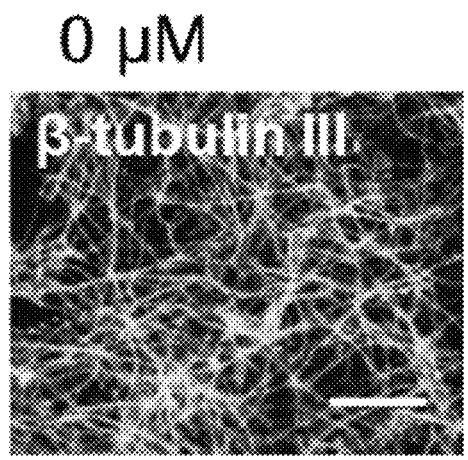

FIG. 81B is an image showing expression of amyloid β (Aβ) 42 on the day 42 cells (the Cyclo group). The cells were not treated with $A\beta_{1-42}$ oligomers (control) for three days. Representative fluorescent images are shown for β-tubulin III/Hoechst. Scale bar: 100 μm.

Figure 81C:
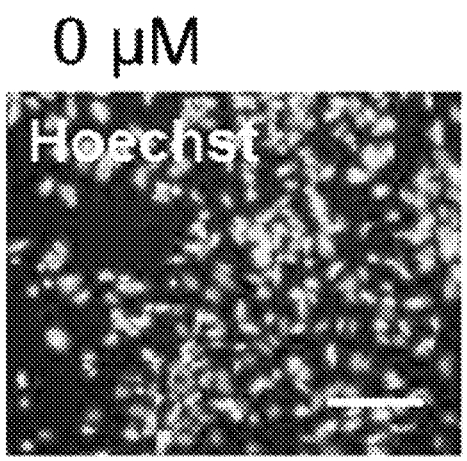

FIG. 81C is an image showing expression of amyloid β (Aβ) 42 on the day 42 cells (the Cyclo group). The cells were not treated with $A\beta_{1-42}$ oligomers (control) for three days. Representative fluorescent images are shown for Hoechst. Scale bar: 100 μm.

Figure 82A:
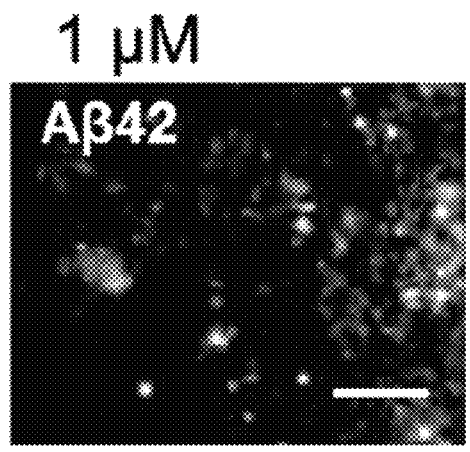

FIG. 82A is an image showing expression of amyloid β (AP) 42 on the day 42 cells (the Cyclo group). The cells were treated with 1 μM of $A\beta_{1-42}$ oligomers for three days. Representative fluorescent images are shown for Aβ42. Scale bar: 100 μm.

Figure 82B:
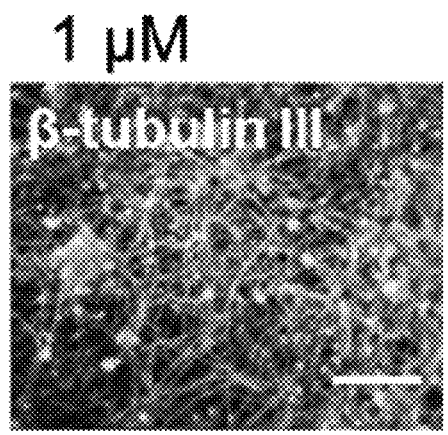

FIG. 82B is an image showing expression of amyloid β (Aβ) 42 on the day 42 cells (the Cyclo group). The cells were treated with 1 μM of $A\beta_{1-42}$ oligomers for three days. Representative fluorescent images are shown for β-tubulin III. Scale bar: 100 μm.

Figure 82C:
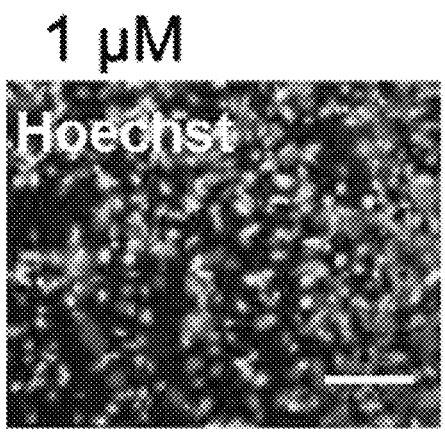

FIG. 82C is an image showing expression of amyloid β (Aβ) 42 on the day 42 cells (the Cyclo group). The cells were treated with 1 μM of $A\beta_{1-42}$ oligomers for three days. Representative fluorescent images are shown for Hoechst. Scale bar: 100 μm.

Figure 83A:
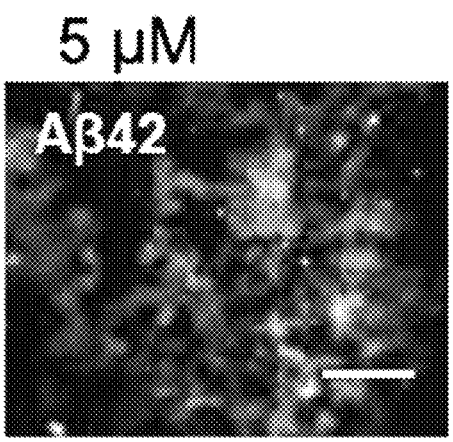

FIG. 83A is an image showing expression of amyloid β (Aβ) 42 on the day 42 cells (the Cyclo group). The cells were treated with 5 μM of $A\beta_{1-42}$ oligomers for three days. Representative fluorescent images are shown for Aβ42. Scale bar: 100 μm.

Figure 83B:
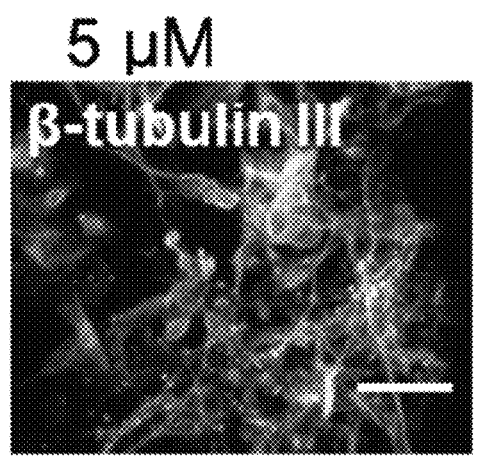

FIG. 83B is an image showing expression of amyloid β (Aβ) 42 on the day 42 cells (the Cyclo group). The cells were treated with 5 μM of $A\beta_{1-42}$ oligomers for three days. Representative fluorescent images are shown for β-tubulin III. Scale bar: 100 μm.

Figure 83C:
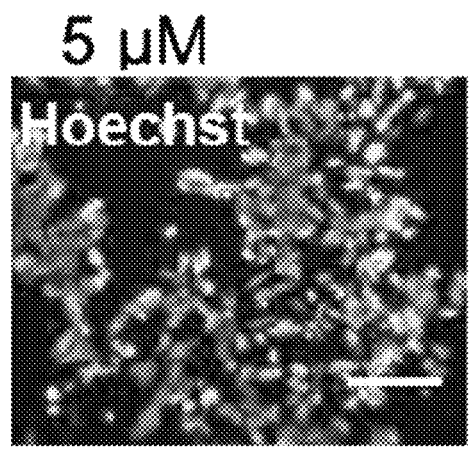

FIG. 83C is an image showing expression of amyloid β (Aβ) 42 on the day 42 cells (the Cyclo group). The cells were treated with 5 μM of $A\beta_{1-42}$ oligomers for three days. Representative fluorescent images are shown for Hoechst. Scale bar: 100 μm.

Figure 84:
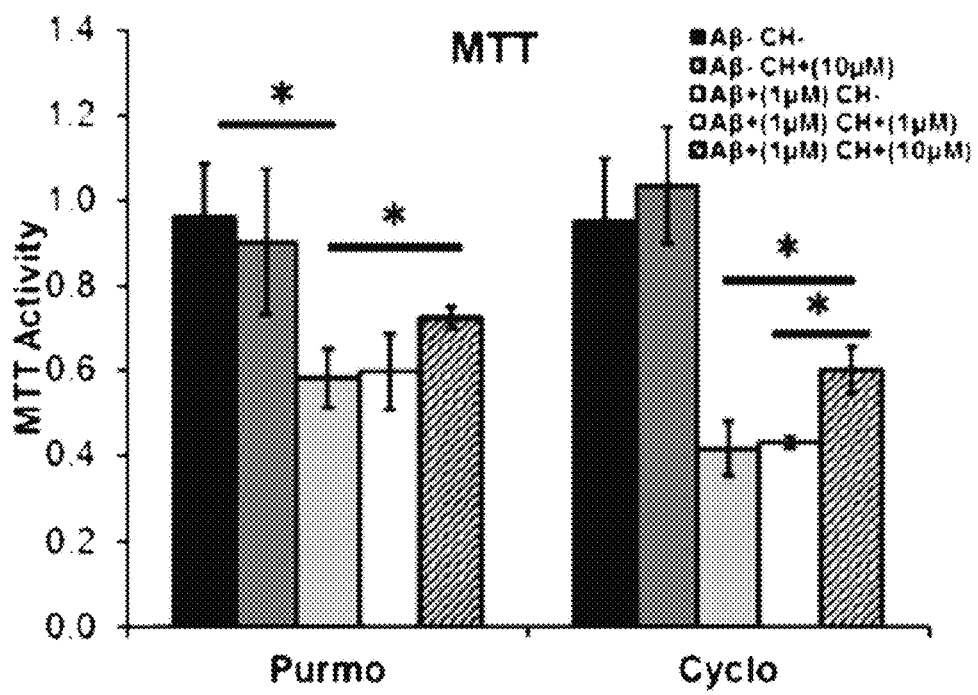

FIG. 84 is a graph showing $A\beta_{1-42}$ oligomer-induced synaptic activity and the effects of GSK-33 inhibitor. $A\beta_{1-42}$ oligomer-induced cellular response in the presence of GSK-3p inhibitor CHIR99021 (CH). The day 46 neural cells were treated with $A\beta_{1-42}$ oligomer (An, 1 μM) for 48 hours in the presence of CH at 1 or 10 μM. Cells were analyzed for mitochondrial activity (MTT activity). Aβ-CH−: no Aβ or CH was added; Aβ-CH+(10 μM): no Aβ but had 10 μM CH; Aβ+(1 μM)CH−: with 1 μM Aβ but no CH; Aβ+(1 μM)CH+(1 μM): with 1 μM Aβ and 1 μM CH; Aβ+(1 μM)CH+(10 μM): with 1 μM Aβ and 10 μM CH. *p-value<0.05.

Figure 85:
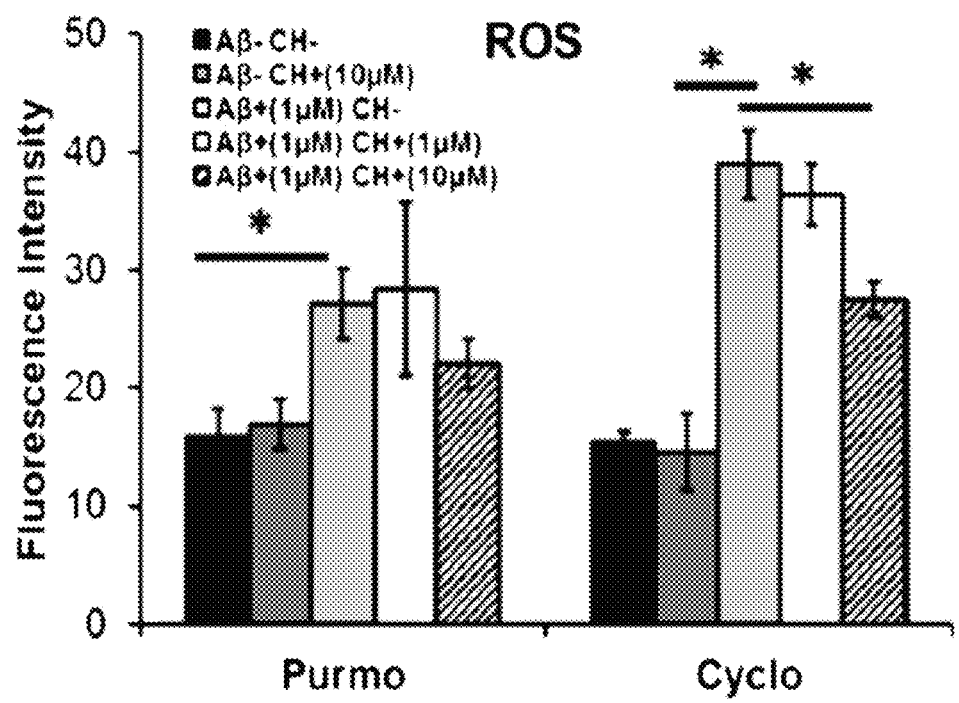

FIG. 85 is a graph showing $A\beta_{1-42}$ oligomer-induced synaptic activity and the effects of GSK-3β inhibitor. $A\beta_{1-42}$ oligomer-induced cellular response in the presence of GSK-3β inhibitor CHIR99021 (CH). The day 46 neural cells were treated with $A\beta_{1-42}$ oligomer (An, 1 μM) for 48 hours in the presence of CH at 1 or 10 μM. Cells were analyzed for ROS expression. Aβ-CH−: no AP or CH was added; Aβ-CH+(10 μM): no Aβ but had 10 μM CH; Aβ+(1 μM)CH−: with 1 μM Aβ but no CH; Aβ3+(1 μM)CH+(1 μM): with 1 μM Aβ and 1 μM CH; Aβ+(1 μM)CH+(10 μM): with 1 μM Aβ and 10 μM CH. *p-value<0.05.

Figure 86:
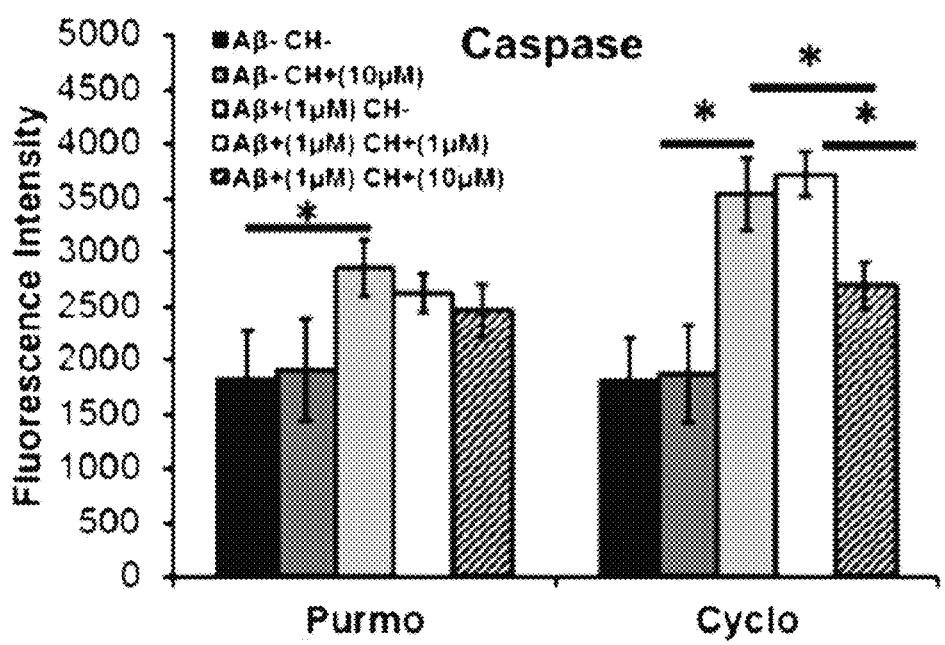

FIG. 86 is a graph showing $Aβ_{1-42}$ oligomer-induced synaptic activity and the effects of GSK-3β inhibitor. $Aβ_{1-42}$ oligomer-induced cellular response in the presence of GSK-33 inhibitor CHIR99021 (CH). The day 46 neural cells were treated with $Aβ_{1-42}$ oligomer (An, 1 μM) for 48 hours in the presence of CH at 1 or 10 μM. Cells were analyzed for caspase expression. Aβ-CH−: no Aβ or CH was added; Aβ-CH+(10 μM): no Aβ but had 10 μM CH; Aβ+(1 μM)CH−: with 1 μM Aβ but no CH; Aβ3+(1 μM)CH+(1 μM): with 1 μM Aβ and 1 μM CH; Aβ+(1 μM)CH+(10 μM): with 1 μM Aβ and 10 μM CH. *p-value<0.05.

DETAILED DESCRIPTION OF THE PREFERRED EMBODIMENT

As used herein, "treat", "treatment", "treating", and the like refer to acting upon a condition, such as a neurodegenerative disease, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing further neurodegenerative disease. Compositions according to the present invention may be used to effect a favorable change on immune cells, whether that change is an improvement, such as stopping or reversing the neurodegenerative disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into the cell model. For example, a xenobiotic may be added to the cell culture medium, and cells added to the medium, i.e. contacting the cells with the xenobiotic. In most instances, it is preferable for the cells of the present invention to be submerged in medium, and therefore all cells contacted by the xenobiotic. However, this is not required, and in other instances only a portion of the cell model is submerged in medium containing the xenobiotic.

The invention is further directed to a method of modeling neurons. Such models can be used for testing and screening treatments for neurodegenerative disease. Such methods include providing cells obtained by the induction methods described, and in some instances are exposed to a neurodegenerative agent, such as an amyloid protein, ischemic conditions (like a glucose oxygen deprival), neurodegenerative viruses or particles, such as HIV, prions and *Borrelia* bacteria, or neurodegenerative compounds, such as 1-methyl-4-phenyl-1,2,3,6-tetrahydropyridine (MPTP), N-methyl-D-aspartic acid (NMDA), methamphetamines, ketamine, phencyclidine (PCP), amphetamine, antipsychotics, benzodiazepine like Xanax. The cell model or models are contacted with potential treatments, which can be before the neurodegenerative agent, concurrently with the neurodegenerative agent, or after exposure to the neurodegenerative agent. Control can be used for comparison; such as models that are exposed to the neurodegenerative agent. Statistical analysis can be used to determine effectiveness of treatment.

Each experiment was carried out at least three times. The representative experiments were presented and the results were expressed as [mean±standard deviation]. To assess the statistical significance, one-way ANOVA followed by Fisher's LSD post hoc tests were performed. A p-value<0.05 was considered statistically significant.

Example 1

Human iPSK3 cells were derived from human foreskin fibroblasts transfected with plasmid DNA encoding reprogramming factors OCT4, NANOG, SOX2 and LIN28 (kindly provided by Dr. Stephen Duncan, Medical College of Wisconsin) (Si-Tayeb, et al., Generation of human induced pluripotent stem cells by simple transient transfection of plasmid DNA encoding reprogramming factors, BMC Dev Biol, 10 (2010) 81; Si-Tayeb, et al., Highly efficient generation of human hepatocyte-like cells from induced pluripotent stem cells, Hepatology, 51 (2010) 297-305). Human iPSK3 cells were maintained in mTeSR serum-free medium (StemCell Technologies, Inc., Vancouver, Canada) on growth factor reduced Geltrex (Life Technologies) (Yan, et al., Differential effects of acellular embryonic matrices on pluripotent stem cell expansion and neural differentiation, Biomaterials, 73 (2015) 231-242). The cells were passaged by Accutase every 5-6 days and seeded at $1×10^6$ cells per well of 6-well plate in the presence of 10 μM Y27632 (Sigma) for the first 24 hours. Two other media were also tested: StemPro serum-free medium (Life Technologies) and knockout serum replacement (SR) medium (80% DMEM, 20% knockout SR, 1 mM L-Glutamine, 0.1 mM β-mercaptoethanol, and 0.1 mM nonessential amino acids) supplemented with fibroblast growth factor (FGF)-2 (40 ng/mL).

Cells were analyzed by a fluorescent microscopy to determine optimum growth conditions. Briefly, the cells were fixed with 4% paraformaldehyde (PFA). The images from five independent fields (800-1000 cells) were captured using an Olympus microscope and analyzed using ImageJ software.

Figure 1:
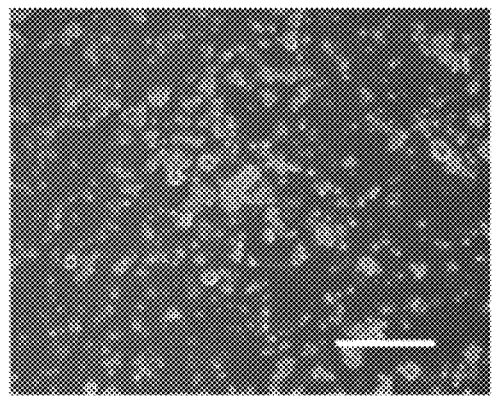
FIG. 1 is a phase contrast image of embryoid body (EB) formation from human iPSK3 cells grown in DMEM/F-12 plus 2% B27 medium. The EBs were then grown in StemPro medium conditions and the phase contrast image collected on day 1. The scale bar depicts 200 μm.
Figure 2:
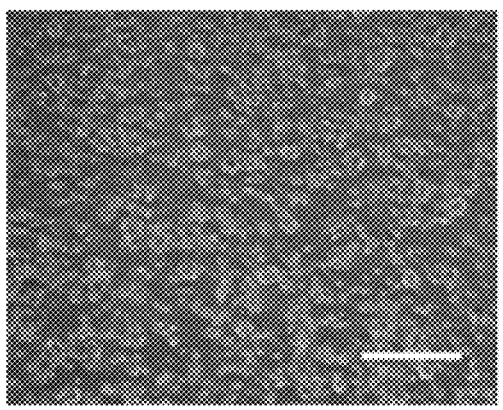
FIG. 2 is a phase contrast image of embryoid body (EB) formation from human iPSK3 cells grown in DMEM/F-12 plus 2% B27 medium. The EBs were then grown in SR medium conditions and the phase contrast image collected on day 1. The scale bar depicts 200 am.
Figure 3:
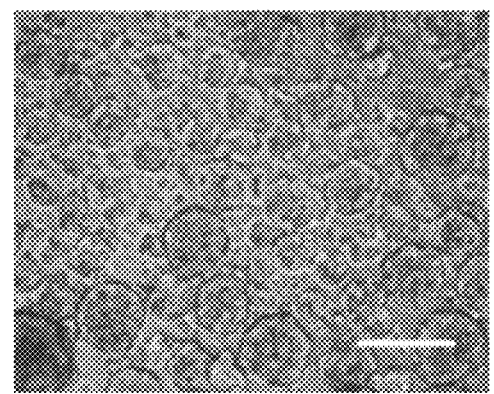
FIG. 3 is a phase contrast image of embryoid body (EB) formation from human iPSK3 cells grown in DMEM/F-12 plus 2% B27 medium. The EBs were then grown in mTeSR conditions and the phase contrast image collected on day 1. The scale bar depicts 200 μm.
Figure 4:
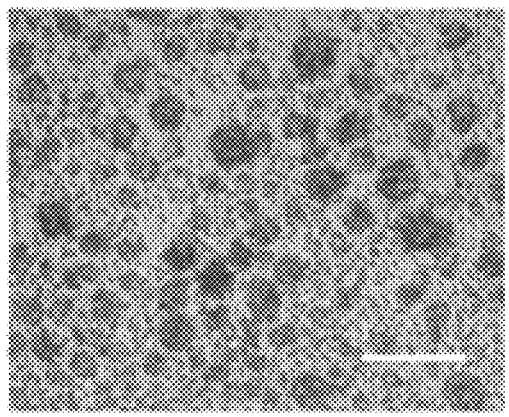
FIG. 4 is a phase contrast image of embryoid body (EB) formation from human iPSK3 cells grown in DMEM/F-12 plus 2% B27 medium. The EBs were then grown in StemPro medium conditions and the phase contrast image collected on day 2. The scale bar depicts 200 am.
Figure 5:
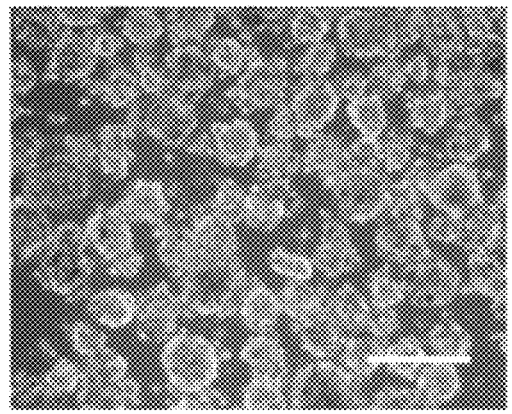
FIG. 5 is a phase contrast image of embryoid body (EB) formation from human iPSK3 cells grown in DMEM/F-12 plus 2% B27 medium. The EBs were then grown in SR medium conditions and the phase contrast image collected on day 2. The scale bar depicts 200 am.
Figure 6:
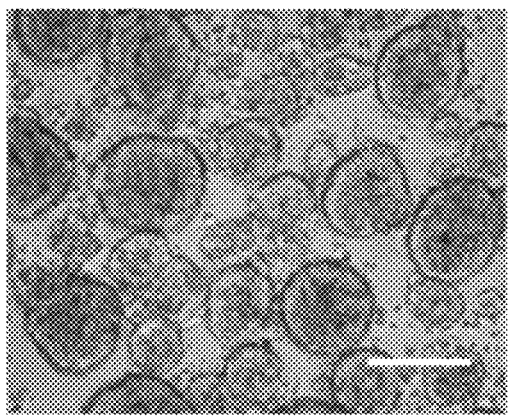
FIG. 6 is a phase contrast image of embryoid body (EB) formation from human iPSK3 cells grown in DMEM/F-12 plus 2% B27 medium. The EBs were then grown in mTeSR conditions and the phase contrast image collected on day 2. The scale bar depicts 200 lam.
Figure 7:
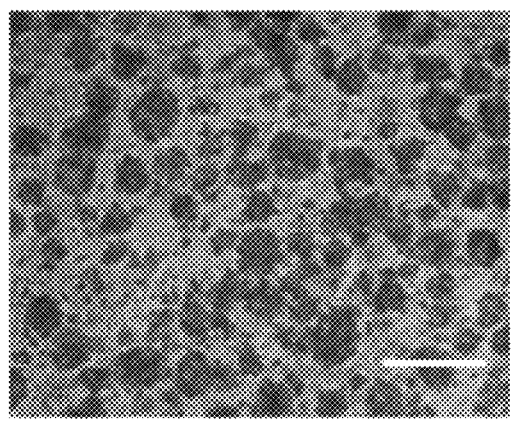
FIG. 7 is a phase contrast image of embryoid body (EB) formation from human iPSK3 cells grown in DMEM/F-12 plus 2% B27 medium. The EBs were then grown in StemPro medium conditions and the phase contrast image collected on day 3. The scale bar depicts 200 lam.
Figure 8:
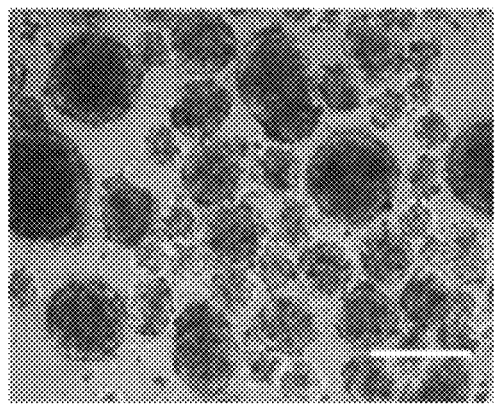
FIG. 8 is a phase contrast image of embryoid body (EB) formation from human iPSK3 cells grown in DMEM/F-12 plus 2% B27 medium. The EBs were then grown in SR medium conditions and the phase contrast image collected on day 3. The scale bar depicts 200 am.
Figure 9:
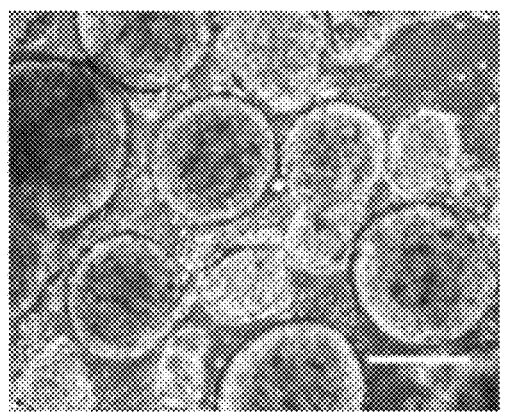
FIG. 9 is a phase contrast image of embryoid body (EB) formation from human iPSK3 cells grown in DMEM/F-12 plus 2% B27 medium. The EBs were then grown in mTeSR conditions and the phase contrast image collected on day 3. The scale bar depicts 200 μm.

Cells were plated into StemPro, as seen in FIG. 1, SR medium, as seen in FIG. 2, or mTeSR medium, as seen in FIG. 3. Dailey analysis of the medium, as seen in FIG. 4, FIG. 5, and FIG. 6 at day 2 for StemPro, SR medium, or mTeSR medium, respectively showed iPSK3 cells expanded in StemPro medium and SR medium formed smaller aggregates than those in mTeSR medium. By day 3, mTeSR medium showed good induced neural differentiation, as seen by erythroid body formation, as seen by FIG. 9, compared to FIGS. 7 and 8. As such, hiPSK3 cells were grown in mTeSR medium when generating models of the invention.

Example 2

Figure 10:
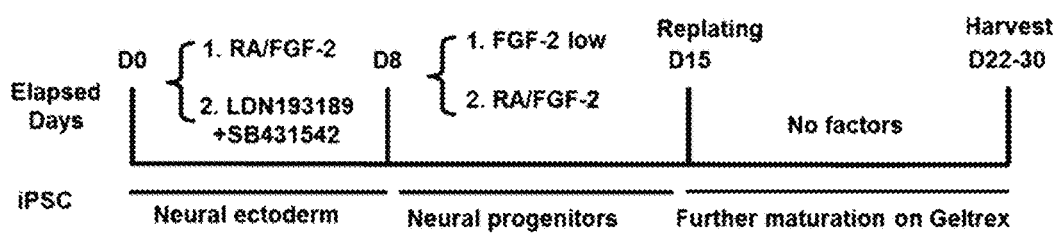
FIG. 10 is an illustration showing different methods of neural ectoderm induction during day 0-8.

The human iPSK3 cells were subjected to differentiation to determine ability to induce neuronal phenotypes. The cells were grown as outlaid in Example 1, and seeded into Ultra-Low Attachment (ULA) 24-well plates (Corning Inc., Corning, N.Y.) at $3 \times 10^5$ cells/well in differentiation medium composed of Dulbecco's Modified Eagle Medium/Nutrient Mixture F-12 (DMEM/F-12) plus 2% B27 serum-free supplement (Life Technologies). Y27632 (10 µM) was added during the seeding and removed after 24 hours. Two induction protocols were utilized, as seen in FIG. 10.

At day 1, the cells—which had formed embryoid bodies (EBs)—were treated with retinoic acid (RA) (2 µM, Sigma) and FGF-2 (25 ng/mL) (RA/FGF-2 protocol) (Nistor, et al., Derivation of high purity neuronal progenitors from human embryonic stem cells, PLoS One, 6 (2011) e20692) or with dual SMAD signaling inhibitors 10 µM SB431542 (Sigma; 4-(4-(benzo[d][1,3]dioxol-5-yl)-5-(pyridin-2-yl)-1H-imidazol-2-yl)benzamide) and 100 nM LDN193189 (Sigma; 4-[6-[4-(1-piperazyl)phenyl]pyrazol[1,5-a]pyrimidin-3-yl]-quinoline) (LDN/SB method) (Chambers, et al., Highly efficient neural conversion of human ES and iPS cells by dual inhibition of SMAD signaling, Nat Biotechnol, 27 (2009) 275-280). Control cells were treated with dual SMAD signaling inhibitors 10 µM SB431542 (Sigma) and 100 nM LDN193189 (Sigma) (Chambers, et al., Highly efficient neural conversion of human ES and iPS cells by dual inhibition of SMAD signaling. Nat Biotechnol. 2009; 27:275-80). After 8 days, for RA/FGF-2 protocol, RA was removed and FGF-2 was reduced to 10 ng/mL. For dual SMAD inhibition protocol, the cells were treated with different growth factor combinations; (1) no growth factors; (2) RA (2 µM) and FGF-2 (10 ng/mL); (3) FGF-2 (10 ng/mL) and cyclopamine (1 µM, Sigma, RA was not included to minimize caudalization effect); (4) FGF-2 (10 ng/mL), purmorphamine (1 µM, Sigma) and RA (2 µM); or FGF-2, purmorphamine, and RA plus CHIR99021 (3 µM) (Stanton & Peng, Small-molecule modulators of the Sonic Hedgehog signaling pathway, Mol Biosyst, 6 (2010) 44-54). After another 7-10 days in suspension, the 3-D NPC aggregates (day 15-18) were replated onto a Geltrex-coated surface and characterized at day 20.

Cells were analyzed using phase contrast microscopy, as described in Example 1 or immunohistochemistry. For immunocytochemistry, the cells were fixed with 4% paraformaldehyde (PFA) and permeabilized with 0.2-0.5% Triton X-100 for intracellular markers. The samples were then blocked (5% fetal bovine serum) and incubated with various mouse or rabbit primary antibodies, as provided for in Table 1. After washing, the cells were incubated with the corresponding secondary antibody: Alexa Fluor® 488 goat anti-Mouse IgG, Alexa Fluor® 488 or 594 goat anti-Rabbit IgG, or Alexa Fluor® 594 donkey anti-goat IgG (Life Technologies). The samples were stained with Hoechst 33342 and visualized under a fluorescent microscope (Olympus IX70, Melville, N.Y.). The images from five independent fields (800-1000 cells) were analyzed using ImageJ software. The proportion of positive cells was calculated based on the intensity of marker of interest normalized to the nuclear intensity, indicating the relative expression among different conditions.

TABLE 1

Antibody information and dilution factors.

| Cells | Primary Antibody | Origin/ Isotype | Supplier/Cat # | Dilution |
|---|---|---|---|---|
| Undifferentiated | Oct-4 | Mouse IgG1 | Millipore, MAB4419 | 1:500 |
| Neural progenitor | Nestin | Rabbit IgG | Sigma, N5413 | 1:100 |
| | Pax6 | Mouse IgG1 | Santa Cruz, sc-81649 | 1:100 |
| Neuron | β-tubulin III | Mouse IgG1 | Millipore, MAB1637 | 1:200 |
| Cortical neuron | TBR1 | Rabbit IgG | ABCAM, ab31940 | 1:200 |
| | BRN2 | Goat IgG | Santa Cruz, sc-6029 | 1:200 |
| | Glutamate | Rabbit IgG | Sigma, G6642 | 1:1000 |
| Motor neuron | Lim3 | Rabbit IgG | Millipore, AB3202 | 1:200 |
| | Islet-1 | Rabbit IgG | Millipore, AB4326 | 1:300 |
| | HB9 | Goat IgG | Santa Cruz, sc-22542 | 1:100 |
| Synaptic marker | Synapsin I | Rabbit IgG | Millipore, 574777 | 1:500 |
| | PSD95 | Rabbit IgG | Life Technologies, 51-6900 | 1:200 |
| Others | GABA | Rabbit IgG | Sigma, A2052 | 1:1000 |
| | GFAP | Mouse IgG1 | Millipore, MAB360 | 1:400 |
| | Amyloid β 42 | Rabbit IgG | ABCAM, ab10148 | 1:200 |
| Secondary | Alexa 488, goat anti-mouse IgG1 | — | Life Technologies, A-21121 | 1:200 |
| | Alexa 594, goat anti-rabbit IgG | — | Life Technologies, A-11012 | 1:400 |
| | Alexa 594, donkey anti-goat IgG | — | Life Technologies, A-11058 | 1:400 |

Figure 11A:
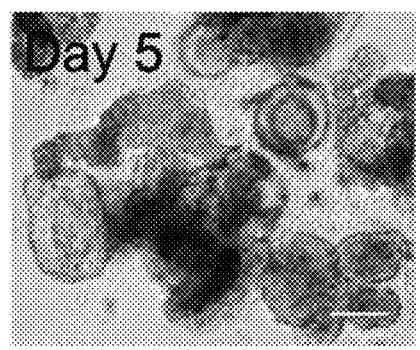
FIG. 11A is a phase contrast image showing neural ectoderm induction from hiPSK3 cells through EB formation. The image shows phase contrast of neural spheres and neural outgrowth for RA/FGF-2 methodology at day 5. Scale bar: 100 μm.
Figure 11B:
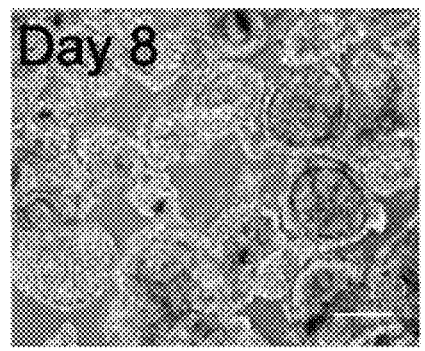
FIG. 11B is a phase contrast image showing neural ectoderm induction from hiPSK3 cells through EB formation. The image shows phase contrast of neural spheres and neural outgrowth for RA/FGF-2 methodology at day 8. Scale bar: 100 μm.
Figure 11C:
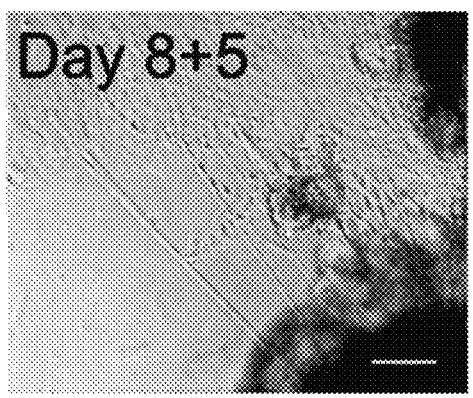
FIG. 11C is a microscopic image showing neural ectoderm induction from hiPSK3 cells through EB formation. The image shows phase contrast of neural spheres and neural outgrowth for RA/FGF-2 methodology replated at day 8 and grown for an additional 5 days. Scale bar: 100 μm.
Figure 12A:
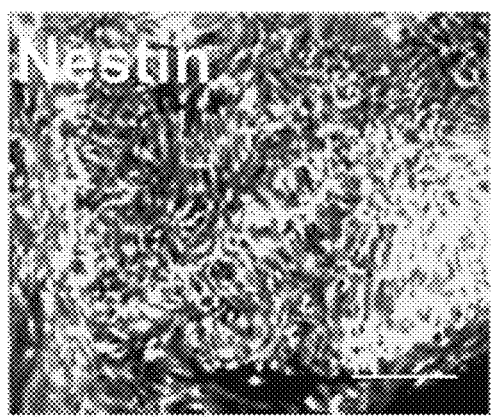
FIG. 12A is a microscopic image showing neural ectoderm induction from hiPSK3 cells through EB formation. The image shows phase contrast of neural spheres and neural outgrowth for RA/FGF-2 methodology. Cells were stained for nestin. Scale bar: 100 μm.
Figure 12B:
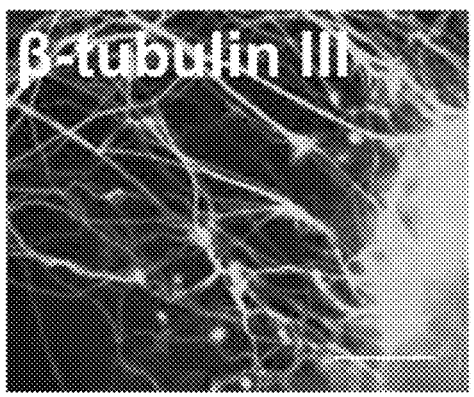
FIG. 12B is a microscopic image showing neural ectoderm induction from hiPSK3 cells through EB formation. The image shows phase contrast of neural spheres and neural outgrowth for RA/FGF-2 methodology. Cells were stained for β-tubulin III. Scale bar: 100 μm.
Figure 12C:
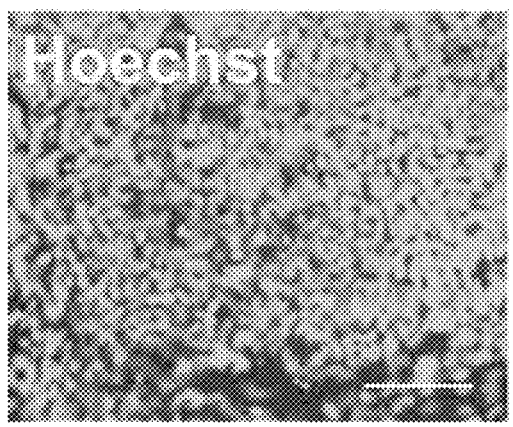
FIG. 12C is a microscopic image showing neural ectoderm induction from hiPSK3 cells through EB formation. The image shows phase contrast of neural spheres and neural outgrowth for RA/FGF-2 methodology. Cells were stained using Hoechst stain. Scale bar: 100 μm.
Figure 13A:
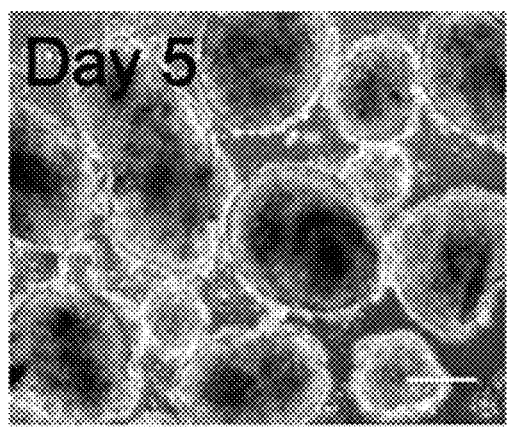
FIG. 13A is a microscopic image showing neural ectoderm induction from hiPSK3 cells through EB formation. The image shows phase contrast of neural spheres and neural outgrowth for LDN/SB methodology at day 5. Scale bar: 100 μm.
Figure 13B:
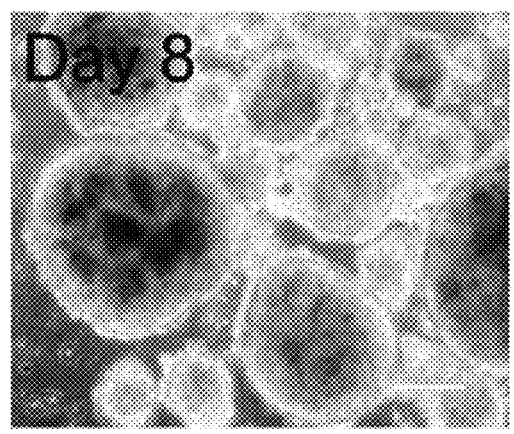
FIG. 13B is a microscopic image showing neural ectoderm induction from hiPSK3 cells through EB formation. The image shows phase contrast of neural spheres and neural outgrowth for LDN/SB methodology at day 8. Scale bar: 100 μm.
Figure 13C:
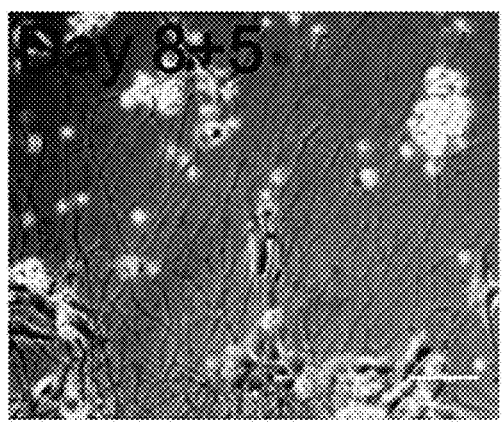
FIG. 13C is a microscopic image showing neural ectoderm induction from hiPSK3 cells through EB formation. The image shows phase contrast of neural spheres and neural outgrowth for LDN/SB methodology for cells replated at day 8 and grown for an additional 5 days. Scale bar: 100 μm.
Figure 14A:
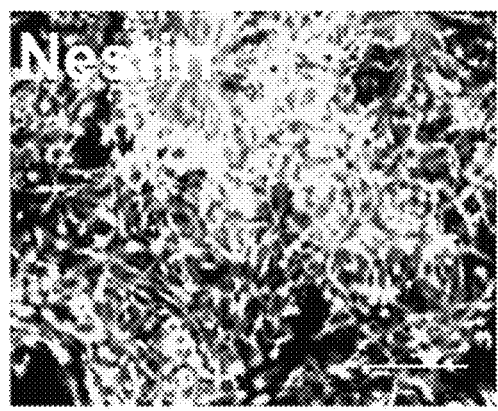
FIG. 14A is a microscopic image showing neural ectoderm induction from hiPSK3 cells through EB formation. The image shows phase contrast of neural spheres and neural outgrowth for LDN/SB methodology. Cells were stained for nestin. Scale bar: 100 μm.
Figure 14B:
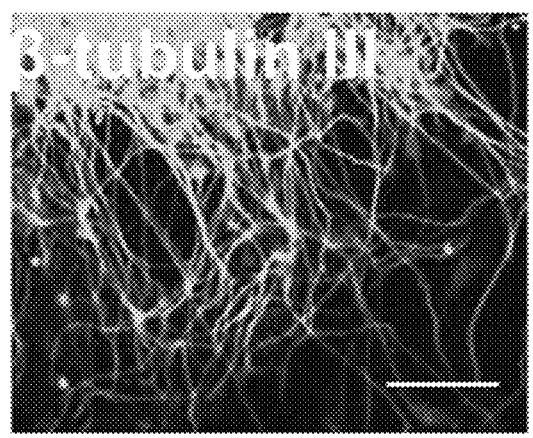
FIG. 14B is a microscopic image showing neural ectoderm induction from hiPSK3 cells through EB formation. The image shows phase contrast of neural spheres and neural outgrowth for LDN/SB methodology. Cells were stained for β-tubulin III. Scale bar: 100 μm.
Figure 14C:
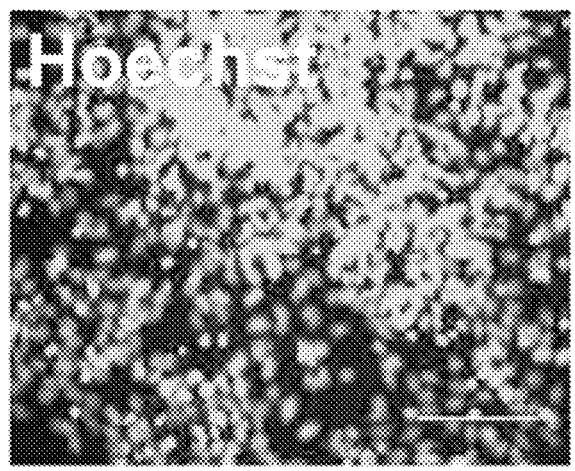
FIG. 14C is a microscopic image showing neural ectoderm induction from hiPSK3 cells through EB formation. The image shows phase contrast of neural spheres and neural outgrowth for LDN/SB methodology. Cells were stained using Hoechst stain. Scale bar: 100 μm.

The induction methods—RA/FGF-2 induction versus dual SMAD inhibition—were evaluated for neural ectoderm induction through EB-based differentiation. Both induction methods resulted in readily-formed EBs in suspension, which developed into NPC spheres during day 0-8. Images at day 5, as seen in FIG. 11A and FIG. 13A for RA/FGF-2 and LDN/SB, respectively. At day 8, phase contrast image, as seen in FIGS. 11B and 13B, were obtained. The images show the NPCs from LDN/SB induction appeared larger. After replating the day 8 NPCs for additional 5 days, phase contrast images show neural outgrowth from RA/FGF-2 and LDN/SB, as seen in FIGS. 11C and 13C. Nestin+ progenitors, shown in FIGS. 12A and 14A for RA/FGF-2 and LDN/SB, and β-tubulin III+ neuronal cells, shown in FIGS. 12B and 14B for RA/FGF-2 and LDN/SB, were observed in cultures induced by both methods. Hoescht staining show cell numbers in the image frame, which was slightly higher for RA/FGF-2 methodology, as seen in FIG. 12C compared to LDN/SB as seen in FIG. 14C.

The cells were next analyzed for neuronal marker expression. The cells were harvested by trypsinization and analyzed by flow cytometry (Sart, et al., Extracellular matrices decellularized from embryonic stem cells maintained their structure and signaling specificity, Tissue Eng Part A 20 (2014) 54-66; Sart, et al., Crosslinking of extracellular matrix scaffolds derived from pluripotent stem cell aggregates modulates neural differentiation, Acta Biomater, 30 (2016) 222-232). Briefly, 1×10$^6$ cells per sample were fixed with 4% PFA and washed with staining buffer (2% fetal bovine serum in phosphate buffered saline). The cells were permeabilized with 100% cold methanol, blocked, and then incubated with primary antibodies against Nestin, β-tubulin III, and Oct-4 followed by the corresponding secondary antibody, as provided for in Table 1. The samples were acquired with BD FACSCanto™ II flow cytometer (Becton Dickinson) and analyzed against isotype controls using FlowJo software.

Figure 15:
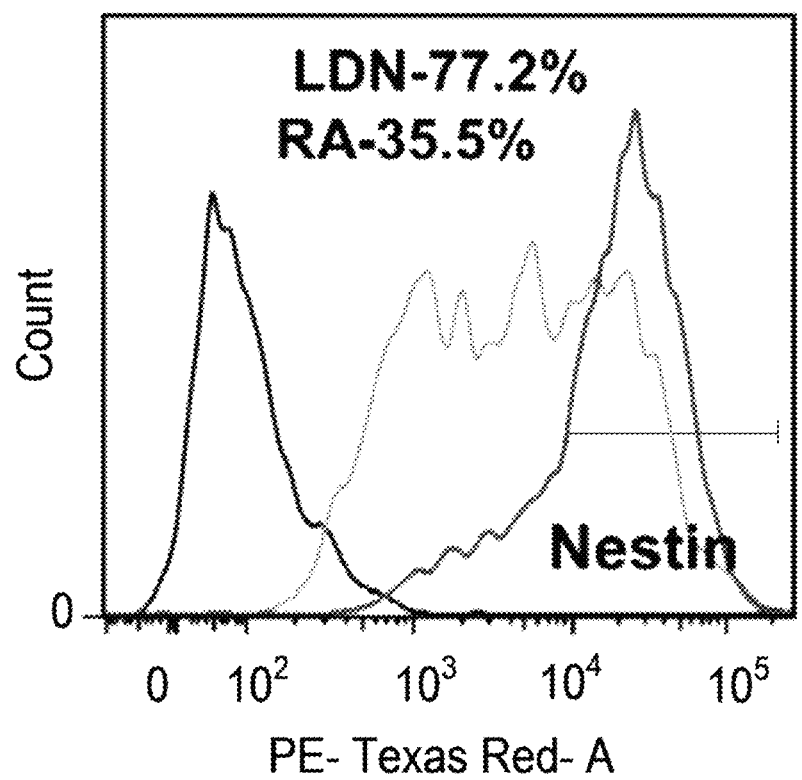
FIG. 15 is a graph showing representative flow cytometry histograms of Nestin expression. The black line (far left) represents the control, the drak gray line (far right) represents cells treated with LDN methods, and the light gray line (center) represents cells treated with RA methods.
Figure 16:
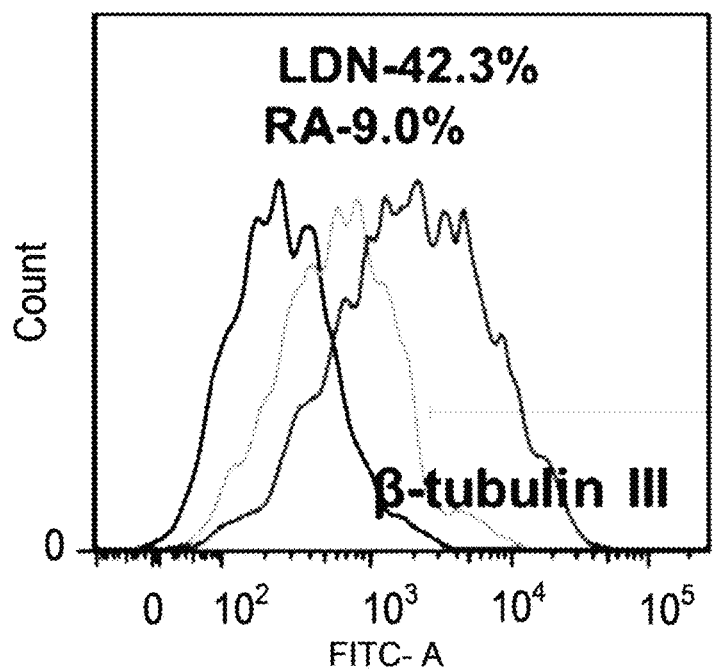
FIG. 16 is a graph showing representative flow cytometry histograms of β-tubulin III expression. The black line (far left) represents the control, the drak gray line (far right)

Flow cytometry of day 15 NPC spheres revealed higher Nestin and β-tubulin III expression with LDN/SB induction than RA/FGF-2 induction, as seen in FIG. 15 for Nestin and FIG. 16 for β-tubulin III. Quantification of the histograms showed LDN/SB induction resulted in significantly higher Nestin expression (73±6% vs. 46±14%) and β-tubulin III expression (41±2% vs. 11±3%) compared to RA/FGF-2 induction, as seen in FIG. 17.

The day 15 NPC spheres using LDN/SB induction were replated and further matured on Geltrex-coated surfaces for an additional 3 days. The cells expressed Nestin and Pax6 (with rosette morphology), as seen in FIGS. 18A through 18D. After another 15 days, the cells were observed to express multiple markers including Lim3 (a motor neuron marker) and glutamate (glutamatergic neurons), as seen in FIGS. 19A through 19D. Based on these results, the LDN/SB induction method was used in the subsequent experiments.

To perform long-term characterization of the induction methods, RA/FGF-2 induction versus dual SMAD inhibition, human iPSK3 cells were grown and induced using the methods as described above. At days 35-55, the neural progenitors were matured with brain-derived neurotrophic factor (BDNF) (10 ng/mL, R&D Systems) and gently passaged with trypsin once in two or three weeks with minimal pipetting. The replated cells consisted of the aggregates and the outgrowth of single cells.

Example 3

A neuronal model was prepared using LDN/SB induction, as discussed in Example 2. Neural patterning of hiPSCs was tuned through treatment with cyclopamine (the antagonist of SHH signaling) or purmorphamine (the agonist of SHH signaling) (Stanton & Peng, Small-molecule modulators of the Sonic Hedgehog signaling pathway, Mol Biosyst, 6 (2010) 44-54). The neuronal progenitors were patterned using different SHH-targeting molecules during days 8-16, as shown in FIG. 22. Briefly, human iPSK3 cells that had formed EBs and were treated with dual SMAD signaling inhibitors 10 μM SB431542 (Sigma) and 100 nM LDN193189 (Sigma) (Chambers, et al., Highly efficient neural conversion of human ES and iPS cells by dual inhibition of SMAD signaling, Nat Biotechnol, 27 (2009) 275-280). After 8 days, the cells were treated with different growth factor combinations: (1) no growth factors; (2) RA (2 μM) and FGF-2 (10 ng/mL); (3) FGF-2 (10 ng/mL) and cyclopamine (1 μM, Sigma). RA was not included to minimize caudalization effect; (4) FGF-2 (10 ng/mL), purmorphamine (1 μM, Sigma) and RA (2 lM); (5) FGF-2, purmorphamine, and RA plus CHIR99021 (3 μM) (Stanton & Peng, Small-molecule modulators of the Sonic Hedgehog signaling pathway, Mol Biosyst, 6 (2010) 44-54). After another 7-10 days in suspension, the 3-D neural progenitor cell (NPC) aggregates (day 15-18) were replated onto Geltrex-coated surface and characterized at day 20. For long-term characterizations at days 35-55, the neural progenitors were matured with brain-derived neurotrophic factor (10 ng/mL, R&D Systems) and gently passaged with trypsin once in two or three weeks with minimal pipetting. The replated cells consisted of the aggregates and the outgrowth The cells were prepared and analyzed using phase contrast microscopy, as discussed in Example 1. LDN/SB induction was performed, with the cells analyzed at days 1, 5, and 8 by phase contrast micorpscopy to confirm induction, as seen in FIGS. 23A, 23B, and 23C, respectively. The cells were treated with SHH-targeting molecules using cyclopamine/FGF-2 (Cyclo), purmorphamine/RA/FGF-2 (Purmo), and RA/FGF-2 as a control group. Control cells showed NPC spheres at day 15, as seen in FIG. 24. Treatment with Cyclo resulted in larger spheres and few cells outside the spheres, as seen in FIG. 25, whereas Purmo-treated cells more closely resembled control cells, as seen in FIG. 26. Replating of the cells resulted in alterations to neuronal progenitor patterning, as seen in FIG. 27 for control, versus FIG. 28 for Cyclo-treated cells and FIG. 29 for Purmo-treated cells.

The three groups—control of RA/FGF-2, Cyclo-treated, and Purmo-treated—were analyzed by immunohistochemistry using the conditions provided in Example 2. Analysis of the immunohistochemistry images showed that induction via all conditions caused the cells at day 20 expressed high levels of Nestin and Pax6 (0.60-0.85) and moderate levels of β-tubulin III (0.20-0.40), as seen in FIG. 30. At day 35, the patterning of differentiated cells was further examined using various neuronal markers, including glutamate for cortical glutamatergic neurons, Lim3 (progenitor stage) and HB9 (mature stage) for motor neurons, as seen in FIG. 31. The Cyclo condition resulted in a higher portion of glutamate-expressing neurons than the Purmo condition (0.66±0.10 vs. 0.16±0.07), whereas the Purmo group had more Lim3-expressing cells than the Cyclo group (0.56±0.01 vs. 0.46±0.02). Consistently, HB9 expression was higher for the Purmo group than the Cyclo group (0.24±0.01 vs. 0.03±0.01), as seen in FIG. 31. The cell population in RA/FGF-2 group was more similar to the Cyclo group, indicating that this condition favored the generation of cortical neurons (van den Ameele, et al., Thinking out of the dish: what to learn about cortical development using pluripotent stem cells, Trends Neurosci, 37 (2014) 334-342). Moreover, Oct-4 expression was analyzed. Undifferentiated cells exhibited substantial Oct-4 expression—an indicator of plurpotency during neural ectoderm induction and neural patterning—when compared to Hoechst background, as seen in FIGS. 32A and 32B. By comparison, LDN/SB induction showed very little Oct-4 expression, as seen in FIGS. 33A and 33B, as did RA/FGF-2 induction, as seen in FIGS. 34A and 34B. Differentiated cells for both Cyclo-treated cells, as seen in FIGS. 35A and 35B, and Purmo-treated cells, as seen in FIGS. 36A and 36B similarly exhibited significantly decreased Oct-4 expression. It was also noted that a few contaminating pluripotent cells were observed. Cells were further characterized by flow cytometry, as described above. Cells were exposed to differentiation agent—either Cyclo or Purmo. Flow cytometry was conducted 20 days after exposure. Analysis of the histogram indicates substantial overlap between the treatment groups and isotype control, as seen in FIG. 37, indicating that few residual Oct-4 positive cells were present and the differentiation of pluripotent cells was efficient.

Additional characterizations were performed on day 35 cells using neural patterning marker TBR1 (a deep cortical layer VI marker (van den Ameele, et al., Thinking out of the dish: what to learn about cortical development using pluripotent stem cells, Trends Neurosci, 37 (2014) 334-342)) and ISL1 (Islet-1, another marker for motor neurons (Qu, et al., High-efficiency motor neuron differentiation from human pluripotent stem cells and the function of Islet-1, Nat Commun, 5 (2014) 3449)), as seen in FIG. 38. Here, the Cyclo and Purmo groups were compared with RA/FGF-2 as well as no growth factor control (no GFs). Among the four groups, the Cyclo group had the highest portion of TBR1-expressing cells (0.59±0.03) while the Purmo group had the highest portion of ISL-expressing cells (0.68±0.04). The inclusion of CHIR was found to enhance motor neuron differentiation as indicated by the increased expression of ISL1 and HB9 for the day 42 cells, as seen in FIG. 39.

Characterizations of the derived neuronal cells were also performed at day 55, as seen in FIG. 40. While high levels of β-tubulin III$^+$ cells (0.83-0.88) were observed for both the Cyclo and the Purmo groups, the Cyclo group had higher glutamate expression than the Purmo group (0.82±0.06 vs. 0.26±0.08), and the Purmo group had higher ISL1 (0.59±0.03 vs. 0.29±0.07) and HB9 (0.36±0.04 vs. 0.07±0.02) expression than the Cyclo group. The cortical identity of the derived cells in the Cyclo group (day 42) was also confirmed by the expression of BRN2, a superficial cortical layer II-IV marker, as seen in FIGS. 41A through 41C. Additional characterization showed the presence of GABAergic interneurons and astrocytes in the derived population from the Cyclo group, as seen in FIGS. 42A and 42B.

Total RNA was isolated from neural cell samples for reverse transcription polymerase chain reaction (RT-PCR) analysis. RNA was obtained using the RNeasy Mini Kit (Qiagen, Valencia, Calif.) according to the manufacturer's protocol followed by the treatment of DNA-Free RNA Kit (Zymo, Irvine, Calif.). Reverse transcription was carried out using 2 mg of total RNA, anchored oligo-dT primers (Operon, Huntsville, Ala.), and Superscript III (Invitrogen, Carlsbad, Calif.) (according to the manufacturer). Primers specific for target genes were designed using the software Oligo Explorer 1.2 (Genelink, Hawthorne, N.Y.; Table 2). The gene β-actin was used as an endogenous control for normalization of expression levels. Real-time RT-PCR reactions were performed on an ABI7500 instrument (Applied Biosystems, Foster City, Calif.), using SYBR1 Green PCR Master Mix (Applied Biosystems). The amplification reactions were performed as follows: 2 min at 50° C., 10 min at 95° C., and 40 cycles of 95° C. for 15 sec and 55° C. for 30 sec, and 68° C. for 30 sec. Fold variation in gene expression was quantified by means of the comparative Ct method: $2^{-(C_{ttreatment}-C_{tcontrol})}$ based on the comparison of the target gene expression (normalized to β-actin) between the test samples and the reference sample.

TABLE 2

Primer sequences for target genes

| Gene | Forward primer (5'-3') | Reverse primer (5'-3') |
|---|---|---|
| TBR1 | TGCGCACCCACTCATTTT ATTT (SEQ ID NO: 1) | GGTCGGTGAGCTAATTGC AGA (SEQ ID NO: 2) |
| HOXB4 | AATTCCTTCTCCAGCTCC AAGA (SEQ ID NO: 3) | CCTGGATGCGCAAAGTTCA (SEQ ID NO: 4) |
| vGLUT1 | CCCCAATTCCTCGCACTT TAT (SEQ ID NO: 5) | GGGAAGGATCCCAGATTT TGA (SEQ ID NO: 6) |
| MNX1(HB9) | TGAAACTTGAAACCGCCT CTG (SEQ ID NO: 7) | AGCAGTTTGAACGCTCGT GAC (SEQ ID NO: 8) |
| β-actin | GTACTCCGTGTGGATCGG CG (SEQ ID NO: 9) | AAGCATTTGCGGTGGACG ATGG (SEQ ID NO: 10) |

Consistent with the immunohistochemical analysis, RT-PCR analysis showed that the Purmo group had higher gene expression of HOXB4 (3.5±0.2 vs. 1.4±0.1) and HB9 (5.2±0.5 vs. 0.6±0.1) than the Cyclo group, as seen in FIG. 43 and FIG. 44, respectively. By contrast, the Cyclo group had higher expression of TBR1 (29.5±1.0 vs. 5.8±0.4) and vGlut1 (22.0±0.5 vs. 19.9±0.2) than the Purmo group at day 35, as seen in FIG. 45 and FIG. 46, respectively. At day 45, the vGlut1 gene expression in the Cyclo group became 3-fold higher than the Purmo group, as seen in FIG. 47. Collectively, these results indicate that the Cyclo group enriches the population of cortical glutamatergic neurons while the Purmo group promotes the generation of motor neurons.

In the absence of patterning factors, gene expression of HOXB4 and HB9 increased by 5-7 folds from day 21 to day 35, while the increase of TBR1 and vGlut1 was 48-104 fold, as seen in FIG. 48 and FIG. 49, respectively, indicating that basal differentiation conditions favored the generation of cortical glutamatergic neurons. Therefore, additional factor CHIR99021 (CHIR, a Wnt activator) was included in the Purmo group (Maury, et al., Combinatorial analysis of developmental cues efficiently converts human pluripotent stem cells into multiple neuronal subtypes, Nat Biotechnol, 33 (2015) 89-96; Du, et al., Generation and expansion of highly pure motor neuron progenitors from human pluripotent stem cells, Nat Commun, 6 (2015) 6626).

The cells from all the groups expressed pre-synaptic marker synapsin I and post-synaptic marker PSD95, indicating the development of synaptic structure, as seen in FIG. 50A through FIG. 51C. Analysis of the images showed synapsin I strongly costained with β-tubulin III in undifferentiated (control) cells and cells treated with Purmo. However, while there was some costaining of synapsin I and β-tubulin III in Cyclo-treated cells, the amount of costaining was substantially less than in control and Purmo-treated cells (data not shown). PSD95 was found to associate with β-tubulin III, but possessed less correlation than synapsin I and β-tubulin III (data not shown).

Example 4

Glass spinner bioreactors (50 mL; Wheaton, #356875) were prepared for studying NPC differentiation and neural tissue patterning from hiPSCs. Prior to the inoculation, the vessel is immersed with 2 mL Sigmacote (Sigma, #SL2) overnight to avoid cell attachment on the glass surface. Then the vessel is dried at room temperature. The spinner bioreactor is autoclaved at 121° C. for 20 min before using.

Wheaton Micro-Stir platform (Wheaton, #W900701-A) was used for bioreactor culture. The Micro-Stir platform allows for the control of agitation speed and the pattern (e.g., intermittent agitation with different cycles) (Yan Y, Song L, Tsai A-C, Ma T, Li Y. Generation of neural progenitor spheres from human pluripotent stem cells in a suspension bioreactor. Methods Mol Biol. 2015; In Press). The Micro-Stir platform was put into a 37° C., 5% $CO_2$ incubator prior to setting up bioreactor culture.

Next, hiPSK3 cells were induced for neural differentiation and cortical spheroid formation in bioreactor culture. The bioreactor was inoculated with day 0 undifferentiated hiPSK3 single cell suspension in the presence of Y27632 [(+)-(R)-trans-4-(1-aminoethyl)-N-(4-pyridyl)cyclohexanecarboxamide dihydrochloride]; Ishizaki, et al., Pharmacological properties of Y-27632, a specific inhibitor of rho-associated kinases. Mol Pharmacol. 2000 May; 57(5); 976-83) or day 8 embryoid bodies (EBs) in parallel to static control. For undifferentiated cells, the seeding density was $4.0-4.5 \times 10^5$ cells/mL. For EB inoculation, the EBs formed with the equivalent cell density in static culture were put in the bioreactor. The working volume of the bioreactor was 15 mL. After single cell inoculation, the bioreactor was agitated at an intermittent mode (15 min-on, 15 min-off cycle for 6 hours) at 80 rpm. After that, constant agitation (100 rpm) was maintained until the harvest time (7 or 22 days in bioreactor). For EB inoculation, the bioreactor was agitated at constant speed (100 rpm) until the harvest time (day 27-43). Complete medium change was performed every 3-4 days. During the culture time, samples were taken to monitor aggregate size distribution, glucose consumption and lactate production. The harvested aggregates were either replated onto a Geltrex-coated surface for another 4-7 days for immunocytochemistry, flow cytometry, or RT-PCR analysis, or kept in low attachment plates (up to total 71 days of culture) for confocal microcopy analysis.

Medium was moved through the bioreactor Wheaton Micro-Stir platform. The stirred suspension bioreactor provides macroscopic flow (3-15 dyne/cm$^2$), which can control aggregate size and also provides interstitial flow inside the aggregates and promotes nutrient diffusion. It is noted that blood flow also can lead to the shear stress above 10 dyne/cm$^2$ on endothelial cells. The PSC aggregate porosity is estimated to be about 0.22-0.25 (Wu J, Rostami M R, Cadavid Olaya D P, Tzanakakis E S. Oxygen transport and stem cell aggregation in stirred-suspension bioreactor cultures. PLoS One. 2014; 9:e102486). If the aggregate surface experience 3-15 dyne/cm$^2$, the flow penetration into the aggregates (tissue-like structure) will be at interstitial level (0.1-0.2 dyne/cm$^2$) due to the resistance from ECMs. In vitro cultured aggregates have no vascular structure. Therefore, nutrient delivery is realized through external agitation or perfusion.

Maturation of cortical organoids derived from hiPSK3 cells was performed in a spinner bioreactor compared to static 24-well plate culture, as seen in FIGS. 52A and 52B. The deep cortical layer of TBR1$^+$ cells (layer VI) appeared first, followed by the SATB2$^+$ (layer II-IV) superficial layer cells (according to "inside-out" cortical developmental strategy), showing the identity of cortex tissue, as seen in 53A and 53B. Prolonged culture was performed up to day 71 to obtain distinct cortical layer structure, as seen in FIG. 53A. The cells from cortical organoids displayed appropriate neural markers (e.g., β-tubulin III) and synaptic activity, as seen in FIG. 54 compared to FIG. 55. The bioreactor culture demonstrated faster cortical development indicated by the higher TBR1 expression (RT-PCR), as seen in FIG. 56, and SATB2 expression (flow cytometry), as seen in FIG. 57, compared to static culture.

Example 5

Cells were differentiated as discussed in Example 1. Cellular morphology was confirmed using phase contrast microscopy methodology discussed above (data not shown). Whole-cell recording was conducted on the cells after 30-50 days of differentiation. Patch electrodes with resistances of 4-8 MΩ were pulled from borosilicate glass and fire-polished. Current and voltage traces were digitized at 20 kHz and filtered at 1 kHz respectively with an Axopatch 200B amplifier. Data acquisition and analysis were performed with pCLAMP10 software (Molecular Devices). The bath solution contained 2 mM KCl, 148 mM NaCl, 2 mM $MgCl_2$, 10 mM HEPES and 1 mM EGTA, pH 7.4. The pipette solution contained 130 mM KCl, 10 mM HEPES and 5 mM EGTA, pH 7.4. Na$^+$ and K$^+$ currents were evoked by voltage-clamp steps from −60 mV to +70 mV in 10 mV increments. Action potentials were elicited by current-clamp steps from −60 pA to +120 pA in 20 pA increments. Spontaneous post-synaptic currents were recorded in voltage-clamp configuration at a holding potential of −80 mV.

Cells were induced and differentiated using Purmo-methodology, described above. At day 50, patch clamp studies were performed to determine the electrophysiology of the replated neural aggregates. Electrophysiological assessments demonstrated several functional neural activities for the cells in the Purmo group, including that the cells exhibited fast-inactivating Na$^+$ currents followed by long-lasting outward K$^+$ currents, as seen in FIG. 58. Further, an analysis of the voltage gated ion channels shows cell excitability, as seen in FIG. 59 and FIG. 60. It was also noticed that the cells were able to generate action potentials in response to depolarizing current injections (point I), as well as at the end of hyperpolarizing current injections ("rebound" action potentials, point II), as seen in FIG. 61. The cells also displayed spontaneous excitatory post-synaptic currents (EPSCs), as seen in FIG. 62, suggesting a functional connectivity (synapse formation) between neurons. Similar electrophysiology was observed in neuronal cells for the Cyclo-treated cells at day 35, as seen in FIG. 63 for the ion currents and FIG. 64 for the action potential. These results indicate that the derived neuronal cells display appropriate currents, action potentials, and synaptic activities.

Example 6

The activities of MMPs influence neural progenitor cell proliferation, migration, and lineage commitment (Ethell & Ethell, Matrix metalloproteinases in brain development and remodeling: synaptic functions and targets, J Neurosci Res, 85 (2007) 2813-2823 (Ethell & Ethell, Matrix metalloproteinases in brain development and remodeling: synaptic functions and targets, J Neurosci Res, 85 (2007) 2813-2823; Barkho, et al., Endogenous matrix metalloproteinase (MMP)-3 and MMP-9 promote the differentiation and migration of adult neural progenitor cells in response to chemokines, STEM CELLS, 26 (2008) 3139-3149; Tonti, et al., Neural stem cells at the crossroads: MMPs may tell the way, Int J Dev Biol, 53 (2009) 1-17; Van Hove, et al., An aberrant cerebellar development in mice lacking matrix metalloproteinase-3, Mol Neurobiol, 45 (2012) 17-29; Szymczak, et al., Effect of matrix metalloproteinases inhibition on the proliferation and differentiation of HUCB- NSCs cultured in the presence of adhesive substrates, Acta Neurobiol Exp (Wars), 70 (2010) 325-336). The effects of MMP-2 inhibitor (ARP 100), MMP-9 inhibitor I, and MMP-2/MMP-9 inhibitor (SB-3CT) on different cell populations from the Cyclo group and the Purmo group were evaluated Derived neural cells, as described above, were replated onto Geltrex-coated 96-well plate and treated with MMP inhibitors: ARP 100 (MMP-2 inhibitor), MMP-9 inhibitor I, or SB-3CT (MMP-2 and MMP-9 inhibitor) (all from Santa Cruz) at 1 µM.

The cells were then characterized by MTT, reactive oxygen species (ROS), and poly caspase assays. For some experiments, cell numbers were counted using hemocytometer after trypsin/EDTA dissociation.

Morphological assessment using phase contrast microscopy indicated the reduction of neurite density after SB-3CT and MMP-9 inhibitor I treatment for the Purmo group (with more motor neurons), while neurite density had little changes for the Cyclo group (with more cortical glutamatergic neurons), as seen in FIGS. 65A and 65B for SB-3CT, FIGS. 66A and 66B for MMP-9 inhibitor, and FIGS. 67A and 67B for MMP-2 inhibitor ARP 100, compared to cells not exposed to MMP inhibitor, as seen in 68A and 68B. Furthermore, MTT assay and cell counting were performed to quantify the effects of MMP-2/-9 inhibition. MMP inhibition by SB-3CT and MMP-9 inhibitor I reduced MTT activity by 30-48% on day 20-25, as seen in FIG. 69, or decreased cell numbers by 16-24% as on day 45-50, seen in FIG. 70, for the Purmo group. However, MTT activity and cell numbers were comparable for all the conditions when neuronal cells of the Cyclo group were treated. These results demonstrate that differential reponses to MMP-2/-9 inhibitors exist for different neuronal subtypes, and the Purmo group is more sensitive than the Cyclo group.

Example 7

The hiPSC-derived neural cells were tested to determine response to different drugs and small molecules. Neural cells were formed as described in Example 2. After differentiation, the derived neural cells were replated onto Geltrex-coated 96-well plate and treated with N-methyl-D-aspartate (NMDA) at 0, 0.05, 0.5, 1 mM to mimic general neural toxicity. Cells were tested to determine response to neural protective molecules. Carbenoxolone (Cx, Sigma) (Beraki, et al., A pharmacological screening approach for discovery of neuroprotective compounds in ischemic stroke, PLoS One, 8 (2013) e69233) was added at different doses (0, 10 lM, 50 lM) of Cx were added with 0.5 mM NMDA for the first 24 h. Then samples were washed with phosphate buffer and the same doses of Cx were added for another 24 h. The cells were then characterized by MTT, reactive oxygen species (ROS), and poly caspase assays.

Briefly, the replated neural cells were incubated with 5 mg/mL 3-(4,5-Dimethylthiazol-2-yl)-2,5-diphenyltetrazolium bromide (MTT, Sigma) solution. The absorbance was measured at 500 nm using a microplate reader (Biorad, Richmond, Calif.). Image-iT™ Live Green Reactive Oxygen Species Detection kit (Molecular Probes) was used to detect the intracellular ROS. Briefly, neural cells were seeded at $1\times10^5$/mL in 96-well plates (100 µL). After 3 days, the cells were rinsed with Hank's balanced salt solution and incubated with 25 µM carboxy-$H_2$DCFDA for 30 min at 37° C. The samples were washed and measured under a fluorescence microplate reader using 488 nm excitation wavelength and 530 nm for emission (Bio-Tek, FLx800, Winoosk, Vt.). Image-iT™ Live Green Poly Caspase Detection kit (Molecular Probes) was used to detect the expression of caspases. The replated cells were incubated for one hour with the fluorescent inhibitor of caspases reagent and analyzed by a fluorescence microplate reader.

General neural toxicity was induced by NMDA exposure. MTT activity was reduced (by 30-50%) in the presence of NMDA (0.5 or 1 mM) for neuronal cells from all the three groups, as seen in FIG. 71. The expression of ROS in the cells increased logarithmically with increasing NMDA, as seen in FIG. 72, and corresponded to the decrease in MTT activity. Similarly, caspase activity showed a logarithmic relationship with NMDA concentration, as seen in FIG. 73. These results indicate that different neuronal subtypes similarly respond to NMDA that induces general neurotoxicity. Then, the neuroprotective effect of carbenoxolone, a gap junction blocker and modulator of 11-β-hydroxysteroid dehydrogenases (Beraki, et al., A pharmacological screening approach for discovery of neuroprotective compounds in ischemic stroke, PLoS One, 8 (2013) e69233), was evaluated after 24-hr exposure to 0.5 mM NMDA. Exposure of cells to NMDA and carbenoxolone treatment (10 or 50 µM) showed an increase in MTT activity (by 28-56%), as seen in FIG. 74. NMDA exposure with the carbenoxolone treatment resulted in reduced expression of ROS, as seen in FIG. 75. Similarly, caspase activity decreased for all the three groups with carbenoxolone treatment, as seen in FIG. 76. These results indicate that carbenoxolone provides neural protection from NMDA-induced neurotoxicity for the cell populations in all three conditions.

Example 8

The hiPSC-derived neural cells were tested to determine response to neurotoxic molecules and characterize the model. Neural cells were formed as described in Example 2. After differentiation, the derived neural cells were replated onto Geltrex-coated 96-well plate and treated with $A\beta_{1-42}$ oligomer.

To prepare oligomers of $A\beta_{1-42}$ peptide, biotinylated $A\beta_{1-42}$ (Bachem) was fully dissolved at 0.5 mg/mL in hexafluor-2-propanole (HFIP, Sigma) (Zhang, et al., A 3D Alzheimer's disease culture model and the induction of P21-activated kinase mediated sensing in iPSC derived neurons, Biomaterials, 35 (2014) 1420-1428). 10 µL of HFIP $A\beta_{1-42}$ solution was dispensed into siliconized Snap-Cap microtube, put in a desiccator to completely evaporate HFIP and thereafter stored at −80° C. Oligomer solutions were prepared freshly for each experiment. The stock was dissolved in 10 µL of DMSO (to 105 µM) and incubated for 3 hours at room temperature. Oligomers of $A\beta_{1-42}$ were added to the neural cultures derived from human iPSK3 cells at 0, 1 and 5 µM. The cells were evaluated for viability using Live/Dead® staining kit (Molecular Probes).

After 72 hours of exposure to the amyloid protein ($A\beta_{1-42}$), the cells were incubated in DMEM-F12 containing 1 µM calcein AM and 2 µM ethidium homodimer for 30 min. The samples were imaged under a fluorescent microscope. Using ImageJ software, the viability was analyzed and calculated as the percentage of green intensity over total intensity (including both green cells and red cells).

Significant cell death was observed following 5 µM $A\beta_{1-42}$ oligomer treatment, as seen in FIG. 77. At 1 µM, differential cell death was observed for different neuronal subtypes. Cyclopamine-induced cortical neurons were more sensitive to $A\beta_{1-42}$ treatment with more cell death and lower viability than purmorphamine-induced motor neurons (30.2±5.6% vs. 69.2±4.1% in viability, respectively). As shown in the figure, there was minimal cell death at 0 µM in all three samples (control, purmorphamine, cyclopamine), whereas by 1 µM the control and cyclopamine showed considerable cell death.

The cells were subsequently characterized by MTT, ROS, and poly caspase assays (Yan, et al., Cryopreservation of embryonic stem cell-derived multicellular neural aggregates labeled with micron-sized particles of iron oxide for magnetic resonance imaging, Biotechnol Prog, 31 (2015) 510-521; Sart, et al., The microenvironment of embryoid bodies modulated the commitment to neural lineage post-cryopreservation, Tissue Eng Part C: Methods., 21 (2015) 356-366). To evaluate the influence of glycogen synthase kinase (GSK)-3p inhibitor, CHIR99021 (1 or 10 µM) was added to the cultures treated with 1 µM $A\beta_{1-42}$ oligomers for three days and characterized.

Briefly, the replated neural cells were incubated with 5 mg/mL 3-(4,5-Dimethylthiazol-2-yl)-2,5-diphenyltetrazolium bromide (MTT, Sigma) solution. The absorbance was measured at 500 nm using a microplate reader (Biorad, Richmond, Calif.). Image-iT™ Live Green Reactive Oxygen Species Detection kit (Molecular Probes) was used to detect the intracellular ROS. Briefly, neural cells were seeded at $1\times10^5$/mL in 96-well plates (100 µL). After 3 days, the cells were rinsed with Hank's balanced salt solution and incubated with 25 µM carboxy-$H_2$DCFDA for 30 min at 37° C. The samples were washed and measured under a fluorescence microplate reader using 488 nm excitation wavelength and 530 nm for emission (Bio-Tek, FLx800, Winoosk, Vt.). Image-iT™ Live Green Poly Caspase Detection kit (Molecular Probes) was used to detect the expression of caspases. The replated cells were incubated for one hour with the fluorescent inhibitor of caspases reagent and analyzed by a fluorescence microplate reader.

MTT activity affirmed the cell viability study, with differential reduction in MTT activity in all cells upon exposure to 1 µM $A\beta_{1-42}$ oligomer, as seen in FIG. 78. Exposure to 5 µM $A\beta_{1-42}$ oligomer resulted in significant drops in MTT activity, especially in the control and Cyclopamine-induced cortical neurons. The expression of oxidative stress, indicated by ROS expression, displayed a corresponding increase for the groups that had decreased cell viability, seen in FIG. 79. Caspase expression was consistent with ROS results, as seen in FIG. 80.

Exposure to amyloid proteins also altered protein expression in the cells. Cells were grown without any growth factors or induced using the Cyclo and Pumro methodology. Cells were split on day 7 and grown as provided above or concurrently exposed to 1 µM $A\beta_{1-42}$ oligomers. The cells were stained on day 35 for glutamate, β-tubulin III, and Hoechst dye or synapsin I, β-tubulin III, and Hoechst dye, as provided for in Table 1. Cells without any growth factor treatment (controls) expressed relatively high amounts of glutamate, which did show some colocalization with β-tubulin III (data not shown). Staining of control cells with synapsin I showed a high level of colocalization of synapsin I with β-tubulin III (data not shown). Exposure to $A\beta_{1-42}$ resulted in a substantial drop in glutamate and synapsin I expression (data not shown). Similar results were seen in Cyclo-induced cells, with high levels of glutamate and colocalization of synapsin I and β-tubulin III in non-amyloidogenic cells. Similar to the controls, the Cyclo-induced cells also exhibited a substantial drop in glutamate. However, Cyclo-induced cells showed less synapsin I expression, but did still show localization of synapsin I with β-tubulin III (data not shown). Purmo-induced cells expressed less glutamate than control or Cyclo-induced cells, but did exhibit strong colocalization of synapsin I and β-tubulin, similar to control and Cyclo-induced cells (data not shown). Additionally, Purmo-induced cells also showed substantial drop in glutamate expression with exposure to $A\beta_{1-42}$ protein. Thus, the influence of $A\beta_{1-42}$ on the synaptogenesis and/or functional maintenance of the derived neuronal cells. Further testing on the Cyclo-induced cortical neurons was performed. Cells were induced using the Cyclo-methodology, as described above. On day 39, the cells were exposed to 0 µM, 1 µM, or 5 µM of $A\beta_{1-42}$ oligo for 3 days. The cells were stained for $A\beta_{1-42}$ (Aβ42) antibody, β-tubulin III, and Hoechst dye. As expected, staining with Aβ42 showed increasing staining with increased $A\beta_{1-42}$ oligo concentration, as seen in FIG. 81A, FIG. 82A, and FIG. 83A. By contrast, as $A\beta_{1-42}$ oligo concentrations increased, β-tubulin III staining dropped, as seen in FIG. 81B, FIG. 82B, and FIG. 83B, which is not merely caused by drop in cell number as shown by Hoechst staining, seen in FIG. 81C, FIG. 82C, and FIG. 83C. This indicated increased amounts of AP resulted in lower expression of β-tubulin. Surprisingly, staining of Aβ tended to colocalize with β-tubulin III (data not shown).

Cellular response induced by 1 µM $A\beta_{1-42}$ oligomers was then evaluated in the presence of GSK-3β inhibitor CHIR99021 (CH) at 1 µM and 10 µM for day 46 cells (Liu, et al., Deficiency in LRP6-mediated Wnt signaling contributes to synaptic abnormalities and amyloid pathology in Alzheimer's disease, Neuron, 84 (2014) 63-77; Wan, et al., The role of Wnt signaling in the development of Alzheimer's disease: a potential therapeutic target?, Biomed Res Int, 2014 (2014) 301575), as discussed above, using day 46 neural cells. In the presence of CH (10 M), MTT activity was increased (by 25-45%) compared to the groups without CH or with 1 µM CH, as seen in FIG. 84. Consistently, ROS, seen in FIG. 85, and caspase levels, seen in FIG. 86, were reduced in the presence of CH (10 µM) compared to the groups without CH or with 1 µM CH, indicating that GSK-33 inhibitor may attenuate Aβ-induced cytotoxicity, in particular for the Cyclo group. These results demonstrate the feasility of modulating Wnt signaling to study Aβ-induced pathology in 3-D cortical spheroids.

Discussion

Understanding the influence of neural patterning factors in hPSC-derived 3-D cultures is critical for constructing human brain-like tissue models and studying differential cellular responses of specific neuronal subtypes (Kondo, et al., Modeling Alzheimer's disease with iPSCs reveals stress phenotypes associated with intracellular Abeta and differential drug responsiveness, Cell Stem Cell, 12 (2013) 487-496; Mertens, et al., Differential responses to lithium in hyperexcitable neurons from patients with bipolar disorder, Nature, 527 (2015) 95-99; Mariani, et al., FOXG1-dependent dysregulation of GABA/Glutamate neuron differentiation in Autism Spectrum Disorders, Cell, 162 (2015) 375-390). Cortical glutamatergic neurons and motor neurons were generated and characterized using EB-based differentiation by tuning SHH signaling along with other factors (FGF-2, RA, and CHIR99021). Moreover, the formed cells showed differential cellular responses to MMP-2/-9 inhibitors, NMDA, and $A\beta_{1-42}$ oligomers from different neuronal populations.

Neural patterning in 3-D differentiation from hPSCs in vitro aims to mimic in vivo regional patterning of human brain (Suzuki & Vanderhaeghen, Is this a brain which I see before me? Modeling human neural development with pluripotent stem cells, Development, 142 (2015) 3138-3150). SHH signaling that patterns ventral part of neural tube in vivo has been used to derive a specific neuronal cell type in vitro in combination with several other signaling pathways, such as Wnt, RA, and FGF-2 (Maury, et al., Combinatorial analysis of developmental cues efficiently converts human pluripotent stem cells into multiple neuronal subtypes, Nat Biotechnol, 33 (2015) 89-96). As a ventralization factor, SHH influences neural patterning (D-V axis) in forebrain, midbrain, and hindbrain (Briscoe & Therond, The mechanisms of Hedgehog signalling and its roles in development and disease, Nat Rev Mol Cell Biol, 14 (2013) 416-429). SHH activation plus Wnt inhibition results in the generation of ventral telencephalic cells (Vazin, et al., The effect of multivalent Sonic hedgehog on differentiation of human embryonic stem cells into dopaminergic and GABAergic neurons, Biomaterials, 35 (2014) 941-948), while SHH inhibition leads to the generation of dorsal telencephalic progenitors and helps cortical tissue development (van den Ameele, et al., Thinking out of the dish: what to learn about cortical development using pluripotent stem cells, Trends Neurosci, 37 (2014) 334-342). On the contrary, Wnt activation enriches neural progenitor populations from posterior (P) hindbrain/spinal cord and is used for deriving motor neurons, while low Wnt signaling is required for generating anterior (A) forebrain neurons (affecting A-P axis) (Imaizumi, et al., Controlling the regional identity of hPSC-derived neurons to uncover neuronal subtype specificity of neurological disease phenotypes, Stem Cell Reports, 5 (2015) 1010-1022; Du, et al., Generation and expansion of highly pure motor neuron progenitors from human pluripotent stem cells, Nat Commun, 6 (2015) 6626; Moya, et al., Endogenous WNT signaling regulates hPSC-derived neural progenitor cell heterogeneity and specifies their regional identity, Stem Cell Reports, 3 (2014) 1015-1028). Recent advancements in organogenesis of hPSCs demonstrate the importance of understanding neural patterning factors in 3-D cultures (Suzuki & Vanderhaeghen, Is this a brain which I see before me? Modeling human neural development with pluripotent stem cells, Development, 142 (2015) 3138-3150; Lancaster & Knoblich, Organogenesis in a dish: modeling development and disease using organoid technologies, Science, 345 (2014) 1247125; Li, et al., In vitro organogenesis from pluripotent stem cells, Organogenesis, 10 (2014) 159-163). Our study enriched cortical neurons with dorsal telencephalic origin under SHH inhibition and motor neurons under SHH activation in the presence of caudalization factors (e.g., RA, Wnt activation by CHIR99021) in 3-D EB-based differentiation. In future, using 3-D differentiation systems that provide gradients of various patterning factors should be able to further promote the coordination of regional specification and neuronal subtypes of human brain tissues.

Moreover, dynamic remodeling of extracellular matrices (ECMs) during hiPSC neural differentiation is essential to construct 3-D brain-like tissues with appropriate structure (Ethell & Ethell, Matrix metalloproteinases in brain development and remodeling: synaptic functions and targets, J Neurosci Res, 85 (2007) 2813-2823; Van Hove, et al., An aberrant cerebellar development in mice lacking matrix metalloproteinase-3, Mol Neurobiol, 45 (2012) 17-29; Lancaster & Knoblich, Organogenesis in a dish: modeling development and disease using organoid technologies, Science, 345 (2014) 1247125; Luo, The role of matrix metalloproteinases in the morphogenesis of the cerebellar cortex, Cerebellum, 4 (2005) 239-245). ECM composition and remodeling, i.e., a balance of ECM secretion and degradation, not only affect cell adhesion sites but also influence signaling pathways that control stem cell fate and tissue development (Przybyla & Voldman, Attenuation of extrinsic signaling reveals the importance of matrix remodeling on maintenance of embryonic stem cell self-renewal, Proc Natl Acad Sci USA, 109 (2012) 835-840; Lu, et al., Extracellular matrix degradation and remodeling in development and disease, Cold Spring Harb Perspect Biol, 2011 (2011) a005058). In particular, MMPs are crucial proteins during ECM remodeling process (Lu, et al., Extracellular matrix degradation and remodeling in development and disease, Cold Spring Harb Perspect Biol, 2011 (2011) a005058; Daley, et al., Extracellular matrix dynamics in development and regenerative medicine, J Cell Sci, 121 (2008) 255-264). The activities of MMPs influence neural progenitor cell proliferation, migration, and lineage commitment (Ethell & Ethell, Matrix metalloproteinases in brain development and remodeling: synaptic functions and targets, J Neurosci Res, 85 (2007) 2813-2823; Barkho, et al., Endogenous matrix metalloproteinase (MMP)-3 and MMP-9 promote the differentiation and migration of adult neural progenitor cells in response to chemokines, STEM CELLS, 26 (2008) 3139-3149; Tonti, et al., Neural stem cells at the crossroads: MMPs may tell the way, Int J Dev Biol, 53 (2009) 1-17; Van Hove, et al., An aberrant cerebellar development in mice lacking matrix metalloproteinase-3, Mol Neurobiol, 45 (2012) 17-29; Szymczak, et al., Effect of matrix metalloproteinases inhibition on the proliferation and differentiation of HUCB-NSCs cultured in the presence of adhesive substrates, Acta Neurobiol Exp (Wars), 70 (2010) 325-336), and were suggested to play a role in long-term brain memory (Tsien, Very long-term memories may be stored in the pattern of holes in the perineuronal net, Proc Natl Acad Sci USA, 110 (2013) 12456-12461; Nagy, et al., Matrix metalloproteinase-9 is required for hippocampal late-phase long-term potentiation and memory, J Neurosci, 26 (2006) 1923-1934). Therefore, understanding dynamic cell-matrix interactions and differential response of neuronal subtypes to MMP inhibition is important to regulate neural tissue development and understand neurological disease pathology. From our results, MMP-2/-9 inhibitors affected the migration and proliferation of motor neurons but had less effect on cortical excitatory neurons in short-term treatment (5 days). MMP-2/-9 mainly degrade type IV collagen and endogenous MMP-9 has been shown to promote the differentiation and migration of embryonic or adult neural progenitors (Barkho, et al., Endogenous matrix metalloproteinase (MMP)-3 and MMP-9 promote the differentiation and migration of adult neural progenitor cells in response to chemokines, STEM CELLS, 26 (2008) 3139-3149; Ingraham, et al., Matrix metalloproteinase (MMP)-9 induced by Wnt signaling increases the proliferation and migration of embryonic neural stem cells at low O2 levels, J Biol Chem, 286 (2011) 17649-17657). The differential cellular responses to MMP-2/-9 inhibitors indicate that the role of MMP-2/-9 may be neuronal subtype-dependent. It is also noted that this study used Geltrex as the substrate. Fully understanding the relationship between cells and the ECM proteins may need further study on the effects of different ECM substrates on the cellular responses to MMP inhibitors (Soleman, et al., Targeting the neural extracellular matrix in neurological disorders, Neuroscience, 253 (2013) 194-213; Lau, et al., Pathophysiology of the brain extracellular matrix: a new target for remyelination, Nat Rev Neurosci, 14 (2013) 722-729).

The diversity of human brain cell subtypes results in the selective cell death or region/circuit-specific dysfunctions in a variety of neurological diseases (Vazin, et al., Efficient derivation of cortical glutamatergic neurons from human pluripotent stem cells: a model system to study neurotoxicity in Alzheimer's disease, Neurobiol Dis, 62 (2014) 62-72; de Groot, et al., Don't judge a neuron only by its cover: neuronal function in in vitro developmental neurotoxicity testing, Toxicol Sci, 132 (2013) 1-7). However, numerous neuronal subtypes, complicated cellular interactions, and diverse genetic background of the patients pose a difficulty for drug development and disease modeling. In this regard, hiPSC-based neural models, particularly 3-D neural constructs that provides in vivo-like cell-cell interactions in human brain, may provide a novel platform to understand differential responses of various neuronal populations in a physiologically relevant testing environment (Schwartz, et al., Human pluripotent stem cell-derived neural constructs for predicting neural toxicity, Proc Natl Acad Sci USA, 112 (2015) 12516-12521; Engle & Puppala, Integrating human pluripotent stem cells into drug development, Cell Stem Cell, 12 (2013) 669-677). So, characterization of cell populations and cellular response in 3-D cultures along brain tissue development should advance the development of hiPSC-based neural models.

NMDA-induced excitotoxicity represents a possible mechanism in the pathogenesis of ischemic brain tissue (Beraki, et al., A pharmacological screening approach for discovery of neuroprotective compounds in ischemic stroke, PLoS One, 8 (2013) e69233) as well as neurodegenerative conditions (e.g., Alzheimer's disease) (Lopes, et al., Galantamine potentiates the neuroprotective effect of memantine against NMDA-induced excitotoxicity, Brain Behav, 3 (2013) 67-74). Overexposure to NDMA may over activate NDMA receptor and lead to neuronal cell death. In our study, different neuronal subtypes showed similar responses to NMDA-induced neurotoxicity as well as carbenoxolone treatment, which is in line with previous reports showing that NDMA exposure has general influence on the neuronal cells of central nervous system (Beraki, et al., A pharmacological screening approach for discovery of neuroprotective compounds in ischemic stroke, PLoS One, 8 (2013) e69233).

Modeling Alzheimer's disease (AD) using hPSC-derived cortical neurons has emerged as a promising tool to understand disease progression and to screen therapeutic drugs (Kondo, et al., Modeling Alzheimer's disease with iPSCs reveals stress phenotypes associated with intracellular Abeta and differential drug responsiveness, Cell Stem Cell, 12 (2013) 487-496; Israel, et al., Probing sporadic and familial Alzheimer's disease using induced pluripotent stem cells, Nature, 482 (2012) 216-220). The ability of hPSC-derived cortical neurons to model AD has been illustrated using patient-specific hiPSC lines mostly in 2-D cultures (Kondo, et al., Modeling Alzheimer's disease with iPSCs reveals stress phenotypes associated with intracellular Abeta and differential drug responsiveness, Cell Stem Cell, 12 (2013) 487-496; Israel, et al., Probing sporadic and familial Alzheimer's disease using induced pluripotent stem cells, Nature, 482 (2012) 216-220). For example, hiPSC-derived neurons from AD patients (two familial and one sporadic) demonstrated the elevated levels of $A\beta_{40}$, phosphor-tau and active GSK-33 (Israel, et al., Probing sporadic and familial Alzheimer's disease using induced pluripotent stem cells, Nature, 482 (2012) 216-220). In another study, extracellular $A\beta_{42}$ increased with the decrease in intracellular $A\beta_{42}$ in familial AD-derived cells compared to the healthy neural cells (Kondo, et al., Modeling Alzheimer's disease with iPSCs reveals stress phenotypes associated with intracellular Abeta and differential drug responsiveness, Cell Stem Cell, 12 (2013) 487-496). Differential response to decosahexaenoic acid (DHA) for neural cells derived from hiPSCs of different AD patients indicated that DHA treatment may be used for a subset of patients (Kondo, et al., Modeling Alzheimer's disease with iPSCs reveals stress phenotypes associated with intracellular Abeta and differential drug responsiveness, Cell Stem Cell, 12 (2013) 487-496). Previously, 3-D cultures of hiPSC-derived neural progenitors have been shown to better recapitulate AD pathology and display higher levels of co-localization of debrin and F-actin than 2-D cultures (Zhang, et al., A 3D Alzheimer's disease culture model and the induction of P21-activated kinase mediated sensing in iPSC derived neurons, Biomaterials, 35 (2014) 1420-1428), but this model did not demonstrate differential cellular behaviors of various neuronal subtypes. $A\beta_{1-42}$ oligomers caused more detrimental effects on 3-D cultures mostly comprised of cortical excitatory neurons than those of motor neurons. The potential of 3-D neural models with multiple neuronal subtypes derived from hiPSCs would benefit the identification of therapeutic drugs for the treatment of neurological diseases that only affect specific types of neural cells (Mertens, et al., Differential responses to lithium in hyperexcitable neurons from patients with bipolar disorder, Nature, 527 (2015) 95-99).

This study indicates that cortical glutamatergic neurons and motor neurons can be generated by tuning sonic hedgehog signaling along with other factors in Wnt and RA signaling based on 3-D EB formation from hiPSCs. The differential response of neuronal subtypes to different biomolecules reveals the importance of physiologically relevance of the neural culture models for neurotoxicity and neuropathological study. This study has implications in establishing 3-D models for neurological disease modeling and drug discovery.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of preparing a three-dimensional cellular model to replicate neuronal response, consisting essentially of:
   - providing human iPSK3 cells in a medium containing rho-associated kinase pathway inhibitor;
   - incubating the cells in the medium containing the rho-associated kinase pathway inhibitor for 24 hours wherein the cells form embryoid bodies;
   - replacing the medium with a second medium containing SMAD pathway inhibitors 4-(4-(benzo[d][1,3]dioxol-5-yl)-5-(pyridin-2-yl)-1H-imidazol-2-yl)benzamide at a concentration of 10 uM and 4-[6-[4-(1-piperazyl)phenyl]pyrazol[1,5-a]pyrimidin-3-yl]-quinoline at a concentration of 100 nM;
   - incubating the cells in the second medium containing the SMAD pathway inhibitors for 7 days;
   - replacing the medium with a third medium containing cyclopamine at a concentration of between 0.3 μM to 1.5 μM;
   - incubating the cells in the third medium containing the cyclopamine for between 7-10 days;
   - transferring the cells to a basement membrane extract; and
   - wherein the plurality of the human iPSK3 cells are disposed into at least one spheroid structure, wherein the plurality of human iPSK3 cells are integrated into cortical layer-specific structures.

2. The method of claim 1, wherein the rho-associated kinase pathway inhibitor is (+)-(R)-trans-4-(1-aminoethyl)-N-(4-pyridyl)cyclohexanecarboxamide dihydrochloride.

3. The method of claim 1, further comprising:
   - introducing the human iPSK3 cells into a spinner bioreactor, wherein the spinner bioreactor is in fluid communication with a cell medium flow device;
   - flowing the first medium through the spinner bioreactor;
   - flowing the second medium through the spinner bioreactor;
   - allowing the human iPSK3 cells to form at least one spheroid structure, wherein the human iPSK3 cells form cortical layer-specific structure and synaptic activities.

4. The method of claim 3, wherein the human iPSK3 cells are introduced at a density of $4.0\text{-}4.5\times10^5$ cells/mL.

5. The method of claim 3, wherein the spinner bioreactor is glass.

6. The method of claim 3, wherein the flow of the cell medium is 3-15 dyne/cm$^2$.

* * * * *

SEQUENCE LISTING

<160> NUMBER OF SEQ ID NOS: 10

<210> SEQ ID NO 1
<211> LENGTH: 21
<212> TYPE: DNA

```
<213> ORGANISM: artificial sequence
<220> FEATURE:
<223> OTHER INFORMATION: Forward primer for TBR1

<400> SEQUENCE: 1
tgcgcaccca ctcattttat t                                          21

<210> SEQ ID NO 2
<211> LENGTH: 21
<212> TYPE: DNA
<213> ORGANISM: artificial sequence
<220> FEATURE:
<223> OTHER INFORMATION: Reverse primer for TBR1

<400> SEQUENCE: 2
ggtcggtgag ctaattgcag a                                          21

<210> SEQ ID NO 3
<211> LENGTH: 22
<212> TYPE: DNA
<213> ORGANISM: artificial sequence
<220> FEATURE:
<223> OTHER INFORMATION: Forward primer for HOXB4

<400> SEQUENCE: 3
aattccttct ccagctccaa ga                                         22

<210> SEQ ID NO 4
<211> LENGTH: 19
<212> TYPE: DNA
<213> ORGANISM: artificial sequence
<220> FEATURE:
<223> OTHER INFORMATION: Reverse primer for HOXB4

<400> SEQUENCE: 4
cctggatgcg caaagttca                                             19

<210> SEQ ID NO 5
<211> LENGTH: 21
<212> TYPE: DNA
<213> ORGANISM: artificial sequence
<220> FEATURE:
<223> OTHER INFORMATION: Forward primer for vGLUT1

<400> SEQUENCE: 5
ccccaattcc tcgcacttta t                                          21

<210> SEQ ID NO 6
<211> LENGTH: 21
<212> TYPE: DNA
<213> ORGANISM: artificial sequence
<220> FEATURE:
<223> OTHER INFORMATION: Reverse primer for vGLUT1

<400> SEQUENCE: 6
gggaaggatc ccagattttg a                                          21

<210> SEQ ID NO 7
<211> LENGTH: 21
<212> TYPE: DNA
<213> ORGANISM: artificial sequence
<220> FEATURE:
<223> OTHER INFORMATION: Forward primer for MNX1

<400> SEQUENCE: 7
tgaaacttga aaccgcctct g                                          21
```

```
<210> SEQ ID NO 8
<211> LENGTH: 21
<212> TYPE: DNA
<213> ORGANISM: artificial sequence
<220> FEATURE:
<223> OTHER INFORMATION: Reverse primer for MNX1

<400> SEQUENCE: 8
agcagtttga acgctcgtga c                                          21

<210> SEQ ID NO 9
<211> LENGTH: 20
<212> TYPE: DNA
<213> ORGANISM: artificial sequence
<220> FEATURE:
<223> OTHER INFORMATION: Forward primer for beta actin

<400> SEQUENCE: 9
gtactccgtg tggatcggcg                                            20

<210> SEQ ID NO 10
<211> LENGTH: 22
<212> TYPE: DNA
<213> ORGANISM: artificial sequence
<220> FEATURE:
<223> OTHER INFORMATION: Reverse primer for beta actin

<400> SEQUENCE: 10
aagcatttgc ggtggacgat gg                                         22
```